(12) United States Patent  (10) Patent No.: US 7,429,658 B2
Howard et al.  (45) Date of Patent: Sep. 30, 2008

(54) SYNTHESIS OF PROTECTED PYRROLOBENZODIAZEPINES

(75) Inventors: Philip Howard, London (GB); Luke Masterson, London (GB)

(73) Assignee: Spirogen Limited, Isle of Wight (GB)

( * ) Notice: Subject to any disclaimer, the term of this patent is extended or adjusted under 35 U.S.C. 154(b) by 147 days.

(21) Appl. No.: 10/571,274

(22) PCT Filed: Sep. 10, 2004

(86) PCT No.: PCT/GB2004/003873

§ 371 (c)(1),
(2), (4) Date: Mar. 9, 2006

(87) PCT Pub. No.: WO2005/023814

PCT Pub. Date: Mar. 17, 2005

(65) Prior Publication Data

US 2006/0264622 A1  Nov. 23, 2006

(30) Foreign Application Priority Data

Sep. 11, 2003 (GB) ................................. 0321295.8

(51) Int. Cl.
*C07D 487/04* (2006.01)
*C07D 207/00* (2006.01)
*C07C 261/00* (2006.01)

(52) U.S. Cl. .................... 540/496; 548/539; 560/24; 560/32

(58) Field of Classification Search ................ 540/496; 548/539; 560/24, 32
See application file for complete search history.

(56) References Cited

U.S. PATENT DOCUMENTS

| 3,523,941 | A | 8/1970 | Leimgruber et al. |
|---|---|---|---|
| 3,524,849 | A | 8/1970 | Batcho et al. |
| 4,185,016 | A | 1/1980 | Takanabe et al. |
| 4,239,683 | A | 12/1980 | Takanabe et al. |
| 4,309,437 | A | 1/1982 | Ueda et al. |
| 5,143,854 | A | 9/1992 | Pirrung et al. |
| 5,418,241 | A * | 5/1995 | Jegham et al. ............... 514/322 |
| 5,545,568 | A | 8/1996 | Ellman et al. |
| 6,562,806 | B1 | 5/2003 | Thurston et al. |
| 6,608,192 | B1 | 8/2003 | Thurston et al. |
| 6,660,856 | B2 | 12/2003 | Wang |
| 6,747,144 | B1 | 6/2004 | Thurston et al. |
| 2003/0120069 | A1 | 6/2003 | Thurston et al. |
| 2003/0195196 | A1 | 10/2003 | Thurston et al. |
| 2004/0092736 | A1 | 5/2004 | Thurston et al. |
| 2004/0198722 | A1 | 10/2004 | Thurston et al. |

FOREIGN PATENT DOCUMENTS

| EP | 0239400 A2 | 9/1987 |
|---|---|---|
| EP | 1193270 | 4/2002 |
| FR | 2027356 | 12/1969 |
| FR | 2586683 D | 3/1987 |
| GB | 1299198 D | 12/1972 |
| GB | 2053894 | 2/1981 |
| JP | 53-82792 | 7/1978 |
| JP | 57131791 | 8/1982 |
| JP | 58180487 | 10/1983 |
| WO | WO 88/04659 | 6/1988 |
| WO | WO 88/07378 | 10/1988 |

(Continued)

OTHER PUBLICATIONS

Weidner-Wells et al. (Journal of Organic Chemistry (1989), 54(24), 5746-58).*
Adams et al., "Molecular modelling of a sequence-specific DNA-binding agent based on the pyrrolo[2,1-c][1,4]benzodiazepines," Pharm. Pharmacol. Commun. (1999) 5:555-560.

(Continued)

*Primary Examiner*—Bruck Kifle
(74) *Attorney, Agent, or Firm*—Michael Best & Friedrich LLP

(57) ABSTRACT

A method of synthesis of a N-10 protected PBD compound of formula (I):

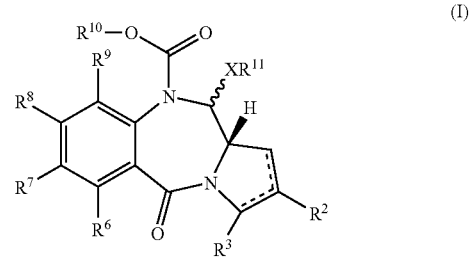

via an intermediate of formula (II) or formula (V):

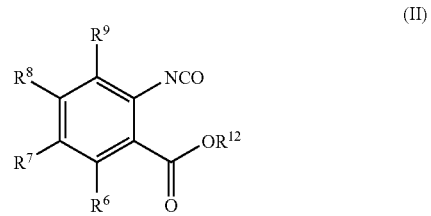

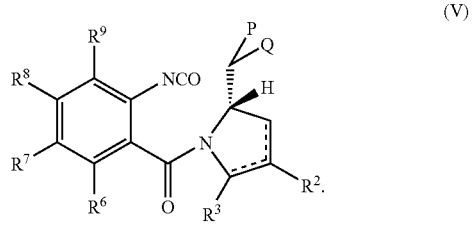

7 Claims, No Drawings

FOREIGN PATENT DOCUMENTS

| WO | WO 89/10140 | 11/1989 |
|---|---|---|
| WO | WO 91/16324 | 10/1991 |
| WO | WO 92/19620 D | 11/1992 |
| WO | WO 93/08288 | 4/1993 |
| WO | WO 93/18045 | 9/1993 |
| WO | WO 96/23497 | 8/1996 |
| WO | WO 97/01560 D | 1/1997 |
| WO | WO 97/07097 | 2/1997 |
| WO | WO 98/11101 | 3/1998 |
| WO | WO 98/12197 | 3/1998 |
| WO | WO 99/29642 | 6/1999 |
| WO | WO 99/46244 | 9/1999 |
| WO | WO 00/12506 | 3/2000 |
| WO | WO 00/12507 | 3/2000 |
| WO | WO 00/12508 | 3/2000 |
| WO | WO 00/12509 | 3/2000 |
| WO | WO 00/64864 | 11/2000 |
| WO | WO 2004/043963 | 5/2004 |
| WO | WO 2005/023814 | 3/2005 |
| WO | WO 2005/040170 | 5/2005 |
| WO | WO 2005/085251 | 9/2005 |

OTHER PUBLICATIONS

Albericio, F. et al., "NPE-Resin, A New Approach to the Solid-Phase Synthesis of Protected Peptides and Oligonucleotides II. Synthesis of Protected Peptides[1,2]," *Tetrahedron Letters*, 32:1515-1518 (1991).

Albericio, F. et al., "NPE-resin, a new approach to the solid-phase synthesis of protected peptides and oligonucleotides," *Peptides* 1990, Proc. 21.sub.st Eur. Pept. Symp., 134-136 (1990).

Althius, T. H. and Hess, H. J., "Synthesis and Identification of the Major Metabolites of Prazosin Formed in Dog and Rat," *J. Medicinal Chem.*, 20(1), 146-148 (1977).

Arima et al., "Studies on Tomaymycin, a New Antibiotic. I. Isolation and Properties of Tomaymycin," *J. Antibiotics*, 25, 437-444 (1972).

Aristoff, J and Johnson, P., "Synthesis of CBI-PDE-I-Dimer, the Benzannelated Analogue of CC-1065," *J. Org. Chem.*, 57, 6234-6239 (1992).

Bagshawe et al., "Antibody-Enzyme Conjugates Can Generate Cytotoxic Drugs from Inactive Precursors at Tumor Sites," *Antibody, Immunoconjugates, and Radiopharmaceuticals*, 4, 915-922 (1991).

Baraldi, P.G. et al., "Design, synthesis and biological activity of a pyrrolo[2,1-c][1,4]benzodiazepine (PBD)-distamycin hybrid," *Bioorganic & Medicinal Chemistry Letters*, vol. 8, No. 21, 3019-3024 (1998).

Baraldi, P.G. et al., "Synthesis, in Vitro Antiproliferative Activity, and DNA-Binding Properties of Hybrid Molecules Containing Pyrrolo[2,1-c][1,4]benzodiazepine and Minor-Groove-Binding Oligopyrrole Carriers," *J. Med. Chem.*, 42, 5131-5141 (1999).

Baraldi, P.G. et al., "[2,1-c][1,4]benzodiazepine (PBD)-distamycin hybrid inhibits DNA binding to transcription factor Sp1," *Nucleotides and Nucleic Acids* (2000) 19(8):1219-1229.

Bayley, H. et al., "Photoactivatable drugs," *TIPS*, 8, 138-143 (1987).

Berge et al., "Pharmaceutical Salts," *J. Pharm. Sci.* (1977) 66:1-19.

Berry, J. M. et al., "Solid-phase synthesis of DNA-interactive pyrrolo[2,1-c][1,4]benzodiazepines," *Tetrahedron Letters*, 41, 6171-6174 (2000).

Bi, Y. et al., "Building blocks for peptide and carbamate libraries", *Bioorganic & Medicinal Chemistry Letters*, vol. 6, No. 19, 2299-2300 (1996).

Bi, Y., et al., "Building blocks for peptide and carbamate libraries," *Chemical Abstracts*, vol. 125, No. 23, 1013 (1996).

Boger et al., "CC-1065 and the Duocarmycins: Synthetic Studies," *Chem. Rev.*, 97, 787-828 (1997).

Borgatti, M. et al., "Inhibition of NF-kB/DNA interactions and HIV-1 LTR directed transcription by hybrid molecules containing pyrrolo[2,1-c][1,4] benzodiazepine (PBD) and oligopyrrole carriers," *Drug Development Research* (2003) 60(3):173-185.

Bose et al., "New Approaches to Pyrrolo[2,1-c][1,4]benzodiazepines: Synthesis, DNA-binding and cytotoxicity of DC-81," *Tetrahedron*, 48, 751-758 (1992).

Bose, D.S. et al., "Rational Design of a Highly Efficient Irreversible DNA Interstrand Cross-Linking Agent Based on the Pyrrolobenzodiazepine Ring System," *J. Am. Chem. Soc.*, 114, 4939-4941 (1992).

Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.

Bridges, R.J. et al., "Conformationally Defined Neurotransmitter Analogues. Selective Inhibition of Glutamate Uptake by One Pyrrolidine-2,4-dicarboxylate Diastereomer," *J. Med. Chem.*, 34, 717-725 (1991).

Brown, S.C. et al., "NMR Solution Structure of a Peptide Nucleic Acid Complexed with RNA," *Science*, 265, 777-780 (1994).

Bundgaard, H., "Design and Application of Prodrugs," *A Textbook of Drug Design and Development*, eds Krogsgaard-Lassen, P., and Bundgaard, H., Harwood Academic Press, 113-135 (1991).

Burgess, K. et al., "Solid Phase Synthesis of Oligoureas", *J.Ame. Chem. Soc.*, 119: 1556-1564 (1997).

Burgess, K et al., "Solid Phase Synthesis of Unnatural Biopolymers Containing Repeating Urea Units," *Agnew Chem. Int. Ed. Engl*, 34, No. 8:907-909 (1995).

Carruth, J.A.S., "Clinical applications for photodynamic therapy," *J. Photochem Photobiol.*, 9, 396-397 (1991).

Chen, Z. et al., "A novel approach to the synthesis of cytotoxic C2-C3 unsaturated pyrrolo[2,1-c][1,4]benzodiazepines (PBDs) with conjugated acrylyl C2-substiuents," Biorg. Med. Chem. Lett. (2004) 14:1547-1549.

Cho, C Y et al., "An Unnatural Biopolymer", *Science*, 261: 1303-1305 (1993).

Cooper, N. et al., "Synthesis of novel PBDs as anti-tumour agents," Chem. Commun. (2002) 16:1764-1765.

Courtney, S. M. et al., "A new convenient procedure for the synthesis of pyrrolo[2,1-c][1,4]benzodiazepines", *Tetrahedron Letters*, vol. 34, No. 33, 5327-28 (1993).

Culver et al., "In Vivo Gene Transfer with Retroviral Vector-Producer Cells for Treatment of Experimental Brain Tumors," *Science*, 256, 1550-1552 (1992).

Dalton, S. and Treisman, R, "Characterization of SAP-1, a Protein Recruited by Serum Response Factor to the c-*fos* Serum Response Element," *Cell*, 68, 597-612 (1992).

Damayanthi, Y., et al., "Design and synthesis of novel pyrrolo 2,1-c[1,4] benzodiazepine-Lexitropsin Conjugates," *J. Org. Chem.*, 64, 290-292 (1999).

Dangles, O. et al., "Selective Cleavage of the Allyl and Allyloxycarbonyl Groups through Palladium-Catalyzed Hydrostannolysis with Tributyltin Hydride. Application to the Selective Protection-Deprotection of Amino Acid Derivatives and in Peptide Synthesis," *J. Org. Chem.*, 52, 4984-4993 (1987).

De Groot, FMH et al., "Synthesis and biological evaluation of 2'-carbamate-linked 2'-carbonate-linked prodrugs of paclitaxel: selective activation by the tumor-associated protease plasmin," J. Med. Chem. (2000) 43(16):3093-3102.

De Groot, FMH et al., "Novel 20-carbonate linked prodrugs of camptothecin and 9-aminocamptothecin designed for activation by tumour-associated plasmin," Biorg. Med. Chem. Lett. (2002) 12(17):2371-2376.

*Dictionary of Science and Technology*, Professor P.M.B. Walker ed. Larousse plc., pp. 63, 457, 523 (1995).

Dressman, B.A., et al., "Solid Phase Synthesis of Hydantoins Using a Carbamate Linker and a Novel Cyclization/Cleavage Step," *Tetrahedron Letters*37, 937-940 (1996).

Drost, K.J. and Cava, M.P., "A Photochemically Based Synthesis of the Benzannelated Analogue of the CC-1065 A Unit," *J. Org. Chem.*, 56:2240-2244 (1991).

Dubowchik, G.M. et al., "Cathepsin B-sensitive dipeptide prodrugs. 1. A model study of structural requirements for efficient release of doxorubicin," Biorg. Med. Chem. Lett. (1998) 8:3341-3346.

Dubowchik, G.M. et al., "Cathepsin B-sensitive dipeptide prodrugs. 2. Models of anticancer drugs paclitaxel (Taxol), Mitomycin C and Doxorubicin," Biorg. Med. Chem. Lett. (1998) 8:3347-3352.

Dubowchik and Walker, "Receptor-mediated and enzyme-dependent targeting of cytotoxix anticancer drugs," Pharmacology and Therapeutics (1999) 83:67-123.

Eashoo, M. et al., "Fibers from a Low Dielectric Constant Fluorinated Polyimide: Solution Spinning and Morphology Control," *J. Polymer Science*, 35:173-185 (1997).

Edman, P. and Begg, G., "A Protein Sequenator," *Eur. J. Biochem.*, 1, 80-91 (1967).

Egholm, M et al., "Peptide Nucleic Acids (PNA). Oligonucleotide Analogues with an Achiral Peptide Backbone," *J. Am. Chem. Soc.*, 114, 1895-1897 (1992).

Egholm, M et al., "PNA hybridizes to complementary oligonucleotides obeying the Watson-Crick hydrogen-bonding rules," *Nature*, 365, 566-568 (1993).

Englehardt et al., "Direct gene transfer of human CFTR into human bronchial epithelia of xenografts with E1-deleted adenoviruses," *Nature Genetics*, 4, 27-34 (1993).

Farmer, J.D. et al., "DNA binding properties of a new class of linked anthramycin analogs,", *Chemical Abstracts*, Abstract No. 239940r, vol. 114, No. 25, 25 899-903 (1991).

Figliozzi, G.M. et al., "Synthesis of N-substituted Glycine Peptoid Libraries," *Methods in Enzymology*, 267: 437-447 (1996).

Foloppe, M.P. et al., "DNA-binding properties of pyrrolo[2,1-c][1,4]benzodiazephine N10-C11 amidines," *Eur. J. Med. Chem.*, 31, 407-410 (1996).

Fujisawa Pharmaceutical Co., Ltd., Abstract No. 139983k, "Benzodiazepine derivatives", *Chemical Abstracts*, vol. 99, No. 17, 603 (1983).

Fujisawa Pharmaceutical Co., Ltd., Abstract No. 72145x, "Benzodiazepine derivatives", *Chemical Abstracts*, vol. 98, No. 9, 638 (1983).

Fujisawa Pharmaceutical Co. Ltd., "Benzodiazepine derivatives," *SciFinder Scholar*, 2-3 (2002).

Fukuyama, T. et al., "Total Synthesis of (+)-Porothramycin B," *Tetrahedron Letters*, vol. 34, 16, 2577-2580 (1993).

Furka, A. et al., "General method for rapid synthesis of multicomponent peptide mixtures," *Int. J. Peptide Protein Res.*, 37, 487-493 (1991).

Garcia-Echeverria, C., "A Base Labile Handle for Solid Phase Organic Chemistry", *Tetrahedron Letters*, 38,52, 8933-8934 (1997).

Garsky et al., "The synthesis of a prodrug of doxorubicin designed to provide reduced systemic toxicity and greater target efficacy," J. Med. Chem. (2001) 44:4216-4224.

Grant, R. et al., *Grant and Hackh's Chemical Dictionary*, McGraw-Hill Book Company, 282 (1987).

Greene, T.W. and Wuts, P.G.M., *Protective Groups in Organic Synthesis*, John Wiley & Sons, 2nd ed., Ch 7, 315-345 (1991).

Gregson, S. et al., "Synthesis of a novel C2/C2'-exo unsaturated pyrrolobenzodiazepine cross-linking agent with remarkable DNA binding affinity and cytotoxicity," *Chemical Communications*, 797-798 (1999).

Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.

Gregson, S.J. et al., "Design, Synthesis and Evaluation of a Novel Pyrrolobenzodiazepine DNA-Interactive Agent with Highly Efficient Cross-Linking Ability and Potent Cytotoxicity", *J. Med. Chem.*, 44: 737-748 (2001).

Gregson, S.J. et al., "Effect of C2-*exo* Unsaturation on the Cytotoxicity and DNA-Binding Reactivity of Pyrrolo[2,1-c]1,4]benzodiazepines", *Bioorganic & Medicinal Chemistry Letters*, 10: 1845-1847 (2000).

Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.

Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.

Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.

Guiotto, A. et al., "Synthesis of novel C7-aryl substituted pyrrolo[2,1-c][1,4]benzodiazepines (PBDs) via Pro-N10-troc protection and suzuki coupling," *Bioorganic& Medicinal Chemistry Letters*, 8, No. 21, 3017-3018 (1998).

Hamburger, A.W. et al., "Primary bioassay of human tumor stem cells," Science (1977) 197:461-643.

Hara et al., "DC 102, a new glycosidic pyrrolo(1,4)benzodiazepine antibiotic produced by *streptomyces* sp.", *J. Antibiotics*, 41, 702-704 (1988).

Hauske, J. R. and Dorff, P., "Solid Phase CBZ Chloride Equivalent. A New Matrix Specific Linker", *Tetrahedron Letters*, 36, 10, 1589-1592 (1995).

Hocart et al., "Highly potent cyclic disulfide antagonists of somatostatin," *J. of Medicinal Chem.*, 42:11 (1999).

Hochlowski, J. et al., "Abbeymycin, a new anthramycin-type antibiotic produced by a streptomycete," *J. Antibiotics*, 40, 145-148 (1987).

Holmes, C.P. and Jones, D.G., "Reagents for Combinatorial Organic Synthesis: Development of a New O-Nitrobenzyl Photolabile Linker for Solid Phase Synthesis", *J. Org. Chem.*, 60, 2318-2319 (1995).

Huber, B. et al., "Retroviral-mediated gene therapy for the treatment of hepatocellular carcinoma: An innovative approach for cancer therapy," *Proc. Natl. Acad. Sci. USA*, 88, 8039-8043 (1991).

Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," *Acc. Chem. Res.*, 19, 230-237 (1986).

Itoh et al., "Sibanomicin, a new pyrrolo(1,4)benzodiazepine antitumor antibiotic produced by a *micromonospora* sp." *J. Antibiotics*, 41, 1281-1284 (1988).

Jakobsen et al., "Design, synthesis, and pharmacological evaluation of thapsigargin analogues for targeting apoptosis to prostatic cancer cells," J. Med. Chem. (2001) 44:4696-4703.

Jenkins, T.C. et al., "Structure of a Covalent DNA Minor Groove Adduct with a Pyrrolobenzodiazepine Dimer: Evidence for Sequence-Specific Interstrand Cross-Linking," *J. Med. Chem.*, 37, 4529-4537 (1994).

Jungheim, L.N. and Shepherd, T.A., "Design of Antitumor Prodrugs: Substrates for Antibody Targeted Enzymes," *Am. Chem. Soc. Chem. Rev.*, 94, 1553-1566 (1994).

Kamal, A., et al., "An Efficient Synthesis of Pyrrolo[2,1-c][1,4] Benzodiazepine Antibiotics via Reductive Cyclization," *Bioorg. Med. Chem. Ltrs*, 7, No. 14, 1825-1828 (1997).

Kamal, A., et al., "Synthesis of Pyrrolo [2,1-c][1,4]-Benzodiazepene Antibiotics: Oxidation of Cyclic Secondary Amine with TPAP", *Tetrahedron*, v. 53, No. 9, 3223-3230 (1997).

Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22):3955-3958.

Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.

Kaneko, T. et al., "Bicyclic and tricyclic analogues of anthramycin," J. Med. Chem. (1985) 28:388-392.

Kang, G.-D. et al., "Synthesis of a novel C2-aryl substituted 1,2-unsaturated pyrrolobenzodiazepine," Chem. Commun. (2003) 1688-1689.

Kapoor, T.M. et al., "Exploring the Specificity Pockets of Two Homologous SH3 Domains Using Structure-Based, Split-Pool Synthesis and Affinity-Based Selection," *J. Am. Chem. Soc.* 120:23-29 (1998).

Katritzky et al., *Heterocyclic Chemistry*, John Wiley & Sons, Inc., 247-253 (1960).

Kennedy, J.C. and Pottier, R.H., "Endogenous protoporphyrin IX, a clinical useful photosensitiser for photodynamic therapy," *J. Photochem. Photobiol.* 14, 275-292 (1992).

Kohn, K., "Anthramycin," *Antibiotics III*, Springer-Verlag, NY, 3-11 (1975).

Konishi, M. et al., "Chicamycin, a new antitumor antibiotic II. Structure determination of chicamycins A and B," *J. Antibiotics*, 37, 200-206 (1984).

Kumar, R. et al., "Synthesis and antitumor cytotoxicity evaluation of novel pyrrolo[2,1-c][1,4]benzodiazepine imidazole containing polyamide conjugates," Oncology Research (2003) 13(4):221-223.

Kumar, R. et al., "Design and synthesis of novel pyrrolo[2,1-c][1,4]benzodiazepine—imidazole containing polyamide conjugates," Heterocyclic Communications (2002) 81(1):19-26.

Kumar, R. et al., "Design, synthesis and in vitro cytotoxicity studies of novel pyrrolo [2,1][1,4]benzodiazepine - glycosylated pyrrole and imidazole polyamide conjugates," Org. Biomol. Chem. (2003) 1(19):3327-3342.

Kunimoto et al., "Mazethramycin, a new number of anthramycin group antibiotics," *J. Antibiotics*, 33, 665-667 (1980).

Kunz, H. and Dombo, B., "Solid Phase Synthesis of Peptide and Glycopeptides on Polymeric Supports with Allylic Anchor Groups," *Angew Chem. Int. Ed. Engl*, 5, 711-713 (1988).

Kuzmich, S. et al., "Increased levels of glutathione S-transferase π transcript as a mechanism of resistance to ethacrynic acid," *Journal of Biochemistry*, 281, 219-224 (1992).

Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," *J. Org. Chem.*, 52, 91-97 (1987).

Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.

Leber, J.D. et al., "A revised structure for sibiromycin," *J. Am. Chem. Soc.*, 110, 2992-2993 (1988).

Leimgruber, W. et al., "Isolation and characterization of anthramycin, a new antitumor antibiotic," *J. Am. Chem. Soc.*, 87, 5791-5793 (1965).

Leimgruber, W. et al., "The structure of anthramycin," *J. Am. Chem. Soc.*, 87, 5793-5795 (1965).

Leimgruber, W. et al., "Total synthesis of anthramycin," *J. Am. Chem. Soc.*, 90, 5641-5643 (1968).

Lescrinier, T. et al., "DNA-Binding Ligands from Peptide Libraries Containing Unnatural Amino Acids," *Chem. Eur. J.*, 4, 3, 425-433 (1998).

Lewis A.D. et al., "Glutathione and glutathione-dependent enzymes in ovarian adenocarcinoma cell lines derived from a patient before and after the onset of drug resistance: intrinsic differences and cell cycle effects," *Carcinogenesis*, 9, 1283-1287 (1988).

Lipshutz, B.H. et al., "Pd(II) Catalyzed Acetal/Ehtal Hydrolysis/Exchange Reactions," Tetrahedron Lett. (1985) 26(6):705-708.

Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026; and Abstract No. 51709.

Mhaka et al., "A 5-fluorodeoxyuridine prodrug as targeted therapy for prostate cancer," Biorg. Med. Chem. Lett. (2002) 12(17:2459-2461.

Mischiati, C. et al., "Binding of hybrid molecules containing pyrrolo [2,1-c][1,4]benzodiazepine (PBD) and oligopyrrole carriers to the human immunodeficiency type 1 virus TAR-RNA," Biochem. Pharmacol. (2004)67(3):401-410.

Mizushima, S. and Nagata, S., "pEF-BOS, a powerful mammalian expression vector," *Nucl. Acids Res.*, 18, 5322 (1990).

Monks, A. et al., "Feasibility of High-Flux Anticancer Drug Screen Using a Diverse Panel of Cultured Human Tumor Cell Lines," *Journal of National Cancer Institute*, 83, 757-766 (1991).

Moran, E.J. et al., "Novel Biopolymers for Drug Discovery: Biopolymers", *Peptide Science*, John Wiley and Sons, 37: 213-19 (1995).

Morgan, R.A. and Anderson, W.F., "Human Gene Therapy," *Annu. Rev. Biochem.*, 62, 191-217 (1993).

Mori, M. et al., "Total syntheses of prothracarcin and tomaymycin by use of palladium catalyzed carbonylation," Tetrahedron (1986) 42(14):3793-3806.

Mosmann, T., "Rapid Colorimetric Assay for Cellular Growth and Survival: Application to Proliferation and Cytotoxicity Assays," *J. Immunological Methods*, 65, 55-63 (1983).

Mountzouris, J.A. et al., "Comparison of a DSB-120 DNA interstrand cross-linked adduct with the corresponding bis-Tomamycin adduct," J. Med. Chem. (1994) 37:3132-3140.

Mullen, D.G. and Barany, G., "A New Fluoridolyzable Anchoring Linkage for Orthogonal Solid-Phase Peptide Synthesis: Design, Preparation, and Application of the N-(3 or 4)-[[4-(Hydroxymethyl) phenoxy]-tert-butylphenylsiyl]phenyl Pentanedioic Acid Monoamide (Pbs) Handle", *J. Org. Chem.*, 53, 5240-5248 (1988).

Nagasaka, T. and Koseki, Y, "Stereoselective Synthesis of Tilivalline," *Journal of Organic Chemistry*, vol. 63, No. 20, 6797-6801 (1998).

Nagasaka, T. et al., "Stereoselective Synthesis of Tilivalline," *Tetrahedron Letters*, 30:14, 1871-1872 (1989).

Nicolaou, K.C. et al., "Designed Enediynes: A New Class of DNA-Cleaving Molecules with Potent and Selective Anticancer Activity," *Science*, 256, 1172-1178 (1992).

Niculescu-Duvaz, D. et al., "Self-immolative nitrogen mustard prodrugs for suicide gene therapy," J. Med. Chem. (1998) 41(26):5297-5309.

Nielson, P.E. et al., "Sequence-Selective Recognition of DNA by Strand Displacement with a Thymine-Substituted Polyamide," *Science*, 254, 1497-1500 (1991).

O'Neil, I.A., et al., "The Synthesis of Functionalized Pyrrolo-[2,1-c][1,4]-Benzodiazepines," *Synlett*, 75-78 (1997).

O'Neil, Chemical Abstract No. 171573p, "The synthesis of Functionalized Pyrrolo-[2,1-c][1,4]-Benzodiazepines", *Chemical Abstracts*, vol. 126, No. 13, 618 (1997).

O'Neil, I.A. et al., "DPPE: A Convenient Replacement for Triphenylphosphine in the Staudinger and Mitsunobu Reactions", *Tetrahedron Letters*, vol. 39, No. 42, 7787-7790 (1998).

Paikoff, S.J. et al., "The Solid Phase Synthesis of N-Alkylcarbamate Oligomers", *Tetrahedron Letters*, 37, No. 32: 5653-5656 (1996).

Pillai, V.N.R., "Photoremovable protecting groups in organic chemistry," *Synthesis*, 1-26 (1980).

Ram, Z. et al., "In Situ Retroviral-mediated Gene Transfer for the Treatment of Brain Tumors in Rats," *Cancer Research*, 53, 83-88 (1993).

Rawal, V.H. et al., "Photocyclization Strategy for the Synthesis of Antitumor Agent CC-1065: Synthesis of Dideoxy PDE-I and PDE-II. Synthesis of Thiophene and Furan Analogues of Dideoxy PDE-I and PDE-II," *J. Org. Chem.*, 52, 19-28 (1987).

Reddy et al., "Design, synthesis and in vitro cytotoxicity studies of novel pyrrolo[2,1-c][1,4]benzodiazepine (PBD)-polyamide conjugates and 2,2'-PBD dimers," Anti-Cancer Drug Design (2000) 15(3):225-228.

Regula, J. et al., "Photosensitisation and photodynamic therapy of oesophagael, duodenal and colorectal tumours using 5-aminoleavulic acid induced photoporphyrin IX-a pilot study," *Gut*, 36, 67-75 (1995).

Sagnou, M.J. et al., "Design and Synthesis of Novel Pyrrolobenzodiazepine (PDB) Prodrugs for ADEPT and GDEPT," *Bioorganic & Medicinal Chemistry Letters*, 10, 2083-2086 (2000).

Saha, A.K. et al., "Diisopropylsilyl-Linked Oligonucleotide Analogs: Solid-Phase Synthesis and Physiocochemical Properties," *J. Org. Chem.*, 58, 7827-7831 (1993).

Satyam, A. et al., "Design, Synthesis, and Evaluation of Latent Alkylating Agents Activated by Glutathione S-Transferase," *J. Med. Chem.*, 39, 1736-1747 (1996).

Shimizu, K et al., "Prothracarcin, a Novel Antitumor Antibiotic," *J. Antibiotics*, 35, 972-978 (1982).

Simon, R.J. et al., "Peptoids: A Modular Approach to Drug Discovery", *Proc. Natl. Acad. Sci*. USA,89:9367-9371 (1992).

Smellie, M. et al., "Cellular pharmacology of novel C8-linked anthramycin-based sequence-selective DNA minor groove cross-linking agents," Br. J. Cancer (1994) 70:48-53.

Smellie, M. et al., "Sequence selective recognition of duplex DNA through covalent interstrand cross-linking," Biochem. (2003) 42:8232-8239.

Soth, M.J. and Nowick, J.S., "Unnatural oligomers and unnatural oligomer libraries", *Curr. Opin. Chem. Biol.*, 1:120-129 (1997).

Star, W.M., "Light delivery and light dosimetry for photodynamic therapy," *Lasers in Medical Science*, 5:107-113 (1990).

Suggs, J.W. et al., "Synthesis and structure of anthramycin analogs via hydride reduction of dilactams," *Tetrahedron Letters*, 26, No. 40, 4871-4874 (1985).

Takeuchi, T. et al., "Neothramycins A and B, New Antitumor Antibiotics," *J. Antibiotics*, 29, 93-96 (1976).

Tew, K.D. and Clapper, M.L., "Glutathione-S-transferase and anticancer drug resistance," *Mechanism of Drug Resistance in Neoplastic Cells*, Woolley, P.V. and Tew, K.D., Eds, Academic Press: Sand Diego, CA 141-159 (1988).

Thurston, D.E. and Thompson, A.S., "The molecular recognition of DNA," *Chem. Brit.*, 26, 767-772 (1990).

Thurston, D.E. and Bose, D.S., "Synthesis of DNA-Interactive Pyrrolo[2,1-c][1,4]benzodiazepines," *Chem. Rev.*, 94:433-465 (1994).

Thurston, D. E., "Advances in the study of Pyrrolo[2,1-c][1,4] benzodiazepine (PBD) Antitumour Antibiotics", *Molecular Aspects of Anticancer Drug-DNA Interaction*, Niedle, S. and Waring, M.J., Eds.; Macmillan Press Ltd, 1:54-88 (1993).

Thurston, D.E. et al., "Effect of A-ring modifications on the DNA-binding behavior and cytotoxicity of pyrrolo[2,1-c][1,4]benzodiazepines", *Journal of Medicinal Chemistry*, 42:1951-1964 (1999).

Thurston, D.E. et al., "Synthesis of Sequence-selective C8-linked Pyrrolo [2,1-c][1,4] Benzodiazepine DNA Interstrand Cross-linking Agent," *J. Org. Chem.*, 61:8141-8147 (1996).

Thurston, D.E. et al., "Synthesis of a novel GC-specific covalent-binding DNA affinity-cleavage agent based on pyrrolobenzodiazepines (PBDs)," Chemical Communications, 563-565 (1996).

Thurston, D.E., "Nucleic acid targeting: therapeutic strategies for the 21st century," Brit. J. Cancer (1999) 80(1):65-85.

Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.

Tsunakawa, M. et al., "Porothramycin, a new antibiotic of the anthramycin group: Production, isolation, structure and biological activity," *J. Antibiotics*, 41:1366-1373 (1988).

Umezawa, H. et al., Chemical Abstract No. 4427a, "Mazethramycins" *Chemical Abstracts*, vol. 90, No. 1, 428 (1979).

Umezawa, H. et al., "Mazethramycins," *SciFinder Scholar*, 2-3 (2002).

Wells, G. et al., "Pyrrolobenzodiazepine-polyamide libraries: synthesis and DNA binding selectivity," Proc. Am. Assoc. Canc. Res. (2003) 44:85-86, #452.

Wermuth et al., "Molecular Variations Based on Isosteric Replacements," The Practice of Medicinal Chemistry, Chapter 13 (1996) 203-237.

Williams, M.A. et al., "Synthesis of conformationally constrained DTPA analogues. Incorporation of the ethylenediamine units as aminopyrrolidines," J. Org. Chem. (1994) 59(13):3616-3625.

Wilson, S.C. et al., "Design and Synthesis of a Novel Epoxide-Containing Pyrrolo[2,1-c][1,4]benzodiazepine (PBD) via a New Cyclization Procedure," *Tetrahedron Letters*, 36, No. 35, 6333-6336 (1995).

Wilson, S.C. et al., "Design, Synthesis, and Evaluation of a Novel Sequence-Selective Epoxide-Containing DNA Cross-Linking Agent Based on the Pyrrolo[2,1-*c*][1,4]benzodiazepine System", *J. Med. Chem.* 42:4028-4041 (1999).

Zuckerman, R.N. et al., "Discovery of Nanomolecular Ligands for 7-Transmembrane G-Protein-Coupled Receptors from a Diverse N-(Substituted) glycine Peptoid Library", *J. Med. Chem.*, 37:2678-2685 (1994).

* cited by examiner

SYNTHESIS OF PROTECTED PYRROLOBENZODIAZEPINES

CROSS-REFERENCE TO RELATED APPLICATIONS

This patent application is a national stage filing under 35 U.S.C. 371 of International Application No. PCT/GB2004/003873, filed on Sep. 10, 2004, which claims foreign priority benefits to United Kingdom Application No. 0321295.8, filed Sep. 11, 2003.

The present application relates to methods of making pyrrolobenzodiazepine (PBD) compounds, and in particular, PBDs having a N-10 protecting group, as well as intermediates in these methods.

BACKGROUND

A large number of both synthetic and naturally occurring low molecular weight ligands are known that interact with DNA via a number of different mechanisms, including covalent or non-covalent interaction in the minor or major grooves, intercalation between base pairs or other types of non-specific interactions.

A particular class of compounds which interacts with the minor groove are the pyrrolobenzodiazepines (PBDs). PBDs have the ability to recognise and bond to specific sequences of DNA; the most preferred sequence is PuGPu (Purine-Guanine-Purine). The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski et al., 1987 *J. Antibiotics*, 40, 145-148), chicamycin (Konishi et al., 1984 *J. Antibiotics*, 37, 200-206), DC-81 (Japanese Patent 58-180 487; Thurston et al., 1990, *Chem. Brit.*, 26, 767-772; Bose et al., 1992 *Tetrahedron*, 48, 751-758), mazethramycin (Kunimoto et al., 1980 *J. Antibiotics*, 33, 665-667), neothramycins A and B (Takeuchi et al., 1976 *J. Antibiotics*, 29, 93-96), porothramycin (Tsunakawa et al., 1988 *J. Antibiotics*, 41, 1366-1373), prothracarcin (Shimizu et al., 1982 *J. Antibiotics*, 35, 972-978; Langley and Thurston, 1987 *J. Org. Chem.*, 52, 91-97), sibanomicin (DC-102)(Hara et al., 1988 *J. Antibiotics*, 41, 702-704; Itoh et al., 1988 *J. Antibiotics*, 41, 1281-1284), sibiromycin (Leber et al., 1988 *J. Am. Chem. Soc.*, 110, 2992-2993) and tomamycin (Arima et al., 1972 *J. Antibiotics*, 25, 437-444).

PBDs are of the general structure:

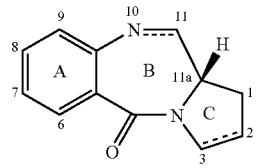

They differ in the number, type and position of substituents, in both their aromatic A rings and pyrrolo C rings, and in the degree of saturation of the C ring. There is either an imine (N=C), carbinolamine (NH—CH(OH)) or a carbinolamine methyl ether (NH—CH(OMe)) at the N10-C11 position which is the electrophilic centre responsible for alkylating DNA. These forms may exist in equilibrium in solution. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, 1975 In *Antibiotics III*. Springer-Verlag, New York, pp. 3-11; Hurley and Needham-VanDevanter, 1986 *Acc. Chem. Res.*, 19, 230-237). Their ability to form an adduct in the minor groove enables them to interfere with DNA processing, hence their use as antitumour agents.

The present inventors have previously disclosed that PBDs can be employed as prodrugs by protecting them at the N10 position with a nitrogen protecting group which is removable in vivo (WO 00/12507). Many of these protecting groups are carbamates, and are, for example, of the structure:

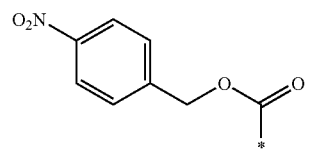

where * indicates the attachment point to the N10 atom of the PBD. These protecting groups are described as being added to the compound at two different stages in the synthesis route. One stage is addition of the corresponding chloroformate to a precursor structure as follows, which precursor is then cyclised to form the desired final compound:

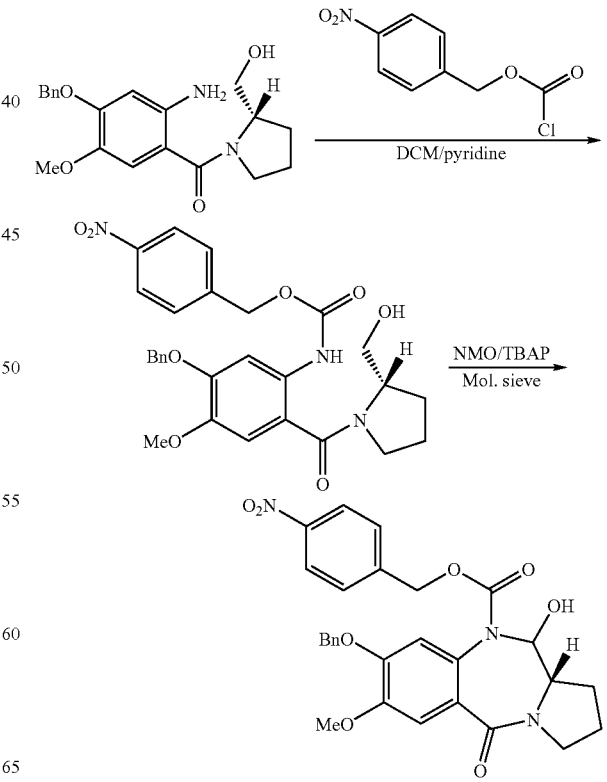

An alternative route discussed involves adding the corresponding chloroformate to a carboxy aniline precursor of the starting material in the above route.

These routes employ a chloroformate reacting with an (aromatic) amine to form the carbamate. The present inventors have discovered that the use of the chloroformate has disadvantages, and have therefore developed an alternative synthesis route, which does not employ a chloroformate.

SUMMARY OF THE INVENTION

Accordingly, a first aspect of the present invention provides a method of synthesis of a compound of formula (I):

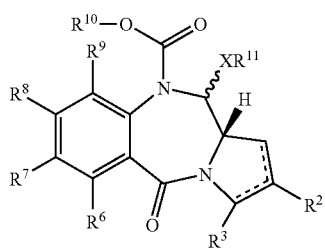

(I)

comprising the step of either:

(a) reacting a compound of formula (II) with a compound of formula (III) to yield a compound of formula (IV):

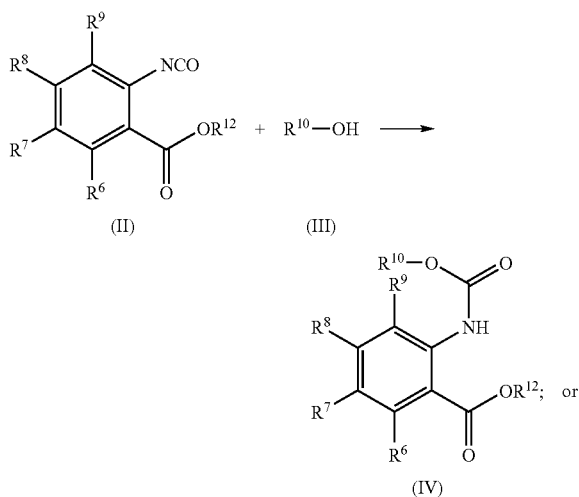

(b) reacting a compound of formula (V) with a compound of formula (III) to yield a compound of formula (VI):

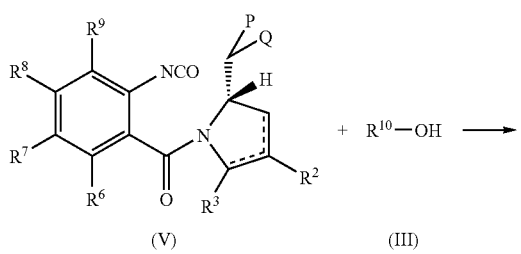

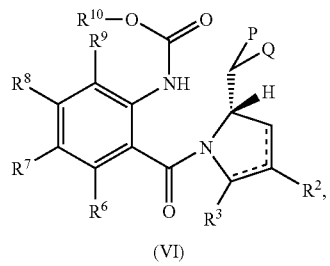

(VI)

wherein the dotted lines indicate the optional presence of a double bond between C1 and C2 or C2 and C3;

$R^2$ and $R^3$ are independently selected from —H, —OH, =O, =CH$_2$, —CN, —R, OR, =CH—R, O—SO$_2$—R, CO$_2$R and COR;

$R^6$, $R^7$ and $R^9$ are independently H, R, OH, OR, SH, SR, NH$_2$, NHR, NRR', nitro, Me$_3$Sn and halo;

$R^8$ is either selected from H, R, OH, OR, SH, SR, NH$_2$, NHR, NRR', nitro, Me$_3$Sn and halo or the compound is a dimer with each monomer being the same of different and being of the relevant formula, where the $R^8$ groups of each monomer form together a bridge having the formula —X—R"—X—, where R" is a $C_{3-12}$ alkylene group, which chain may be interrupted by one or more heteroatoms, e.g. O, S, NH, and/or aromatic rings, e.g. benzene or pyridine, and each X is independently selected from O, S and NH;

$R^{10}$ is such that $R^{10}$—OC(=O)— forms a nitrogen protecting group;

$R^{11}$ is either H or R;

$R^{12}$ is an optionally substituted $C_{1-4}$ alkyl group;

P and Q are such that —CPQ is a masked aldehyde group;

wherein R and R' are independently selected from optionally substituted $C_{1-20}$ alkyl, $C_{3-20}$ heterocyclyl, and $C_{5-20}$ aryl.

Reaction Conditions

The reactions above should be carried in an anhydrous and non-hydroxylic organic solvent, which is preferably non-polar. Suitable solvents include anhydrous dichloromethane and anhydrous toluene. The reaction should be carried out in the presence of a base is present, and suitable bases include pyridine or TEA. The reaction may be carried out at 0° C., or at a higher temperature to increase the rate of reaction.

Further Reaction Steps

If the method of synthesis of the first aspect of the invention comprises step (a), then the synthesis of the compound of formula (I) from the compound of formula (IV) will be according to the following scheme:

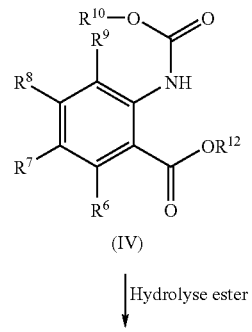

(IV)

↓ Hydrolyse ester

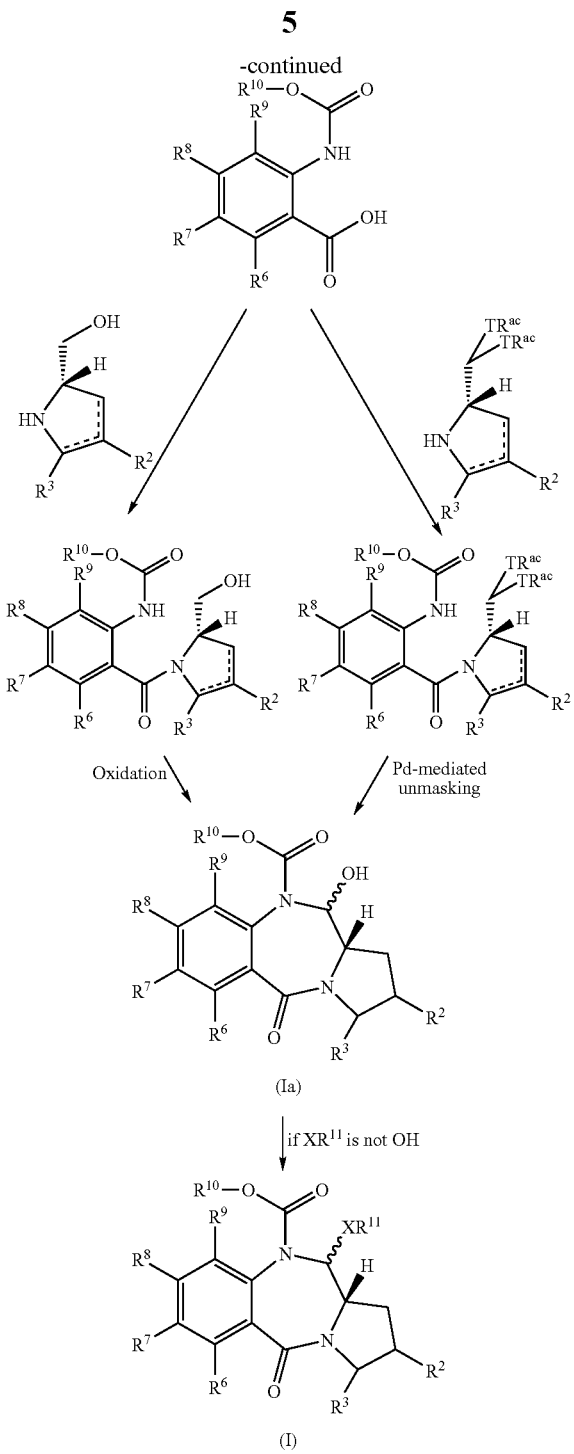

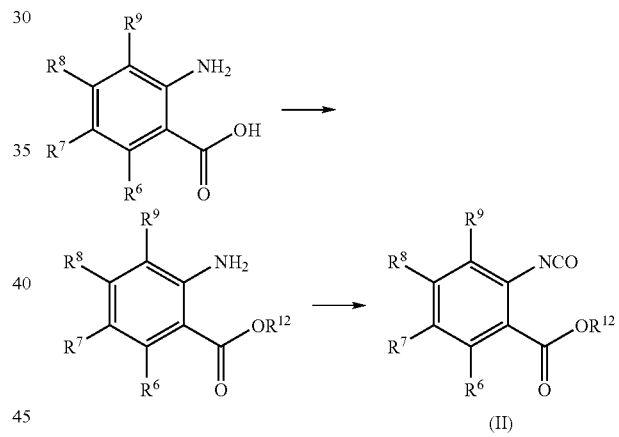

wherein T is O or S, and each $R^{ac}$ is independently selected from $C_{1-10}$ alkyl or together can be a $C_{1-3}$ alkylene group.

Thus the synthesis further comprise the following steps:
(i) hydrolysis of the ester —C(=O)$OR^{12}$;
(ii) (a) coupling of resulting acid with hydroxymethyl pyrrole, followed by oxidation; or
  (b) coupling of resulting acid with acetalmethyl pyrrole, followed by palladium mediated unmasking; and
(iii) (a) if $XR^{11}$ is $OR^{11}$, direct etherification;
  (b) if $XR^{11}$ is $SR^{11}$, treatment with $R^{11}SH$ and a catalyst, such as a Lewis Acid, e.g. $Al_2O_3$)
(c) if $XR^{11}$ is $NHR^{11}$, treatment with $R^{11}NH$ and a catalyst, such as a Lewis Acid, e.g. $Al_2O_3$)

The ester hydrolysis is usually carried out under mild conditions, for example at 0° C. with lithium hydroxide or under non-basic conditions, if the carbamate is sensitive to these. In this situation suitable $R^{12}$ groups would include allyl, butyl and benzyl.

The coupling reaction is preferably carried out under mild conditions, with preferred conditions being DCC or HOBt in DCM at low temperature. Oxalyl chloride and thionyl chloride may be used, but are less preferred.

Oxidation of the deprotected primary alcohols provokes spontaneous PBD B-ring closure. A number of oxidizing agents/conditions can be employed to achieve ring closure including; Swern Oxidation, $SO_3$-Pyridine/DMSO, pyridinium dichromate, TPAP/NMO, Dess-Martin Periodinane and TEMPO-DAIB. The TEMPO/DAIB system is particularly favoured as it does not require rigorous anhydrous conditions, reaction is easily monitored by TLC, and there is no evidence of over-oxidation to the PBD dilactam species.

The palladium mediated demasking can be carried out under literature conditions, such as using bisacetonitrile palladium chloride, $(CH_3CN)_2PdCl_2$, in acetone (Lipshutz, B. H., et al., *Tetrahedron Letters*, 26, 705 (1985)).

The compound of formula (II) can be synthesised according to the following scheme:

Thus the synthesis further comprise the following steps:
(i) esterification, by reaction with $R^{12}OH$; and
(ii) reaction with triphosgene to form isocynate.

The esterification is carried out under normal conditions. Often the ester is commercially available itself.

The conversion to the isocyanate can be carried out by the action of phosgene, trichloromethyl chloroformate or triphosgene, of which triphosgene is the preferred agent as is an easy to handle crystalline solid rather than a toxic gas. The reaction should be carried in an anhydrous and non-hydroxylic organic solvent, which is preferably non-polar. Suitable solvents include anhydrous dichloromethane and anhydrous toluene. The reaction may be carried out at room temperature, and is conveniently monitored by infrared spectroscopy at about 2260 $cm^{-1}$.

If the method of synthesis of the first aspect of the invention comprises step (b), then the synthesis of the compound of formula (I) from the compound of formula (VI) will be according to the following scheme:

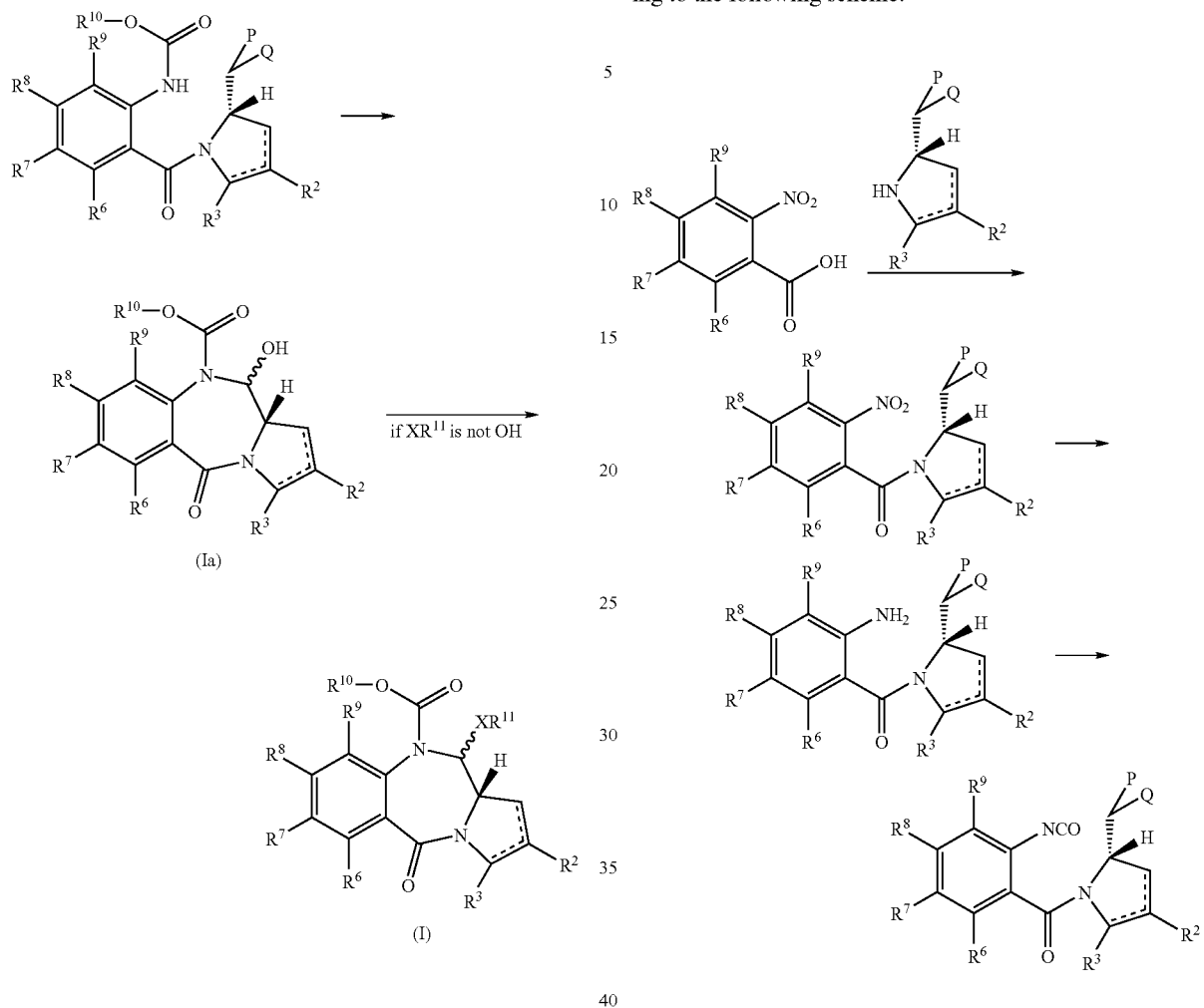

Thus the synthesis comprises the following steps:

(i) (a) if —CPQ represents a protected alcohol group, deprotection followed by oxidation; or (b) if —CPQ represents an acetal or thioacetal, palladium mediated unmasking; and (ii) (a) if $XR^{11}$ is $OR^{11}$, direct etherification;

(b) if $XR^{11}$ is $SR^{11}$, treatment with $R^{11}SH$ and a catalyst, such as a Lewis Acid, e.g. $Al_2O_3$)

(c) if $XR^{11}$ is $NHR^{11}$, treatment with $R^{11}NH$ and a catalyst, such as a Lewis Acid, e.g. $Al_2O_3$).

The hydroxyl protecting groups (if present) must be removed to allow B-ring cyclization to take place. Removal is under standard conditions. For example, an acetate protecting group can be removed under extremely mild conditions with potassium carbonate. A silyl ether protecting group can be removed by fluoridolysis using TBAF or with mild acid. If these conditions are unsuitable for a particular carbamate, alternative hydroxyl protecting groups can be selected as long as they are capable of surviving the reduction of the nitro group.

The conditions for the remaining reactions are as described above in relation to the first method.

The compound of formula (IV) can be synthesised according to the following scheme:

Thus the synthesis comprises the following steps:

(i) (a) coupling of acid with hydroxymethylpyrrole; or (b) coupling of acid with acetalmethylpyrrole;

(ii) reduction of aromatic nitro group to form aromatic amine group; and (ii) reaction with triphosgene to form isocynate.

Commercially available nitrobenzoic acids are converted to acid chlorides and coupled to pyrrolidinemthanol and its derivatives under literature conditions. Free hydroxyl groups may be protected as silyl ethers or acetates (other protectings groups, including acetals such as MEM or MOM, can be employed as long as they are stable to the conditions requires to reduced the aromatic nitro group) in order to prevent the formation of a bridging carbamate in the isocyanate formation step.

The reduction of the nitro group can be carried out under standard conditions. Preferred methods include hydrogenation over a palladium on charcoal catalyst in a Parr hydrogenator, and using sodium dithionite, tin(II) chloride or Raney Nickel and hydrazine, depending on the requirements of the hydroxyl protecting group.

The isocyante forming step is carried out as described above.

A second aspect of the invention is a compound of formula (IV):

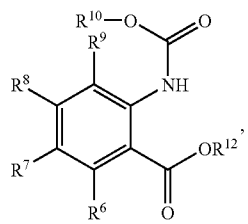

(IV)

wherein $R^6$, $R^7$, $R^8$, $R^9$, $R^{10}$ and $R^{12}$ are as defined in the first aspect of the invention.

A third aspect of the present invention is a compound of formula (VI):

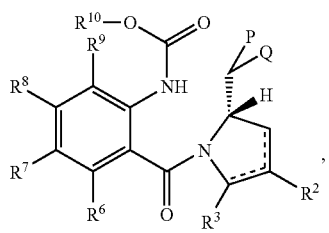

(VI)

wherein $R^2$, $R^3$, $R^6$, $R^7$, $R^8$, $R^9$, $R^{10}$, P and Q are as defined in the first aspect of the invention, and the dotted lines indicate the optional presence of a double bond between C1 and C2 or C2 and C3.

DEFINITIONS

Masked aldehyde group (—CPQ): The term masked aldehyde group pertains to a group which can be chemically converted into an aldehyde group, and includes in particular, a protected alcohol group (—CH$_2$OProt), wherein the alcohol protecting group is orthogonal to the nitrogen protecting group, acetal groups (—C(ORac)$_2$), thioacetal groups (—C(SR$^{ac}$)$_2$), where each R$_{ac}$ can be independently selected from C$_{1-10}$ alkyl or together can be a C$_{1-3}$ alkylene group.

Alcohol Protecting Group: This term pertains to a group which is removable leave an alcohol group, without affecting the remainder of the compound to which the alcohol group is attached. Of particular interest are ethers and esters, numerous examples of which are described in Greene and Wuts, "Protective Groups in Organic Synthesis", 3$^{rd}$ edition, John Wiley & Sons (1999), which is incorporated herein by reference. Examples include ethers, in particular silyl ethers (e.g. tert-butyl-dimethyl-silyl ether), esters, for examples acetates and carbonates.

Orthogonal: Protecting groups are orthogonal to one another, if one protecting group can be removed from a molecule in which the other protecting group is present, without the other protecting group being removed. For example, the alcohol protecting group acetate is orthogonal to the nitrogen protecting group Teoc, and the alcohol protecting group TBDMS is orthogonal to the nitrogen protecting group benzyloxy carbamate.

Nitrogen Protecting Group: This term pertains to a group which is removable from the N10 position of the PBD moiety to leave an N10-C11 imine bond. This application is only concerned with those nitrogen protecting groups which are carbamate, i.e. those which have the structure:

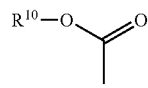

The nature of R$^{10}$ can vary widely, and is chosen dependent on the conditions by which the whole group is eliminated from the molecule. A large number of suitable groups are described in Greene and Wuts, "Protective Groups in Organic Synthesis", 3$^{rd}$ edition, John Wiley & Sons (1999), which is incorporated herein by reference. These groups include many well know groups such as fmoc (9-fluorenylmethylcarbamate), Troc (2,2,2-trichloroethyl carbamate) and Alloc (allyl carbamate) which can be removed under varying conditions. Also described are carbamate based nitrogen protecting groups which can be cleaved photolytically, such as o-nitrobenzyl carbamate and Nvoc (6-nitroveratryl carbamate).

Also of interest are groups which can be cleaved by the action of enzymes. These include the following:

| Group | Removable by |
|---|---|
| 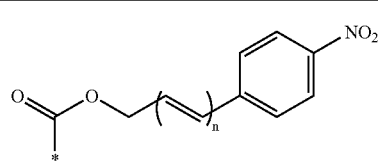 n = 0 to 3 | nitroreductase |

| Group | Removable by |
|---|---|
| [structure: phenylsulfonyl ethyl carbonate] | Glutathione/glutathione transferase |
| [cephalosporin structure with R groups: 2-thienyl, benzyl, butyl] | β-lactamase |
| [cephalosporin sulfoxide structure with thienylacetamide] | β-lactamase |
| [galactose-phenyl-CH2-O-C(O)- structure] | α-galactosidase |
| [benzyl carbonate with glutamate-carbamate structure; Q = NH, O] | carboxypeptidase |

These groups, and others, are described in, for example, Jungheim, L. and Shepherd, T., *Chem. Rev.*, 94, 1553-1566 (1994), WO 00/64864 and Niculescu-Duvaz, D., et al., *J. Med. Chem.*, 41, 5297-5309 (1998).

Further enzyme labile groups include the following:

| Group | Removable by |
|---|---|
| 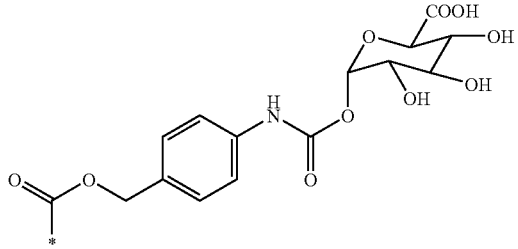 | β-Glucuronidase |
| 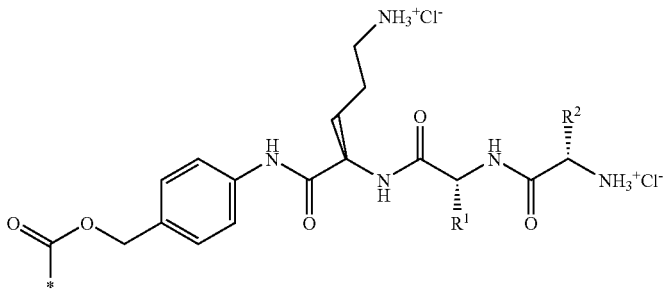<br>$R^1$ & $R^2$ selected from optionally substituted $C_{1-4}$ alkyl<br>(e.g. methyl, iso-propyl, benzyl) | Plasmin<br>(see de Groot, F. M. H., et al., J. Med. Chem., 43, 3093-3102 (2000) & Groot, F. M. H., et al., Bioorganic & Medicinal Chem. Lett., 12, 2371-2376 (2002) |
| 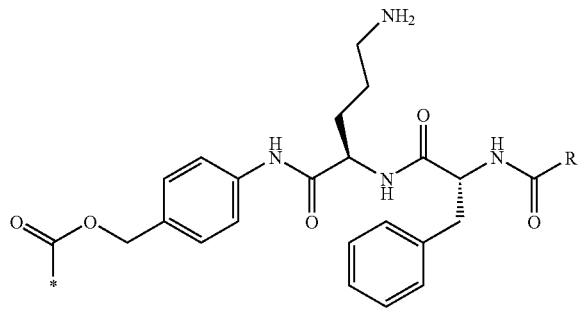<br>R is, for example,<br>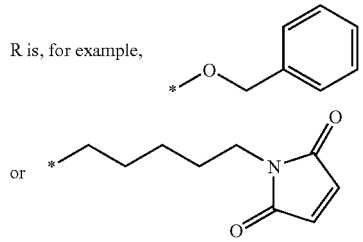<br>or 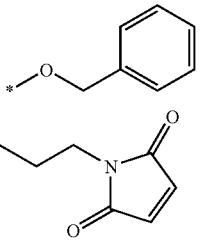 | Cathepsin B<br>(see Duboschik, G. M., et al., Bioorganic & Medicinal Chem. Lett., 8, 3341-3346 and 3347-3352 (1998) |
| 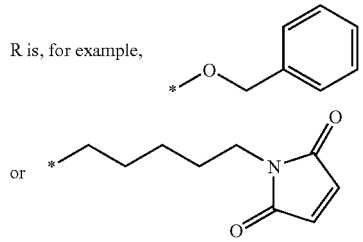<br>where n is 0 to 3 | Prostate Specific Antigen<br>(see Garsky, V. M., et al., J. Med. Chem., 44, 4216-4224 (2001); Mhaka, A., et al., Bioorganic & Medicinal Chem. Lett., 12, 2459-2461 (2002); Jakobsen, C. M., et al., J. Med. Chem., 44, 4696-4703 (2001)) |

Prodrugs with such protecting groups are also reviewed Dubowchik, G. M. and Walker, M. A., *Pharmacology & Therapeutics*, 83, 67-123 (1999).

A number of nitrogen protecting groups (including some of the enzyme labile groups discussed above) can be classed as containing a 'self-immolative linker'. Such groups usually has a structure:

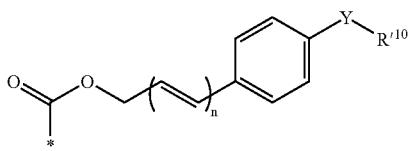

where Y is NH or O, n is 0 to 3 and $R'^{10}$ is such that the whole moiety is a nitrogen protecting group (and may be defined as for $R^{10}$ below). The self-immolative linker will allow for release of the protected compound when a remote site is activated, proceeding along the lines shown below (for n=0):

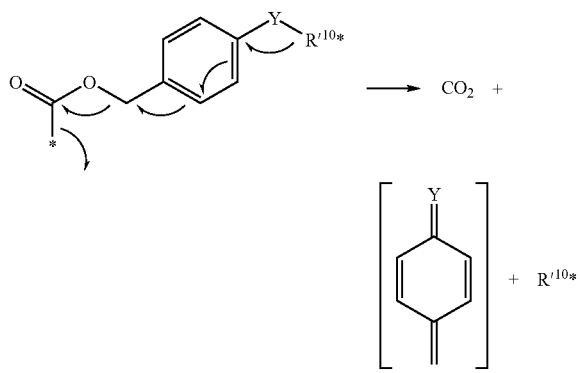

These groups have the advantage of separating the site of activation form the compound being protected.

A further class of nitrogen protecting groups are those where $R^{10}$ essentially forms a cleavable link to another moiety, whether it be physical in nature, for example a solid support, or biological in nature. Examples of these protecting groups are disclosed in WO 00/12509, and include:

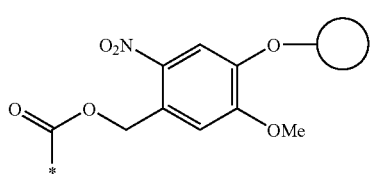

where O represents a resin bead.

The $R^{10}$ group can be described as an optionally substituted $C_{1-30}$ alkyl group, $C_{3-30}$ heterocylyl group or a $C_{5-30}$ aryl group or a divalent version of one of these groups linked to another moiety. It is preferred that $R^{10}$ is not a silane group or is substituted by a silyl group (e.g. —$CH_2$—$Si(Me)_3$).

The present invention allows the synthesis of N-10 protected PBD compounds where the appropriate chloroformate is not available or is unstable. This for example applies to the Moz (methoxybenzyl carbamate) group which cannot be introduced via the chloroformate as it is too unstable, and other derivatives such as Moz-ON are not sufficiently active to react with a PBD-precursor aniline group. However, the p-methoxybenzyl alcohol is commercially available and reacts smoothly with the isocyanate to give the Moz carbamate (see examples, compound 17). The case of the Teoc carbamate reinforces the point; again the required chloroformate is not very stable and not commercially available. A p-nitrophenyl carbonate derivative of Teoc is available but, again, is not sufficiently active to protect an aromatic amine such as compound 5. Trimethylsilylethanol is commercially available and reacts with isocyanates to afford the Teoc carbamate in good yields (see examples, compound 18).

The method of the invention is particularly useful for complex protecting groups, such as those shown in the examples as alcohols 35 and 42. Such protecting groups are required to prepare PBD prodrugs for ADEPT approaches to cancer chemotherapy, and the alcohols are not commercially available and give rise to extremely unstable chloroformates. However, these alcohols react with isocyanates to furnish carbamates in moderate to good yields.

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g., partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$ alkyl" as used herein, pertains to an alkyl group having from 1 to 4 carbon atoms. Examples of groups of alkyl groups include $C_{1-4}$ alkyl ("lower alkyl"), $C_{1-7}$ alkyl, $C_{1-20}$ alkyl and $C_{1-30}$ alkyl. Note that the first prefix may vary according to other limitations; for example, for unsaturated alkyl groups, the first prefix must be at least 2; for cyclic and branched alkyl groups, the first prefix must be at least 3; etc.

Examples of saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl" as used herein, pertains to an alkyl group having one or more carbon-carbon double bonds. Examples of groups of alkenyl groups include $C_{2-4}$ alkenyl, $C_{2-7}$ alkenyl, $C_{2-20}$ alkenyl.

Examples of unsaturated alkenyl groups include, but are not limited to, ethenyl (vinyl, —$CH=CH_2$), 1-propenyl (—$CH=CH$—$CH_3$), 2-propenyl (allyl, —$CH$—$CH=CH_2$), isopropenyl (1-methylvinyl, —$C(CH_3)=CH_2$), butenyl ($C_4$), pentenyl ($C_5$), and hexenyl ($C_6$).

Alkynyl: The term "alkynyl" as used herein, pertains to an alkyl group having one or more carbon-carbon triple bonds. Examples of groups of alkynyl groups include $C_{2-4}$ alkynyl, $C_{2-7}$ alkynyl, $C_{2-20}$ alkynyl.

Examples of unsaturated alkynyl groups include, but are not limited to, ethynyl (ethinyl, —$C\equiv CH$) and 2-propynyl (propargyl, —$CH_2$—$C\equiv CH$).

Cycloalkyl: The term "cycloalkyl" as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g., partially unsaturated, fully unsaturated), which moiety has from 3 to 20 carbon atoms (unless otherwise specified), including from 3 to 20 ring atoms. Thus, the term "cycloalkyl" includes the sub-classes cycloalkyenyl and cycloalkynyl. Preferably, each ring has from 3 to 7 ring atoms. Examples of groups of cycloalkyl groups include $C_{3-30}$ cycloalkyl, $C_{3-20}$ cycloalkyl, $C_{3-10}$ cycloalkyl, $C_{3-7}$ cycloalkyl.

Examples of cycloalkyl groups include, but are not limited to, those derived from:

saturated monocyclic hydrocarbon compounds: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds: thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds: camphene ($C_{10}$), limonene ($C_{10}$), pinene ($C_{10}$);

polycyclic hydrocarbon compounds having an aromatic ring: indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Heterocyclyl: The term "heterocyclyl" as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$ heterocyclyl" as used herein, pertains to a heterocyclyl group having 5 or 6 ring atoms. Examples of groups of heterocyclyl groups include $C_{3-30}$heterocyclyl, $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$heterocyclyl, $C_{5-10}$heterocyclyl, $C_{3-7}$heterocyclyl, $C_{5-7}$ heterocyclyl, and $C_{5-6}$ heterocyclyl.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranose, and pyranoses ($C_6$), such as allopyranose, altropyranose, glucopyranose, mannopyranose, gulopyranose, idopyranose, galactopyranose, and talopyranose.

Aryl: The term "aryl" as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl" as used herein, pertains to an aryl group having 5 or 6 ring atoms. Examples of groups of aryl groups include $C_{3-30}$aryl, $C_{3-20}$ aryl, $C_{5-20}$ aryl, $C_{5-15}$ aryl, $C_{5-12}$ aryl, $C_{5-10}$ aryl, $C_{5-7}$ aryl, $C_{5-6}$ aryl, $C_5$ aryl, and $C_6$ aryl.

The ring atoms may be all carbon atoms, as in "carboaryl groups". Examples of carboaryl groups include $C_{3-20}$ carboaryl, $C_{5-20}$ carboaryl, $C_{5-15}$ carboaryl, $C_{5-12}$ carboaryl, $C_{5-10}$ carboaryl, $C_{5-7}$ carboaryl, $C_{5-6}$ carboaryl and $C_6$ carboaryl.

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g., 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of heteroaryl groups include $C_{3-20}$ heteroaryl, $C_{5-20}$ heteroaryl, $C_{5-15}$ heteroaryl, $C_{5-12}$ heteroaryl, $C_{5-10}$ heteroaryl, $C_{5-7}$ heteroaryl, $C_{5-6}$ heteroaryl, $C_5$ heteroaryl, and $C_6$ heteroaryl.

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heteroaryl groups which comprise fused rings, include, but are not limited to:

$C_9$ heteroaryl groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_1$ heteroaryl groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ heteroaryl groups (with 2 fused rings) derived from benzodiazepine ($N_2$);

$C_{13}$ heteroaryl groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ heteroaryl groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heteroaryl groups which have a nitrogen ring atom in the form of an —NH— group may be N-substituted, that is, as —NR—. For example, pyrrole may be N-methyl substituted, to give N-methylpyrrole. Examples of N-substitutents include, but are not limited to $C_{1-7}$ alkyl, $C_{3-20}$ heterocyclyl, $C_{5-20}$ aryl, and acyl groups.

Heterocyclic groups (including heteroaryl groups) which have a nitrogen ring atom in the form of an —N= group may be substituted in the form of an N-oxide, that is, as —N(→O)= (also denoted —N⁺(→O⁻)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms.

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR¹)(OR²), wherein R¹ and R² are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R¹ and R², taken together with the two oxygen atoms to which they are attached, and the carbon atoms to which they are attached, form a heterocyclic ring having from 4 to 8 ring atoms. Examples of acetal groups include, but are not limited to, —CH(OMe)₂, —CH(OEt)₂, and —CH(OMe)(OEt).

Hemiacetal: —CH(OH)(OR¹), wherein R¹ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR(OR¹)(OR²), where R¹ and R² are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)₂, —C(Me)(OEt)₂, —C(Me)(OMe)(OEt), —C(Et)(OMe)₂, —C(Et)(OEt)₂, and —C(Et)(OMe)(OEt).

Hemiketal: —CR(OH)(OR¹), where R¹ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH₃ (acetyl), —C(=O)CH₂CH₃ (propionyl), —C(=O)C(CH₃)₃ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH₃, —C(=O)OCH₂CH₃, —C(=O)OC(CH₃)₃, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH₃ (acetoxy), —OC(=O)CH₂CH₃, —OC(=O)C(CH₃)₃, —OC(=O) Ph, and —OC(=O)CH₂Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH₃, —OC(=O)OCH₂CH₃, —OC(=O)OC(CH₃)₃, and —OC(=O)OPh.

Amino: —NR¹R², wherein R¹ and R² are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R¹ and R², taken together with the nitrogen atom to which they are attached, form a heterocyclic ring having from 4 to 8 ring atoms. Amino groups may be primary (—NH₂), secondary (—NHR¹), or tertiary (—NHR¹R²), and in cationic form, may be quaternary (—⁺NR¹R²R³). Examples of amino groups include, but are not limited to, —NH₂, —NHCH₃, —NHCH(CH₃)₂, —N(CH₃)₂, —N(CH₂CH₃)₂, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR¹R², wherein R¹ and R² are independently amino substituents, as defined for amino groups. Examples of amido groups include, but are not limited to, —C(=O)NH₂, —C(=O)NHCH₃, —C(=O)N(CH₃)₂, —C(=O)NHCH₂CH₃, and —C(=O)N(CH₂CH₃)₂, as well as amido groups in which R¹ and R², together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR¹R², wherein R¹ and R² are independently amino substituents, as defined for amino groups. Examples of amido groups include, but are not limited to, —C(=S)NH₂, —C(=S)NHCH₃, —C(=S)N(CH₃)₂, and —C(=S)NHCH₂CH₃.

Acylamido (acylamino): —NR¹C(=O)R², wherein R¹ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R² is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH₃, —NHC(=O)CH₂CH₃, and —NHC(=O)Ph. R¹ and R² may together form a cyclic structure, as in, for example, succinimidyl, maleimidyl, and phthalimidyl:

succinimidyl    maleimidyl    phthalimidyl

Aminocarbonyloxy: —OC(=O)NR¹R², wherein R¹ and R² are independently amino substituents, as defined for amino groups. Examples of aminocarbonyloxy groups include, but are not limited to, —OC(=O)NH₂, —OC(=O)NHMe, —OC(=O)NMe₂, and —OC(=O)NEt₂.

Ureido: —N(R¹)CONR²R³ wherein R² and R³ are independently amino substituents, as defined for amino groups, and R¹ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH₂, —NHCONHMe, —NHCONHEt, —NHCONMe₂, —NHCONEt₂, —NMeCONH₂, —NMeCONHMe, —NMeCONHEt, —NMeCONMe₂, and —NMeCONEt₂.

Guanidino: —NH—C(=NH)NH₂.

Tetrazolyl: a five membered aromatic ring having four nitrogen atoms and one carbon atom, Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of imino groups include, but are not limited to, =NH, =NMe, and =NEt.

Amidine (amidino): —C(=NR)NR₂, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH₂, —C(=NH)NMe₂, and —C(=NMe)NMe₂.

Nitro: —NO₂.

Nitroso: —NO.

Azido: —N₃.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH₃ and —SCH₂CH₃.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH₃ and —SSCH₂CH₃.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH₃ and —S(=O)CH₂CH₃.

Sulfone (sulfonyl): —S(=O)₂R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)₂CH₃ (methanesulfonyl, mesyl), —S(=O)₂CF₃ (triflyl), —S(=O)₂CH₂CH₃ (esyl), —S(=O)$_2$ C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a C$_{1-7}$ alkyl group, a C$_{3-20}$ heterocyclyl group, or a C$_{5-20}$ aryl group, preferably a C$_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a C$_{1-7}$ alkyl group, a C$_{3-20}$ heterocyclyl group, or a C$_{5-20}$ aryl group, preferably a C$_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$ alkyl group, a C$_{3-20}$ heterocyclyl group, or a C$_{5-20}$ aryl group, preferably a C$_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$) S(=O)C$_6$H$_5$.

Phosphino (phosphine): —PR$_2$, wherein R is a phosphino substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)2.

Phospho: —P(=O)$_2$.

Phosphinyl (phosphine oxide): —P(=O)R$_2$, wherein R is a phosphinyl substituent, for example, a C$_{1-7}$ alkyl group, a C$_{3-20}$ heterocyclyl group, or a C$_{5-20}$ aryl group, preferably a C$_{1-7}$ alkyl group or a C$_{5-20}$ aryl group. Examples of phosphinyl groups include, but are not limited to, —P(=O) (CH$_3$)$_2$, —P(=O) (CH$_2$CH$_3$)$_2$, —P(=O) (t-Bu)$_2$, and —P(=O) (Ph)$_2$.

Phosphonic acid (phosphono): —P(=O) (OH)$_2$.

Phosphonate (phosphono ester): —P(=O) (OR)$_2$, where R is a phosphonate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$aryl group. Examples of phosphonate groups include, but are not limited to, —P(=O) (OCH$_3$)$_2$, —P(=O) (OCH$_2$CH$_3$)$_2$, —P(=O) (O-t-Bu)$_2$, and —P(=O) (OPh)$_2$.

Phosphoric acid (phosphonooxy): —OP(=O) (OH)2.

Phosphate (phosphonooxy ester): —OP(=O) (OR)$_2$, where R is a phosphate substituent, for example, —H, a C$_{1-7}$ alkyl group, a C$_{3-20}$ heterocyclyl group, or a C$_{5-20}$aryl group, preferably —H, a C$_{1-7}$ alkyl group, or a C$_{5-20}$aryl group. Examples of phosphate groups include, but are not limited to, —OP(=O) (OCH$_3$)$_2$, —OP(=O) (OCH$_2$CH$_3$)$_2$, —OP(=O) (O-t-Bu)$_2$, and —OP(=O) (OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP (OCH$_2$CH$_3$)$_2$, —OP(O-t-Bu)$_2$, and —OP(OPh)$_2$.

Phosphoramidite: —OP(OR$^1$)-NR$^2$$_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N (i-Pr)$_2$.

Phosphoramidate: —OP(=O) (OR$^1$)—NR$^2$$_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O) (OCH$_2$CH$_3$)—N(CH$_3$)$_2$, —OP(=O) (OCH$_2$CH$_3$)—N (i-Pr)$_2$, and —OP(=O) (OCH$_2$CH$_2$CN)—N (i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below.

Examples of linear saturated $C_{3-12}$ alkylene groups include, but are not limited to, —$(CH_2)_n$— where n is an integer from 3 to 12, for example, —$CH_2CH_2CH_2$— (propylene), —$CH_2CH_2CH_2CH_2$— (butylene), —$CH_2CH_2CH_2CH_2CH_2$— (pentylene) and —$CH_2CH_2CH_2CH_2CH_2CH_2CH_2$— (heptylene).

Examples of branched saturated $C_{3-12}$ alkylene groups include, but are not limited to, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—.

Examples of linear partially unsaturated $C_{3-12}$ alkylene groups ($C_{3-12}$ alkenylene, and alkynylene groups) include, but are not limited to, —CH=CH—$CH_2$—, —$CH_2$—CH=$CH_2$—, —CH=CH—$CH_2$—$CH_2$—, —CH=CH—$CH_2$-$CH_2$-$CH_2$—, —CH=CH—CH=CH—, —CH=CH—CH=CH—$CH_2$—, —CH=CH—$CH_2$—, —CH=CH—$CH_2$—$CH_2$—, —CH=CH—$CH_2$—CH=CH—, —CH=CH—$CH_2$—$CH_2$-CH=CH—, and —$CH_2$—C≡C—$CH_2$—.

Examples of branched partially unsaturated $C_{3-12}$ alkylene groups ($C_{3-12}$ alkenylene and alkynylene groups) include, but are not limited to, —$C(CH_3)$=CH—, —$C(CH_3)$=CH—$CH_2$—, —CH=CH—$CH(CH_3)$— and —C≡C—$CH(CH_3)$—.

Examples of alicyclic saturated $C_{3-12}$ alkylene groups ($C_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated $C_{3-12}$ alkylene groups ($C_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

The term "$C_{1-3}$ alkylene" as used herein, is defined in a similar manner to the above group, but with from 1 to 3 carbon atoms.

Solvents

Solvents may conveniently be classified according to one or more of their physical or chemical properties.

For example, solvents may be classified according to their polarity, that is, their permanent dipole moment. Examples of highly polar solvents include dimethylformamide (DMF), dimethylacetamide, and acetonitrile (ACN). Examples of moderately polar solvents include acetone, methanol, tetrahydrofuran (THF), ethyl acetate (AcOEt), and water. Examples of relatively non-polar solvents include diethyl ether, chloroform, and dichloromethane (DCM). Examples of non-polar and virtually non-polar solvents include alkanes, benzene, toluene, and carbon tetrachloride.

Solvents may also be classified as "protic" or "aprotic" according to their proton-exchange properties. Protic solvents accept and/or donate protons. Examples of protic solvents include water, alcohols, carboxylic acids (e.g., acetic acid), and amines (e.g., ammonia, pyridine). Aprotic solvents neither accept nor donate protons. Examples of aprotic solvents include carbon tetrachloride, chloroform, dichloromethane (DCM), acetonitrile (ACN), ethyl acetate (AcOEt), dimethylacetamide, tetrahydrofuran (THF), dimethylformamide (DMF), toluene, benzene, acetone, ethers (e.g., diethyl ether), alkanes (e.g., hexane), dimethylsulfoxide (DMSO), sulfur dioxide, hexamethylphosphoramide (HMPA), and, tetramethylurea. Amphoteric solvents, such as water, are capable of both accepting and donating protons.

Solvents may be classified as "hydroxylic" or "non-hydroxylic" according to whether they contain one or more hydrorxoyl, i.e. —OH, groups. Hydroxylic solvents include water and alcohols (e.g. methanol, ethanol), and non-hydroxylic solvents include dichoromehtane and toluene.

Solvents may also be classified as "organic" or "inorganic" according to their chemical composition. Conventionally, organic solvents comprise, at least, carbon atoms, while inorganic solvents do not. Examples of inorganic solvents include water, ammonia, and sulfur dioxide.

Anhydrous solvents are solvents which contain less than 0.1% by weight of water, and preferably less than 0.01% or 0.001% by weight of water.

Further Preferences

Preferred methods of the invention may include any appropriate combination of method steps as described above.

Preferences for the reaction conditions of the method steps of the invention have been described above.

Preferences for the various groups defined above are expressed below, and may be combined with each other as appropriate.

$R^2$ $R^2$ is preferably selected from R and =CH—R (wherein, in one aspect, R is preferably optionally substituted phenyl). If there is a double bond between C1 and C2 or C2 and C3, $R^2$ is preferably a group of formula X:

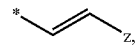

wherein z is selected from cyano, R, carboxy, ester and amido.

$R^3$ $R^3$ is preferably H.

$R^6$ $R^6$ is preferably selected from H and $C_{1-7}$ alkoxy, and more preferably H and methoxy, with H being the most preferred.

$R^7$ $R^7$ is preferably selected from H and OR, where OR is preferably optionally substituted $C_{1-7}$ alkoxy (e.g. methoxy, benzyloxy).

$R^8$ $R^8$ is preferably selected from either: H and OR, where OR is preferably optionally substituted $C_{1-7}$ alkoxy (e.g. methoxy, benzyloxy); or is a dimer link.

$R^9$ $R^9$ is preferably H.

$R^{11}$ is preferably H, but may be $C_{1-7}$ alkyl.

$R^{12}$ $R^{12}$ is preferably methyl.

EXAMPLES

General Experimental Methods

The progress of reactions was monitored by thin-layer chromatography (TLC) using Merck grade 7749 silica gel containing binding and fluorescence indicators, on glass plates. Visualization of TLC plate was achieved with UV light, unless otherwise stated. Flash column chromatography was performed using Merck silica gel 60 (0.040-0.063). The majority of organic solvents and reagents used were bought from Fischer, Lancaster and Aldrich Chemical Co. and inorganic drying agents from BDH.

¹H and ¹³C NMR spectra were obtained on a Bruker 250 MHz/52 mm; IR spectra were recorded with a FT-IR Spectrometer Spectrum 1000. The optical rotation of compounds was determined at ambient temperature with an ADP 220 polarimeter. Mass Spectrometry was carries out on a Micromass platform using either electrospray or Atmospheric Pressure chemical ionisation. Microanalysis was performed using a Carlo Erba 1108 elemental analyser.

Synthesis of Monomer Isocyanates (i) [2-(tert-Butyl-dimethyl-silanyloxymethyl)-pyrrolidin-1-yl]-(2-isocyanato-4,5-dimethoxy-phenyl)-methanone; and (ii) (2-Hydroxymethyl-pyrrolidin-1-yl)-(2-isocyanato-4,5-dimethoxy-phenyl)-methanone (8)

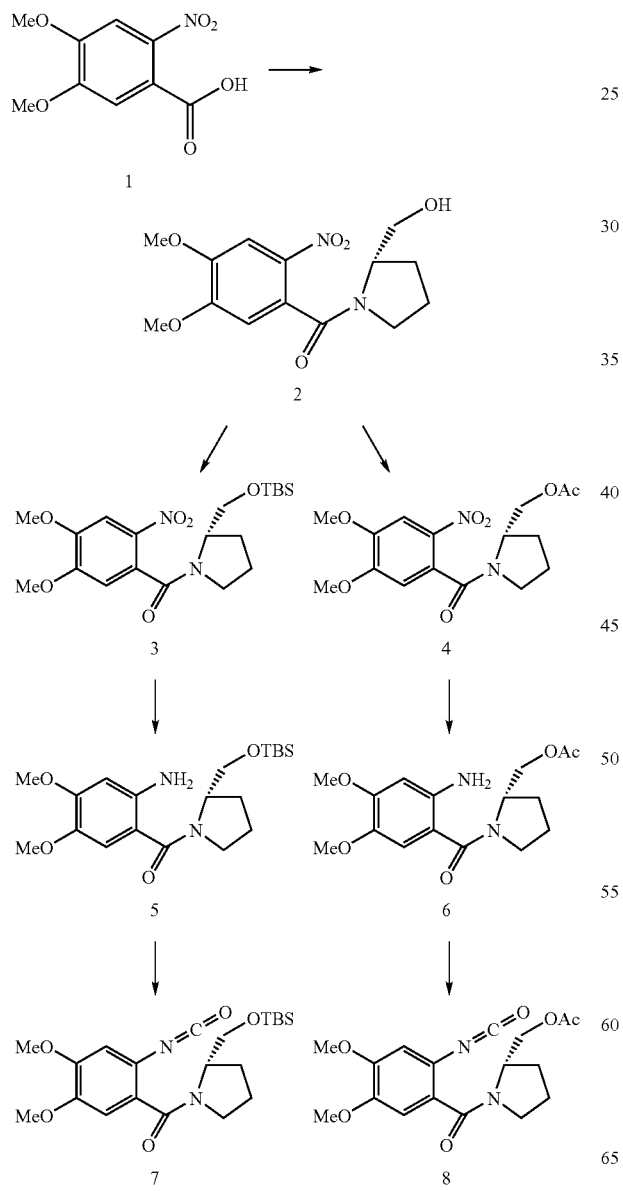

(4,5-Dimethoxy-2-nitro-phenyl)-(2-hydroxymethyl-pyrrolidin-1-yl)-methanone (2)

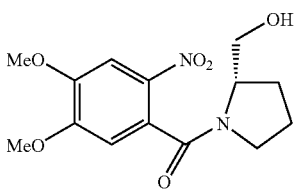

Oxalyl chloride (9.22 g, 6.4 mL, 72.6 mmol, 1.1 eq) and DMF (cat) were added to a suspension of 4,5-dimethoxy-2-nitrobenzoic acid (1, 15.0 g, 66 mmol) in anhydrous $CH_2Cl_2$ (150 mL) under a $N_2$ atmosphere. The suspension was stirred at room temperature for 18 hours. The resultant solution was added dropwise to a solution of (S)-(+)-2-pyrrolidine-methanol (7.33 g, 7.16 mL, 72.6 mmol, 1.1 eq) and triethylamine (14.77 g, 20.21 mL, 145 mmol, 2.2 eq) in anhydrous $CH_2Cl_2$ (100 mL) at −40° C. (dry ice/$CH_3CN$) under a $N_2$ atmosphere. The reaction mixture was allowed to come to room temperature and stirred for 18 h. The mixture was washed with 1 M HCl (3×200 mL), $H_2O$ (2×200 mL), satd $NaCl_{(aq)}$ (200 mL), dried ($MgSO_4$) and evaporated in vacuo to give a yellow foam. Trituration with 3% MeOH/EtOAc gave a white solid. Filtration and concentration of the filtrate gave a second crop of white solid. Total yield (18.13 g, 88.5%). mp 124.4-127.8° C.; $[\alpha]^{25}_D$−109.00 (c=1.0, $CHCl_3$); ¹H NMR ($CDCl_3$) δ 7.71 (s, 1H), 6.61 (s, 1H), 4.44-4.39 (m, 1H), 4.00 (s, 3H), 3.99 (s, 3H), 3.98-3.76 (m, 2H), 3.18 (m, 2H), 2.23-2.13 (m, 3H), 1.92-1.69 (m, 1H); ¹³C NMR ($CDCl_3$) δ 164.4, 154.5, 149.2, 137.1, 127.8, 109.0, 107.2, 65.7, 61.3, 56.8, 56.5, 49.5, 28.3, 24.3; IR (neat) 3343, 2940, 1605, 1530, 1337, 1276, 1109, 1064, 992, 862, 788, 756 $cm^{-1}$; HRMS m/z calcd for $C_{14}H_{18}N_2O_7$ 310.1234 (M+H) found 311.1243.

[2-(tert-Butyl-dimethyl-silanyloxymethyl)-pyrrolidin-1-yl]-(4,5-dimethoxy-2-nitro-phenyl)-methanone (3)

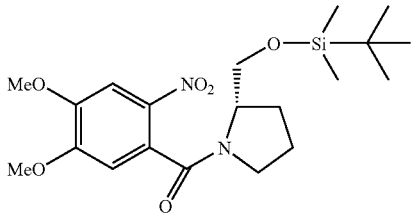

A solution of t-butyldimethylsilyl chloride (9.04 g, 60 mmol, 1.2 eq), imidazole (8.51 g, 125 mmol, 2.5 eq) and nitro-alcohol 2 (15.55 g, 50 mmol, 1 eq) in anhydrous DMF (30 mL) was stirred at room temperature under a $N_2$ atmosphere for 16 hours. The reaction mixture was diluted with $H_2O$ (500 mL) and extracted with EtOAc (2×200 mL). The combined organic extracts were washed with $H_2O$ (2×200 mL), satd $NaCl_{(aq)}$ (2×200 mL), dried ($MgSO_4$) and evaporated in vacuo. Purification by flash column chromatography (2% MeOH/$CHCl_3$) gave the product as a yellow foam (13.95 g, 66%). $[\alpha]^{25}_D$−99.50 (c=1.0, $CHCl_3$); ¹H NMR ($CDCl_3$) δ 7.68 (s, 1H), 6.75 (s, 1H), 3.96 (s, 3H), 3.88 (s, 3H), 3.90-3.88 (m, 2H), 3.13-3.08 (m, 2H), 2.07-2.03 (m, 3H), 2.01-1.81 (m, 1H), 0.91-0.77 (m, 9H), 0.10-0.07 (m, 6H); ¹³C NMR (CDCl$_3$) δ 166.7, 154.6, 149.2, 137.6, 137.6, 128.9, 109.4, 107.4, 64.1, 58.9, 57.0, 56.9, 49.4, 27.7, 26.2, 24.6, 18.5, −4.97; MS (AP) m/z 425 (M$^+$.); IR (neat) 3343, 2979, 2738, 2626, 1736, 1654, 1533, 1474, 1355, 1288, 1230, 1131, 880, 794, 669 cm$^{-1}$.

[2-(Acetyloxymethyl)-pyrrolidin-1-yl]-(4,5-dimethoxy-2-nitro-phenyl)-methanone (4)

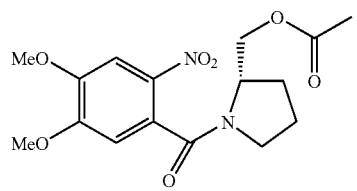

Pyridine (9.03 mL, 111.7 mmol, 1.1 eq) and acetic anhydride (10.5 mL, 111.7 mmol, 1.1 eq) were added to a solution of the nitro-alcohol 2 (31.5 g, 101.5 mmol, 1 eq) in anhydrous THF (300 mL) under a N$_2$ atmosphere. DMAP (2.48 g, 20.3 mmol, 0.2 eq) was added portion wise and the mixture was stirred at room temperature for 2.5 h. The solvent was removed in vacuo, the residue was treated with 1 M HCl (300 mL) and extracted with EtOAc (300 mL). The organic extract was washed with 1 M HCl (2×200 mL), H$_2$O (3×200 mL), satd NaCl$_{(aq)}$ (2×200 mL), dried (MgSO$_4$) and evaporated in vacuo to give the product as a yellow foam (34.5 g, 96%): [α]$^{27}_D$−89.0 (c 1.0, CHCl$_3$); $^1$H NMR (CDCl$_3$) δ 7.69 (s, 1H), 6.82 (s, 1H), 4.05-3.95 (m 9H), 3.24-3.08 (m, 2H), 2.11 (s, 3H), 2.00-1.41 (m, 4H); $^{13}$C NMR (CDCl$_3$) δ 170.9, 170.2, 151.7, 141.5, 140.7, 112.5, 111.3, 100.7, 64.6, 56.8, 55.7, 55.5, 49.8, 27.9, 24.7, 20.9; IR (neat) 3629, 3464, 2982, 1751, 1659, 1585; HRMS m/z calcd for C$_{16}$H$_{21}$N$_2$O$_7$ 353.1355 (M+H), found 353.1349.

(2-Amino-4,5-dimethoxy-phenyl)-[2-(tert-butyl-dimethyl-silanyloxymethyl)-pyrrolidin-1-yl]-methanone (5)

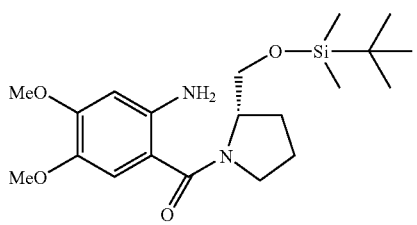

A solution of the nitro compound 3 (19.8 g, 46.6 mmol) in ethanol (180 mL) was hydrogenated (Parr apparatus) over 10% Palladium on carbon (2 g, 10 wt %), maintaining the H$_2$ pressure at 16 psi. The reaction was complete when no more H$_2$ was consumed. The mixture was filtered through celite and the ethanol evaporated in vacuo. Purification by flash column chromatography (2% MeOH/EtOAc) gave the product as a yellow oil (16.8 g, 91%). [α]$^{25}_D$−149.60 (c=1.0, CHCl$_3$); $^1$H NMR (CDCl$_3$) δ 6.75 (s, 1H), 6.24 (s, 1H), 4.45-4.32 (m, 1H), 3.84 (s, 3H), 3.78 (s, 3H), 3.64-3.50 (m, 4H), 2.08-2.00 (m, 3H), 1.93-1.74 (m, 1H), 0.89 (s, 9H), 0.09-0.01 (m, 6H); $^{13}$C NMR (CDCl$_3$) δ 169.8, 151.8, 141.8, 141.0, 112.5, 100.9, 63.1, 58.7, 56.9, 56.0, 27.5, 26.5, 25.6, 18.5, −5.0; MS (ES+) m/z 395 (M+1); IR (neat) 3465, 3363, 3225, 2973, 2738, 1636, 1523, 1475, 1291 cm$^{-1}$.

(2-Amino-4,5-dimethoxy-phenyl)-[2-(acetoxymethyl)-pyrrolidin-1-yl]-methanone (6)

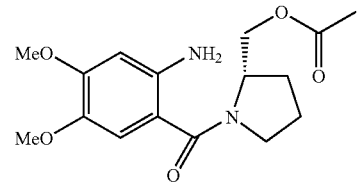

A solution of the nitro compound 4 (34.0 g, 96.5 mmol) in ethanol (80 mL) was hydrogenated (Parr apparatus) over 10% Palladium on carbon (3.4 g, 10 wt %) at 30 psi for 6 h. The mixture was filtered through celite and the ethanol evaporated in vacuo. Purification by flash column chromatography (2% MeOH/EtOAc) gave the product as a yellow oil (16.2 g, 52%): [α]$^{21}_D$−168.5 (c 1.0, CHCl$_3$); $^1$H NMR (CDCl$_3$) δ 6.73 (s, 1H), 6.26 (s, 1H), 4.66-4.53 (bs, 2H), 4.33-4.16 (bs, 2H), 3.91-3.71 (m, 7H), 3.60-3.44 (m, 2H), 2.22-2.01 (m, 5H), 2.01-1.87 (m, 1H), 1.87-1.70 (m, 3H); $^{13}$C NMR 170.9, 167.2, 154.4, 149.2, 137.3, 128.2, 109.2, 107.2, 63.9, 56.7, 56.5, 55.8, 48.4, 27.6, 24.1, 20.6; IR (neat) 3453, 3355, 3240, 2968, 2833, 1731, 1621, 1514; MS (ES+) m/z 323 (M$^+$. +1).

[2-(tert-Butyl-dimethyl-silanyloxymethyl)-pyrrolidin-1-yl]-(2-isocyanato-4,5-dimethoxy-phenyl)-methanone (7)

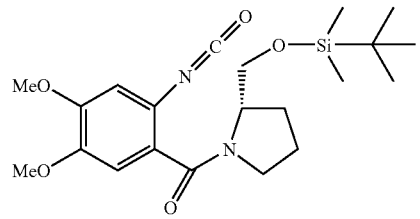

A solution of triethylamine (1.35 eq.) in anhydrous toluene was added to the amine (5)(1 eq.) and triphosgene (0.36 eq.) in anhydrous toluene under a N$_2$ atmosphere. The reaction was finished after 2 hours. (monitored by IR, ξ$_{NCO}$ 2265 cm$^1$). The product was used without further purification.

(2-Hydroxymethyl-pyrrolidin-1-yl)-(2-isocyanato-4,5-dimethoxy-phenyl)-methanone (8)

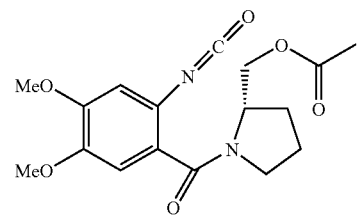

This was prepared from (6) in the same manner as above for (7).

Synthesis of Protecting Group Precursors

(i) 2-[3-(4-Hydroxymethyl-phenyl)ureido]-pentanedioic acid diallyl ester (35)

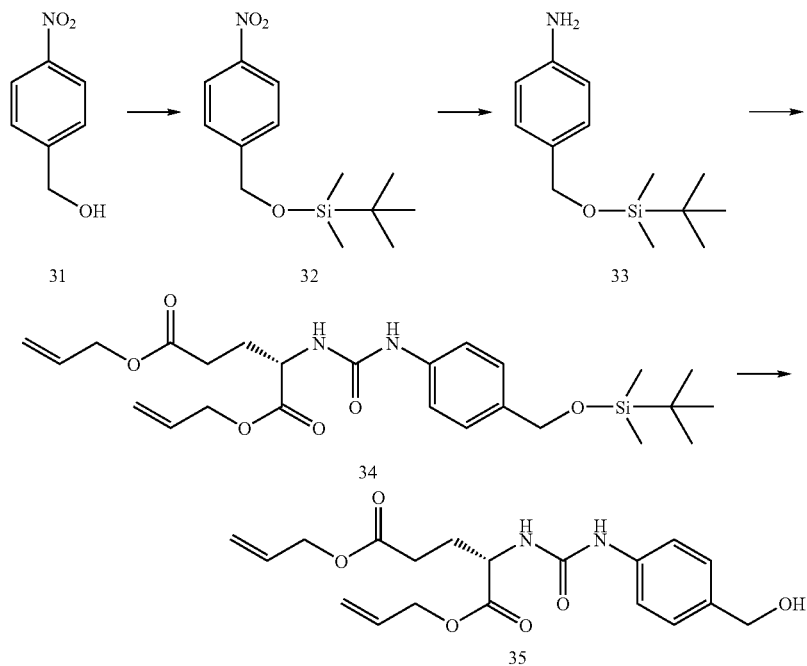

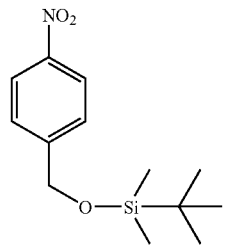

tert-Butyl-dimethyl-(4-nitro-benzyloxy)-silane (32)

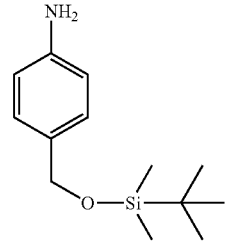

4-(tert-Butyl-dimethyl-silanyloxymethyl)-phenyl amine (33)

A solution of t-butyldimethylsilyl chloride (8.53 g, 56.3 mmol, 1.3 eq), imidazole (7.38 g, 108.3 mmol, 2.5 eq) and 4-nitro-benzyl alcohol (6.64 g, 43.3 mmol, 1 eq) in anhydrous DMF (25 mL) was stirred at room temperature under a $N_2$ atmosphere for 72 h. The reaction mixture was diluted with $H_2O$ (500 mL) and extracted with Etoac (4×100 mL). The combined organic extracts were washed with $H_2O$ (100 mL), satd $NaCl_{(aq)}$ (100 mL), dried ($MgSO_4$) and evaporated in vacuo. The residue was triturated with n-hexane and filtered. The filtrate was evaporated in vacuo to give the product as a yellow oil which crystallised (11.02 g, 95%). $^1$H NMR (CDCl$_3$) δ 8.2 (d, J=8.25 Hz, 2H), 7.47 (d, J=8.02 Hz, 2H), 4.8 (s, 2H), 0.96 (s, 9H), 0.12 (s, 6H). IR (neat) 2955, 2930, 1605 and 1522 cm$^{-1}$. HRMS m/z calcd for $C_{13}H_{22}NO_3$ Si 268.1369 (M+H), found 268.1376

Ammonium formate was added to a solution of the nitro compound 32 (8.86 g, 33.1 mmol, 1 eq) in ethanol (175 mL) over 10% Palladium on carbon (2.66 g, 30 wt %) [caution exothermic] and the mixture was stirred at room temperature for 2.5 h. The reaction mixture was filtered through celite and the solvent evaporated in vacuo. The residue was partitioned between EtOAc (100 mL) and $H_2O$ (100 mL), the organic portion was washed with $H_2O$ (100 mL), satd $NaCl_{(aq)}$ (100 mL), dried ($MgSO_4$) and evaporated to give the product as a yellow oil (7.3 g, 92%). $^1$H NMR (CDCl$_3$) δ 7.08 (d, J=7.8 Hz, 2H), 6.63 (d, J=7.8 Hz, 2H), 4.6 (s, 2H), 3.58 (bs, 2H), 0.9 (s, 9H), 0.07 (s, 6H). IR (neat) 3451, 3361, 3005, 2954, 1625 cm$^{-1}$. HRMS m/z calcd for $C_{13}H_{23}NO$ Si 237.1549 (M$^+$.), found 237.1552.

2-{3[4-(tert-Butyl-dimethyl-silanyloxymethyl)-phenyl]-ureido}-pentanedioic acid diallyl ester (34)

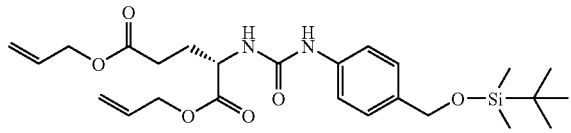

A solution of triethylamine (0.24 g, 0.33 mL, 2.4 mmol, 2 eq) in anhydrous CH$_2$Cl$_2$ (10 mL) was added dropwise to a solution of diallyl-L-glutamate tosylate (0.48 g, 1.2 mmol, 1 eq) and triphosgene (0.12 g, 0.4 mmol, 0.3 eq) in anhydrous CH$_2$Cl$_2$ (40 mL) stirring at −80° C. under a N$_2$ atmosphere. The mixture was stirred at −80° C. for 1 h then allowed to reach room temperature. A solution of the amino-silyl ether 33 (0.28 g, 1.2 mmol, 1 eq) and triethylamine (0.12 g, 0.17 mL, 1.2 mmol, 1 eq) in anhydrous CH$_2$Cl$_2$ (10 ml) was added dropwise (16 min) and the resulting solution stirred at room temperature for 18 h. The solvent was removed in vacuo and the residue triturated with toluene and filtered. The filtrate was evaporated to give the crude product as a yellow oil. Purification by flash column chromatography (20% EtOAc/80% n-hexane) gave the product as a colourless oil (0.35 g, 61%). $^1$H NMR (CDCl$_3$) δ 7.26 (s, 4H), 6.83 (s, 1H), 5.9 (m, 2H), 5.61 (d, J=8 Hz, 1H), 5.3 (m, 4H), 4.68 (s, 2H), 4.60 (m, 5H), 2.5 (m, 2H), 2.25 (m, 1H), 2.) (m, 1H), 0.95 (s, 9H) 0.07 (s, 6H). IR (neat) 3349, 2954, 2929, 2856, 1739, 1650, 1603, 1553 cm$^{-1}$. HRMS m/z calcd for C$_{25}$H$_{39}$N$_2$O$_6$ 491.2577 Si (M+H), found 491.2554.

2-[3-(4-Hydroxymethyl-phenyl)ureido]-pentanedioic acid diallyl ester (35)

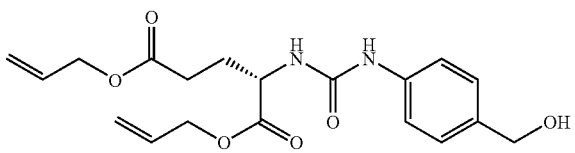

A solution of the TBDMS ether 34 (0.32 g, 0.65 mmol) in AcOH/THF/H$_2$O (9 mL/3 mL/3 mL) was stirred at room temperature for 2 h. The reaction mixture was cooled (ice bath) and neutralised with NaHCO$_{3(aq)}$ (13.2 g, 15.7 mmol) in H$_2$O (150 mL). The mixture was extracted with EtOAc (4×30 mL) and the combined extracts were washed with H$_2$O (100 mL), satd NaCl$_{(aq)}$ (100 mL), dried (MgSO$_4$) and evaporated in vacuo. Purification by flash column chromatography (60% EtOAc/40% n-hexane) gave the product as a colourless oil (0.22 g, 91%). $^1$H NMR (d$_6$ DMSO) δ 8.5 (s, 1H), 7.31 (d, J=8.5 Hz, 2H), 7.16 (d, J=8.12 Hz, 2H), 6.55 (d, J=8.1 Hz), 5.92 (m, 2H), 5.3 (m, 4H), 5.0 (t, J=5.55 Hz, 2H), 4.6 (m, 4H), 4.35 (m, 1H), 2.5 (m, 2H), 2.11 (m, 1H), 1.9 (m, 1H). IR (neat) 3353, 1738, 1659, 1602, 1551 cm$^{-1}$. HRMS m/z calcd for C$_{19}$H$_{25}$N$_2$O$_6$ 377.1713 (M+H), found 377.1705.

(ii) 2-(4-Hydroxymethyl-phenoxycarbonylamino)-pentanedioic acid diallyl ester (42)

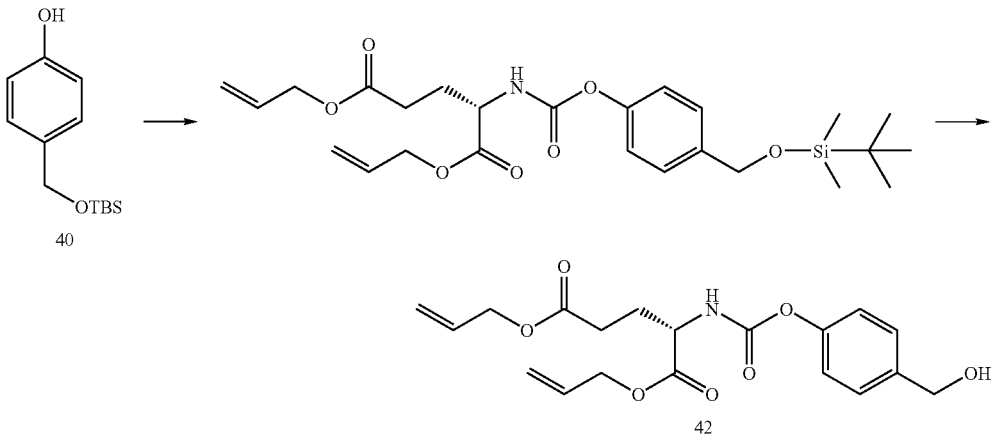

2-[4-(tert-Butyl-dimethyl-silanyloxymethyl)-phenoxycarbonylamino]-pentanedioic acid diallyl ester (41)

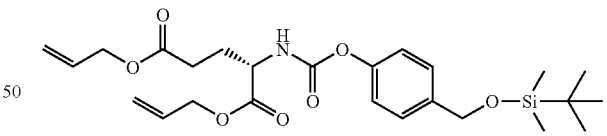

A solution of triethylamine (3.19 g, 4.4 mL, 31.6 mmol, 2.1 eq) in anhydrous CH$_2$Cl$_2$ (20 mL) was added dropwise to a solution of diallyl-L-glutamate tosylate (6.0 g, 15.0 mmol, 1 eq) and triphosgene (1.6 g, 5.4 mmol, 0.36 eq) in anhydrous CH$_2$Cl$_2$ (40 mL) stirring at −80° C. under a N$_2$ atmosphere. The mixture was stirred at −80° C. for 1.75 h then allowed to reach room temperature. A solution of hydroxyl-silyl ether 40, prepared using a literature procedure, (3.6 g, 15.0 mmol 1 eq) and triethylamine (1.7 g, 2.3 mL, 16.5 mmol, 1.1 eq) in anhydrous CH$_2$Cl$_2$ (35 mL) was added dropwise and the resulting solution was stirred at room temperature for 18 h. The solvent was removed in vacuo and the residue triturated with toluene and filtered. The filtrate was evaporated to give the crude product as a yellow oil. Purification by flash column chromatography (20% EtOAc/80% n-hexane) gave the product as a colourless oil (3.6 g, 46%). ¹H NMR (CDCl₃) δ 7.3 (d, J=8.5 Hz, 2H), 7.08 (d, J=8.5 Hz, 2H), 5.92 (m, 2H), 5.70 (d, J=8 Hz, 1H), 4.7 (s, 2H), 4.68 (d, J=5.8 Hz, 2H), 4.60 (d, J=5.8 Hz, 2H), 4.5 (m, 1H), 2.5 (m, 2H), 2.3 (m, 1H), 2.1 (m, 1H), 0.93 (s, 9H), 0.09 (s, 6H). IR (neat) 3350, 2954, 2930, 2865, 2857, 1738, 1531, 1503 cm⁻¹. HRMS m/z calcd for C$_{25}$H$_{38}$NO$_7$Si 492.2418 (M+H), found 492.2411.

2-(4-Hydroxymethyl-phenoxycarbonylamino)-pentanedioic acid diallyl ester (42)

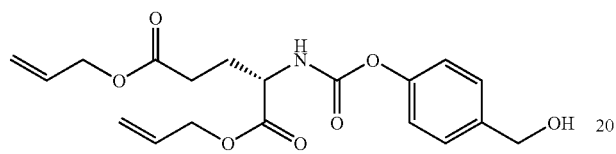

A solution of the TBDMS ether 41 (3.23 g, 6.56 mmol) in AcOH/THF/H₂O (18 mL/6 mL/6 mL) was stirred at room temperature for 2 h. The reaction mixture was cooled (ice bath) and neutralised with Na₂CO₃$_{(aq)}$ (16.6 g, 15.6 mmol) in H₂O (135 mL). The mixture was extracted with EtOAc (4×150 mL) and the combined extracts were washed with H₂O (250 mL), satd NaCl$_{(aq)}$ (250 mL), dried (MgSO₄) and evaporated in vacuo. Purification by flash column chromatography (50% EtOAc/50% n-hexane) gave the product as a colourless oil (2.28 g, 92%). ¹H NMR (CDCl₃) δ 7.34 (d, J=8.5 Hz, 2H), 7.11 (d, J=8.5 Hz, 2H), 5.92 (m, 2H), 5.79 (m, 2H), 5.79 (d, J=8.1 Hz, 1H), 5.3 (m, 4H), 4.65 (m, 6H), 4.49 (m, 1H), 2.50 (m, 2H), 2.35 (m, 1H), 2.1 (m, 1H). IR (neat) 3349, 3080, 3028, 2943, 2879, 1731, 1535, 1503 cm⁻¹. HRMS m/z calcd for C$_{19}$H$_{24}$NO$_7$ 378.1553 (M+H), found 378.1559.

(iii) 4-(4-hydroxymethyl-2-methoxy-5-nitrophenoxy)butyric acid allyl ester (52)

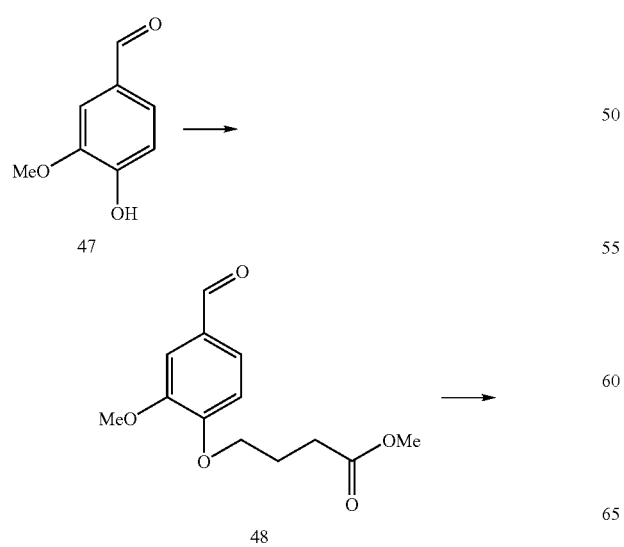

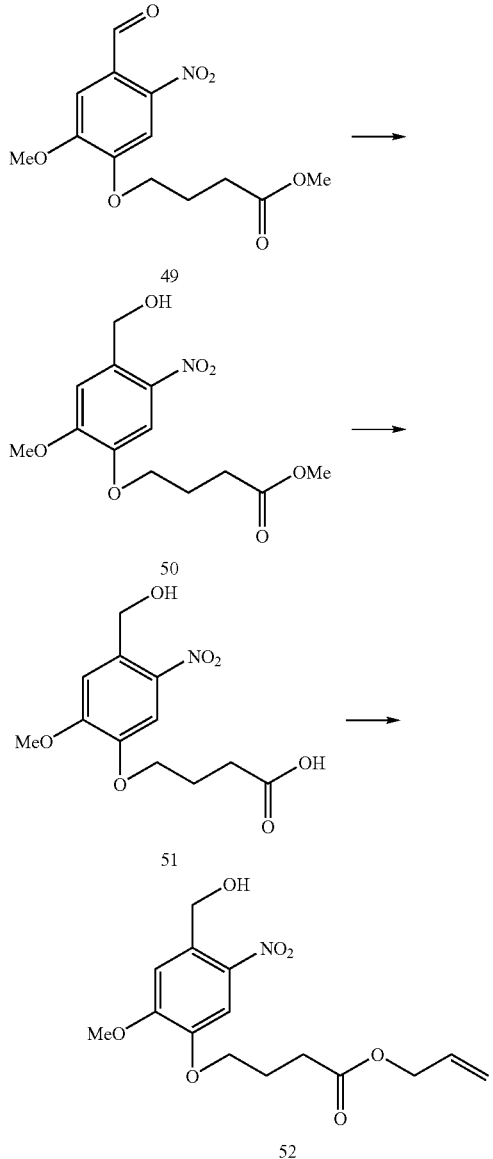

4-(4-formyl-2-methoxyphenoxy)-butyric acid methyl ester (48)

A solution of vanillin (47)(40.00 g, 262.89 mmol) and methyl-4-bromobutyrate (50.00 g, 276.18 mmol) in DMF (200 mL) was allowed to stir over potassium carbonate (51.53 g, 372.40 mmol) for 16 hours. Water was added to the reaction mixture at which time the product crystallised. The resulting mixture was filtered and dried in vacuo for 16 hours to afford the keto-ester (48) as a white solid (41.3 g, 66%). MP=57-59° C. $^1$H NMR (250 MHz, CDCl$_3$) δ 9.80 (s, 1H), 7.46-7.40 (m, 2H), 6.97 (d, J=8.1 Hz, 1H), 4.16 (t, J=6.3 Hz, 2H), 3.92 (s, 3H), 3.70 (s, 3H), 2.57 (t, J=7.2 Hz, 2H), 2.20 (pent, J=6.7 Hz, 2H). $^{13}$C NMR (67.8 MHz, CDCl$_3$) 188.2 (Cl), 173.7 (C12), 153.8 (Cquat.), 152.0 (Cquat.), 144.1 (Cquat.), 125.8 (Cmethine), 110.3 (C3), 108.5 (C6), 69.0 (C9), 57.0 (C8), 52.2 (C13), 30.6 (C11), 24.5 (C10). It was decided to adopt the numbering system shown in the figure below for the molecule for ease of peak assignment in $^{13}$C NMR.

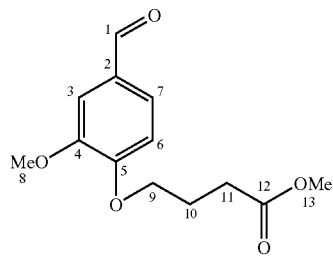

IR (cm$^{-1}$) 3450, 3332, 2952, 1737, 1685, 1587, 1467, 1407, 1006, 938, 864, 813, 730, 656. MS (M+) 253. Anal. Calcd for C$_{13}$H$_{16}$O$_5$: C, 61.90; H, 6.39. Found: C, 61.50; H, 6.39.

4-(4-formyl-2-methoxy-5-nitro-phenoxy)-butyric acid methyl ester (49)

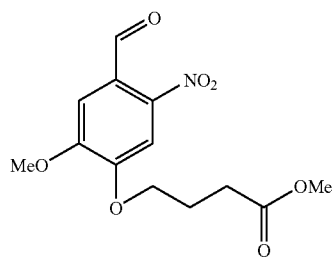

A solution of the keto-ester (48)(20.00 g, 79.3 mmol) in acetic anhydride (80 mL) was added dropwise to a stirring solution of HNO$_3$ (400 mL) and Ac$_2$O (80 mL) at 0° C. After stirring for 2.5 hours the reaction mixture was poured into iced water (3 L) and allowed to stand at 4° C. for a further 16 hours. The precipitate was collected by filtration and dried under vacuum to provide the nitro compound (49) as a yellow crystalline solid (14.52 g, 62%). Melting Point 70-73° C. $^1$H NMR (250 MHz, CDCl$_3$) δ 10.4 (s, 2H), 7.61 (s, 1H), 7.40 (s, 1H), 4.21 (t, J=6.2 Hz, 2H), 4.00 (s, 3H), 3.71 (s, 3H), 2.58 (t, J=7.1 Hz, 2H), 2.23 (pent, J=6.3 Hz, 2H). $^{13}$C NMR (67.8 MHz, CDCl$_3$) 188.2 (C1), 173.7 (C12), 153.8 (Cquat.), 152.1 (Cquat.), 144.1 (Cquat.), 125.8 (Cquat.), 110.2 (C6), 108.5 (C3), 69.0 (C9), 57.0 (C8), 52.2 (C13), 30.6 (C$_{11}$), 24.4 (C10). IR (cm$^{-1}$) 3571, 3485, 2951, 1725, 1689, 1573, 1329, 1172, 1064, 1002, 936, 896, 858, 820, 766, 738, 688, 624. MS (M+1) 298.0. Anal. Calcd for C$_{13}$H$_{15}$NO$_7$: C, 52.53; H, 5.09; N, 4.71. Found: C, 52.80; H, 5.03; N, 4.75.

4-(4-hydroxymethyl-2-methoxy-5-nitrophenoxy) butyric acid methyl ester (50)

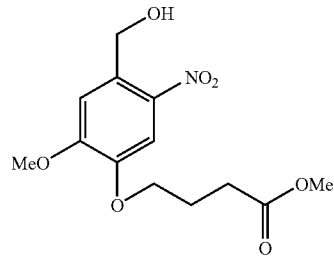

Sodium borohydride (2.69 g, 71.3 nmol) was added to a stirred solution of the ester (49)(10.0 g, 33.6 mmol) in THF (50 mL) under an N$_2$ atmosphere at room temperature. Effervescence was observed upon addition of the reducing agent. TLC (EtOAc) after 16 hours revealed the complete loss of starting material. The solution was concentrated and redissolved in EtOAc (100 mL). The organic layer was washed with sat. NH$_4$Cl (5×100 mL) and concentrated in vacuo. Purification by flash chromatography (1% MeOH/CHCl$_3$) yielded the product (50) as a yellow solid (6.46 g, 64%). MP=98-102° C. $^1$H NMR (250 MHz, CDCl$_3$) δ 7.70 (s, 1H), 7.16 (s, 1H), 4.95 (d, J=6.5 Hz, 2H), 4.12 (t, J=6.2 Hz, 2H), 3.98 (s, 3H), 3.70 (s, 3H), 2.71 (t, J=6.5 Hz, 1H), 2.56 (t, J=7.1 Hz, 2H), 2.19 (pent, J=6.7 Hz, 2H). $^{13}$C NMR (67.8 MHz, CDCl$_3$) 173.9 (C12), 154.6 (Cquat.), 147.3 (Cquat.), 139.6 (Cquat.), 133.2 (Cquat.), 111.0 (C6), 109.8 (C3), 68.6 (C9), 62.7 (C1), 56.7 (C8), 52.1 (C13), 30.7 (C11), 24.6 (C$_{10}$). IR (cm$^{-1}$) 3286, 2937, 2881, 1737, 1577, 1533, 1368, 1332, 1282, 1162, 1008, 979, 950, 872, 821, 755, 651. MS (M+) 299.0. Anal. Calcd for C$_{13}$H$_{17}$NO$_7$: C, 52.17; H, 5.73; N, 4.68. Found: C, 52.41; H, 5.86; N, 4.67.

4-(4-hydroxymethyl-2-methoxy-5-nitrophenoxy) butyric acid (51)

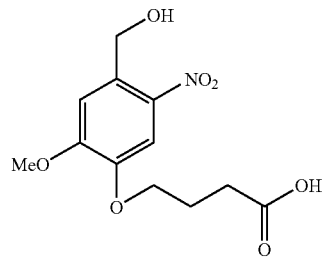

A solution of the ester (50)(10.00 g, 33.4 mmol) in methanol (100 mL) was added dropwise to a stirring solution of 1M NaOH (100 mL) and H$_2$O (50 mL). TLC (1:10:100 Acetic acid: MeOH: CHCl$_3$) after 16 hours revealed the complete loss of starting material. The solution was acidified to pH1 with conc. HCl. The resulting yellow precipitate was collected by vacuum filtration to provide the product (51) as a yellow solid (8.58 g, 90%). MP=172-175° C. $^1$H NMR (250 MHz, CDCl$_3$) δ 7.71 (s, 1H), 7.40 (s, 1H), 4.99 (s, 2H), 4.13 (t, J=6.3 Hz, 2H), 3.98 (s, 3H), 2.52 (t, J=7.1 Hz, 2H), 2.15

(pent, J=6.7 Hz, 2H). $^{13}$C NMR (67.8 MHz, CDCl$_3$) 174.5 (C12), 154.2 (Cquat.), 146.4 (Cquat.), 138.5 (Cquat.), 134.7 (Cquat.), 109.8 (C6), 109.3 (C3), 68.3 (C9), 60.9 (C1), 56.2 (C8), 30.2 (C11), 24.3 (C10). IR (cm$^{-1}$) 3533, 2976, 2634, 1709, 1617, 1577, 1520, 1411, 1286, 1214, 1019, 990, 888, 876, 814, 756, 677. MS (M$^+$ —OH) 268.0. Anal. Calcd for C$_{12}$H$_{15}$NO$_7$: C, 50.53; H, 5.30; N, 4.91. Found: C, 50.48; H, 5.22; N, 4.88.

4-(4-hydroxymethyl-2-methoxy-5-nitrophenoxy) butyric acid allyl ester (52)

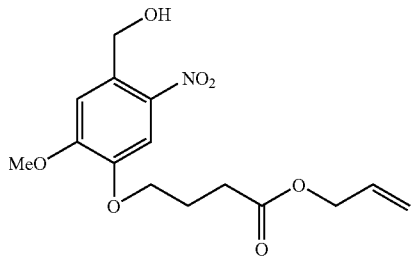

A mixture of compound 51 (7.00 g 24.50 mmol), allyl alcohol (80 mL) and p-tosic acid (742 mg, 3.90 mmol) was heated at reflux under a N$_2$ atmosphere for 4 hOURS, at which time TLC (2% MeOH/CHCl$_3$) indicated that reaction had gone to completion. Excess allyl alcohol was evaporated in vacuo to afford the crude compound (52), which was partitioned between NaHCO$_3$ (50 mL) and EtOAc (50 mL). The organic layer was washed with water (3×50 mL), brine (3×50 mL) and then dried (MgSO$_4$), and concentrated in vacuo. Purification by flash chromatography (CHCl$_3$) yielded the product as an orange-brown solid (5.78 g, 72%). MP=73-75° C. $^1$H NMR (250 MHz, CDCl$_3$) δ 7.70 (s, 1H), 7.16 (s, 1H), 6.00-5.84 (m, 1H), 5.36-5.21 (m, 2H), 4.94 (d, J=6.3 Hz), 4.62-4.59 (m, 2H), 4.13 (t, J=6.2 Hz, 2H), 3.97 (s, 3H), 2.67-2.56 (m, 3H), 2.20 (pent, J=6.7 Hz, 2H). $^{13}$C NMR 5173.1 (C12), 154.7 (Cquat.), 147.3 (Cquat.), 139.6 (Cquat.), 133.2 (Cquat.), 132.4 (C14), 118.7 (C15), 111.1 (C6), 109.9 (C3), 68.6 (C9), 65.6 (C13), 62.7 (C1), 56.7 (C8), 30.9 (C11), 24.6 (C10). IR (cm$^{-1}$) 3329.4, 3100.0, 2972.1, 1734.5, 1647.9, 1577.4, 1508.1, 1281.5, 932.8, 884.0, 815.8, 758.2, 662.2. MS (M$^+$ —OH) 308. Anal. Calcd for C$_{16}$H$_{19}$NO$_7$: C, 55.38; H, 5.89; N, 4.31. Found: C, 52.41; H, 5.86; N, 4.67.

Synthesis of Monomer Carbamates

General Method

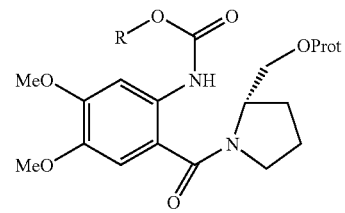

A solution of the appropriate alcohol (1 eq) and triethylamine (1.1 eq) in either anhydrous toluene or anhydrous CH$_2$Cl$_2$ was added dropwise to a solution of the appropriate isocyanate (1 eq) in anhydrous toluene. The reaction was monitored by IR (disappearance of the ξ$_{NCO}$ 2265 cm$^{-1}$ peak). The reaction mixture was filtered and the filtrate evaporated in vacuo. The product was purified by flash column chromatography.

[2-[2-(tert-Butyl-dimethyl-silanyloxymethyl)-pyrrolidine-1-carbonyl]-4,5-dimethoxy-phenyl]-carbamic acid-benzyl ester (9)

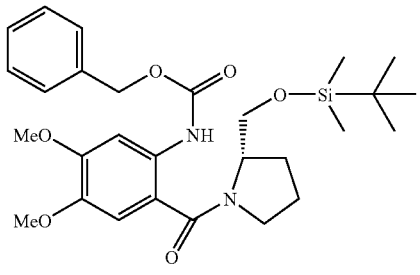

A solution of anhydrous benzyl alcohol (0.19 g, 0.18 mL, 1.7 mmol) and triethylamine (0.19 g, 0.26 mL, 1.85 mmol) in anhydrous toluene (5 mL) was added to a solution of the isocyanate 7 prepared from the amine 5 (0.522 g, 1.32 mmol), triphosgene (0.14 g, 0.48 mmol) and triethylamine (0.18 g, 0.25 mL, 1.8 mmol) in anhydrous toluene (15 mL). The reaction was complete in 16 hours. The product was obtained (flash column chromatography 20% EtOAc/80% n-hexane) as a colourless oil (0.49 g, 70%): ν$_{max}$/cm$^1$ (film) 1727 (C=O, carbamate); [α]$_D^{24.2}$–80.6° (c=0.217, CHCl$_3$) $^1$H NMR (CDCl$_3$) δ 9.2 (bs, 1H), 7.9 (s, 1H), 7.4 (m, 5H), 6.83 (s, 1H), 5.18 (s, 2H), 4.35 (s, 1H), 4.0 (s, 1H), 3.94 (s, 3H), 3.82 (s, 3H), 3.65 (m, 1H), 3.50 (m, 2H), 2.11 (m, 2H), 1.95 (m, 1H), 1.75 (m, 1H), 0.9 (s, 9H), 0.07 (s, 6H). IR (neat) 3302, 2953, 2852, 1729, 1620, 1598, 1528, cm$^{-1}$.

[2-[2-(tert-Butyl-dimethyl-silanyloxymethyl)-pyrrolidine-1-carbonyl]-4,5-dimethoxy-phenyl]-carbamic acid-4-methoxy-benzyl ester (10)

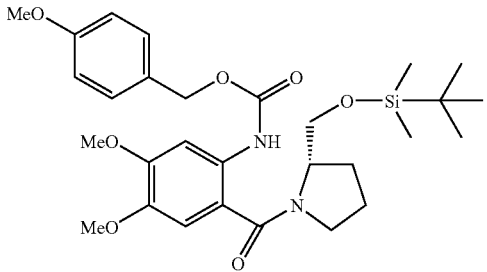

A solution of 4-methoxybenzyl alcohol (0.164 g, 1.19 mmol) and triethylamine (0.132 g, 0.18 mL, 1.3 mmol) in anhydrous toluene (10 mL) was added to a solution of the isocyanate 7 prepared from the amine 5 (0.47 g, 1.19 mmol), triphosgene (0.127 g, 0.43 mmol) and triethylamine (0.162 g, 0.22 mL, 1.6 mmol) in anhydrous toluene (20 mL). The reaction was complete in 20 hours. The product was obtained (flash column chromatography 40% EtOAc/60% n-hexane) as a colourless oil (0.45 g, 69%): ν$_{max}$/cm$^1$ (film) 1727 (C=O, carbamate); [α]$_D^{25.7}$–71.27° (c=0.225, CHCl$_3$) $^1$H NMR (CDCl$_3$) δ 9.15 (s, 1H), 7.9 (s, 1H), 7.33 (d, J=6.56 Hz, 2H), 6.9 (d, J=6.6 Hz, 2H), 6.81 (s, 1H), 5.10 (d, J=11.92 Hz, 2H), 4.34 (m, 1H), 3.99 (m, 1H), 3.93 (s, 3H), 3.81 (s, 6H), 3.65 (m, 1H), 2.03 (m, 2H), 1.95 (m, 1H), 1.7 (m, 1H), 0.89 (s, 9H), 0.04 (s, 6H). IR (CHCl$_3$) 2953, 1727, 1598, 1556 cm$^{-1}$. HRMS m/z calcd for C$_{29}$H$_{42}$N$_2$O$_7$Na 581.2659 (M+Na), found 581.2663.

[2-[2-(tert-Butyl-dimethyl-silanyloxymethyl)-pyrrolidine-1-carbonyl]-4,5-dimethoxy-phenyl]-carbamic acid-2-trimethylsilanyl-ethyl ester (11)

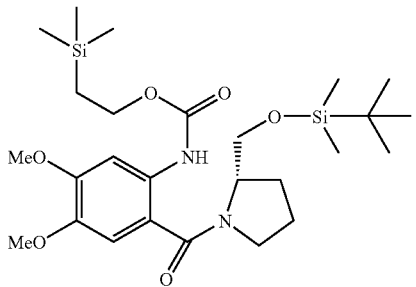

A solution of 2-trimethylsilyl ethanol (0.168 g, 0.2 mL, 1.42 mmol) and triethylamine (0.156 g, 0.22 mL, 1.55 mmol) in anhydrous toluene (10 mL) was added to a solution of the isocyanate 7 prepared from the amine 5 (0.509 g, 1.29 mmol), triphosgene (0.138 g, 0.46 mmol) and triethylamine (0.176 g, 0.24 mL, 1.74 mmol) in anhydrous toluene (25 mL). The reaction was complete in 21 hours. The product was obtained (flash column chromatography 40% EtOAc/60% n-hexane) as a colourless oil (0.417 g, 60%): ν$_{max}$/cm$^{-1}$ (film) (C=O, carbamate);); [α]$_D^{22.6}$ −96.15° (c=0.21, CHCl$_3$), $^1$H NMR (CDCl$_3$) δ 9.03 (bs, 1H), 7.87 (s, 1H), 7.87 (s, 1H), 6.82 (s, 1H), 4.35 (m, 1H), 4.2 (m, 2H), 4.01 (m, 1H), 3.93 (s, 3H), 3.82 (s, 3H), 3.70 (m, 1H), 3.50 (m, 2H), 2.10 (m, 2H), 1.98 (m, 1H), 1.70 (m, 1H), 1.10 (m, 2H), 0.9 (s, 9H), 0.08 (s, 15H), IR (neat) 3305, 2953, 2857, 1727, 1622, 1599, 1522 cm$^{-1}$.

[2-[2-(tert-Butyl-dimethyl-silanyloxymethyl)-pyrrolidine-1-carbonyl]-4,5-dimethoxy-phenyl]-carbamic acid-3-(4-nitrophenyl)-allyl ester (12)

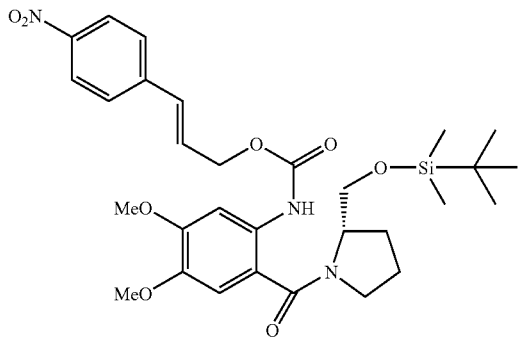

A solution of 3-(4-nitrophenyl)-prop-2-en-1-ol (0.222 g, 1.24 mmol) and triethylamine (0.138 g, 0.19 mL, 1.37 mmol) in anhydrous CH$_2$Cl$_2$ (10 mL) was added to a solution of the isocyanate 7 prepared from the amine 5 (0.491 g, 1.24 mmol), triphosgene (0.132 g, 0.45 mmol) and triethylamine (0.17 g, 0.23 mL, 1.68 mmol) in anhydrous toluene (20 mL). The reaction was complete in 20 hours. The product was obtained (flash column chromatography 50% EtOAc/50% n-hexane) as a yellow oil which crystallised (0.432 g, 58%): ν$_{max}$/cm$^{-1}$ (film) (C=0, carbamate); [α]$_D^{25.3}$ −65.0° (c=0.24, CHCl$_3$), $^1$H NMR (CDCl$_3$) δ 9.39 (bs, 1H), 7.89 ((s, 1H), 8.19 (d, J=8.8 Hz, 2H), 7.53 (d, J=9 Hz, 2H), 6.85 (s, 1H), 6.73 (d, J=15.9 Hz, 1H), 6.52 (dt, J=5.8, 15.9 Hz, 1H) 4.86 (m, 2H) 4.38 (m, 1H), 4.01 (m, 1H), 3.94 (s, 3H), 3.83 (s, 3H), 3.70 (m, 1H), 3.52 (m, 2H), 2.06 (m, 2H), 1.95 (m, 1H), 1.72 (m, 1H), 0.9 (s, 9H), 0.08 (s, 6H). IR (neat) 3340, 2930, 1729, 1597, 1519 cm$^{-1}$. HRMS m/z calcd for C$_{30}$H$_{31}$N$_3$O$_8$SiNa 622.2561 (M+Na), found 622.2542.

(2-[-(tert-Butyl-dimethyl-silanyloxymethyl)-pyrrolidine-1-carbonyl]-4,5-dimethoxy-phenyl)-carbamic acid 2-benzenesulfonyl-ethyl ester (13)

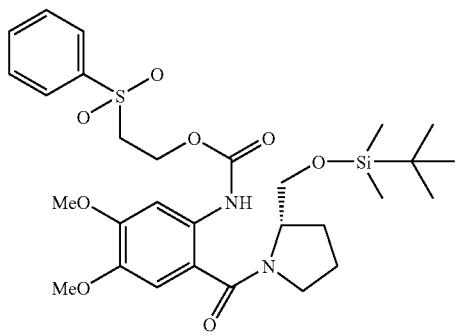

A solution of phenylsulfonylethanol (0.26 g, 0.167 mL 1.39 mmol) and triethylamine (0.13 g, 0.18 mL, 1.29 mmol) in anhydrous toluene (10 mL) was added to a solution of the isocyanate 7 prepared from the amine 5 (0.5 g, 1.27 mmol), triphosgene (0.135 g, 0.34 mmol) and triethylamine (0.17 g, 0.24 mL, 1.72 mmol) in anhydrous toluene (20 mL). The reaction was complete in 96 hours. The product was obtained (flash column chromatography 60% EtOAc/40% n-hexane) as a yellow oil (0.3 g, 39%). [α]$_D^{24.1}$ −81.5° (c=0.23, CHCl$_3$), $^1$H NMR (CDCl$_3$) δ 9.1 (s, 1H), 7.95 (d, J=8 Hz, 2H), 7.72 (s, 1H), 7.58 (m, 3H), 6.82 (s, 1H), 4.45 (t, J=6.3 Hz, 2H), 4.35 (m, 1H), 3.95 (m, 1H), 3.91 (s, 3H), 3.82 (s, 3H), 3.70 (m, 1H), 3.5 (m, 4H), 2.1 (m, 2H), 1.95 (m, 1H), 1.7 (m, 1H), 0.9 (s, 9H), 0.05 (s, 6H).

Acetic acid 1-[2-(4,5-dimethoxy-2-nitro-benzyloxycarbonylamino)-4,5-dimethoxy-benzoyl]-pyrrolidin-2-ylmethyl ester (14)

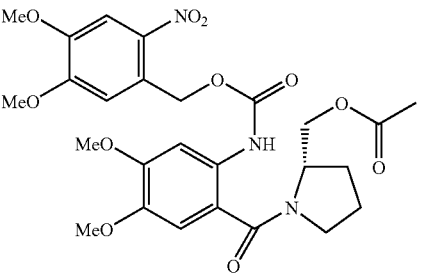

A solution of nitroveratryl alcohol (1.98 g, 9.3 mmol) and triethylamine (0.94 g, 1.29 mL, 9.3 mmol) in anhydrous CH$_2$Cl$_2$ (30 mL) was added to a solution of the isocyanate 8 prepared from the amine 6 (3.0 g, 9.3 mmol), triphosgene (0.99 g, 3.4 mmol) and triethylamine (1.27 g, 1.75 mL, 12.6 mmol) in anhydrous toluene (60 mL). The reaction was complete in 16 h. The product was obtained (flash column chromatography 40% EtOAc/60% n-hexane) as a yellow foam (4.15 g, 69%). [α]$^{25}_D$−62.50 (c=1.0, CHCl$_3$); $^1$H NMR (CDCl$_3$) δ 9.16 (s, 1H), 7.80 (s, 1H), 7.74 (s, 1H), 7.10 (s, 1H), 6.83 (s, 1H), 5.65 (d, J=15.2 Hz, 1H), 5.55 (d, J=15.2 Hz, 1H), 4.58 (bs, 1H), 4.29 (bs, 2H), 3.99-3.86 (m, 12H), 3.66-3.46 (m, 2H), 2.07 (s, 3H), 2.03-1.90 (m, 1H), 1.90-1.67 (m, 3H); $^{13}$C NMR (CDCl$_3$) δ 169.5, 153.7, 153.2, 151.3, 148.1, 143.9, 139.6, 132.2, 127.9, 115.3, 111.2, 109.9, 108.2, 104.4, 64.4, 63.6, 56.5, 56.4, 56.4, 56.0, 55.9, 50.8, 27.7, 25.0, 20.8; MS (AP) m/z (relative intensity) 584 (M+Na), 562 (M+1); IR (neat) 3333, 2939, 1735, 1672, 1600, 1520, 1462, 1395, 1327, 1274, 1221, 1173, 1114, 1072, 1036, 873, 795.1, 756.1 (cm$^{-1}$); HRMS m/z calcd for C$_{26}$H$_{32}$N$_3$O$_{11}$ 562.2033 (M+H) found 562.2037.

triphosgene (0.99 g, 3.4 mmol) and triethylamine (1.27 g, 1.75 mL, 12.6 mmol) in anhydrous toluene (100 mL). The reaction was complete in 16 hours. The product was obtained (flash column chromatography 60% EtOAc/40% n-hexane) as a yellow foam (1.84 g, 30%). [α]$^{25}_D$−54.5° (c=1.0, CHCl$_3$); $^1$H NMR (CDCl$_3$) δ 9.15 (s, 1H), 7.80 (s, 1H), 7.73 (s, 1H), 7.09 (s, 1H), 6.83 (s, 1H), 5.98-5.87 (m, 1H), 5.69 (d, J=15.2 Hz, 1H), 5.53 (d, J=15.2 Hz, 1H), 5.35-5.22 (m, 2H), 4.62-4.58 (m, 3H), 4.29 (bs, 2H), 4.18-4.11 (m, 2H), 3.97 (s, 3H), 3.92 (s, 3H), 3.89 (s, 3H), 3.58-3.51 (m, 2H), 2.59 (t, J=7.2 Hz, 2H), 2.24-2.15 (m, 2H), 2.06 (s, 3H), 1.98-1.79 (m, 4H); $^{13}$C NMR (CDCl$_3$) δ 172.5, 170.9, 169.4, 154.1, 153.2, 151.2, 147.3, 143.9, 139.5, 132.1, 128.0, 118.4, 115.3, 111.2, 110.1, 109.6, 104.4, 68.2, 65.3, 64.5, 63.7, 56.6, 56.4, 56.0, 55.9, 50.9, 30.6, 27.6, 25.0, 24.2, 20.9; MS (AP) m/z (relative intensity) 673 (M$^+$., 15), 515 (14), 487 (4), 400 (3), 349 (9), 322 (22), 308 (30), 289 (8), 247 (4), 224 (6); IR (neat) 2940, 1735, 1600, 1520, 1465, 1395, 1326, 1275, 1228, 1173, 1114, 1069, 1037, 993, 939, 871, 755 cm$^{-1}$; HRMS m/z calcd for C$_{32}$H$_{39}$N$_3$O$_{13}$ 673.2494 (M$^+$) found 673.2483.

2-[3-(4-{2-[2-(tert-Butyl-dimethyl-silanyloxymethyl)-pyrrolidine-1-carbonyl]-4,5-dimethoxy-phenylcarbamoyloxymethyl}-phenyl)-ureido]-pentanedioic acid diallyl ester (36)

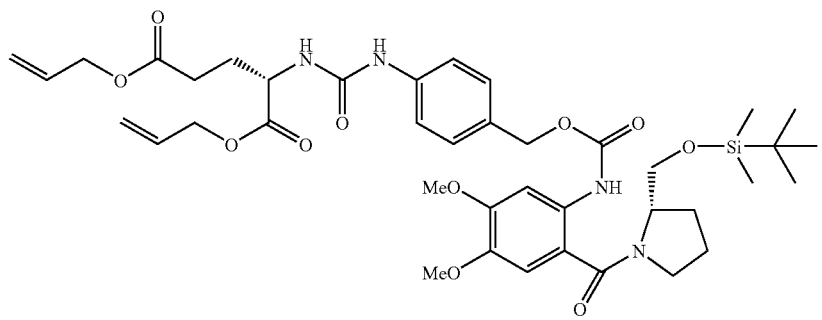

4-(4-[2-(2-Acetoxymethyl-pyrrolidine-1-carbonyl)-4,5-dimethoxy-phenylcarbamoyloxymethyl]-2-methoxy-5-nitro-phenoxy)butyric acid allyl ester (15)

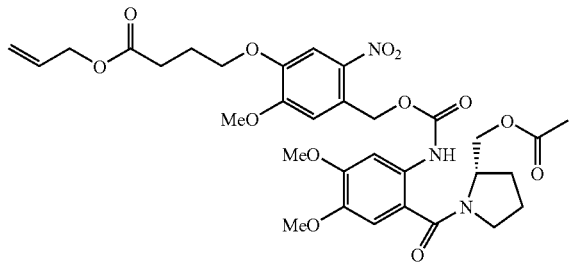

A solution of linker alcohol (52)(3.02 g, 9.3 mmol) and triethylamine (0.94 g, 1.29 mL, 9.3 mmol) in anhydrous CH$_2$Cl$_2$/toluene (20 mL/10 mL) was added to a solution of the isocyanate 8 prepared from the amine 6 (3.0 g, 9.3 mmol), A solution of the urea progroup 35 (2.03 g, 5.4 mmol) and triethylamine (0.6 g, 0.83 mL, 5.95 mmol) in anhydrous CH$_2$Cl$_2$ (55 mL) was added to a solution of the isocyanate 7 prepared from the amine 5 (2.13 g, 5.4 mmol), triphosgene (0.58 g, 1.95 mmol) and triethylamine (0.74 g, 1.01 mL, 7.3 mmol) in anhydrous toluene (70 mL). The reaction was complete in 20 h. The product was obtained (flash column chromatography 60% EtOAc/40% n-hexane) as a white foam (1.94 g, 45%). [α]$_D^{24}$−40.6° (c=0.234, CHCl$_3$), $^1$H NMR (CDCl$_3$) δ 9.1 (bs, 1H), (7.85 (5, 1H), 7.31 (s, 1H), 6.87 (s, 1H), 6.82 (s, 1H), 5.90 (m, 2H), 5.62 (d, J=11.7 Hz, 1H), 5.25 (m, 4H), 5.11 (s, 2H), 4.63 (m, 5H), 4.35 (m, 1H), 3.99 (m, 1H), 3.92 (s, 3H), 3.81 (s, 3H), 3.63 (m, 1H), 3.51 (m, 2H), 2.50 (m, 2H), 2.25 (m, 1H), 2.00 (m, 3H), 1.70 (m, 1H), 0.9 (s, 9H), 0.05 (s, 6H). IR (neat) 3349, 2952, 2856, 1732, 1664, 1600, 1520 cm$^{-1}$. HRMS m/z calcd for C$_{40}$H$_{56}$N$_4$O$_{11}$SiCs 929.2769 (M+Cs), found 929.2727.

2-(4-{2-[2-(tert-Butyl-dimethyl-silanyloxymethyl)-pyrrolidine-1-carbonyl]-4,5-dimethoxy-phenylcarbamoyloxymethyl}-phenoxycarbonylamino)-pentanedioic acid diallyl ester (43)

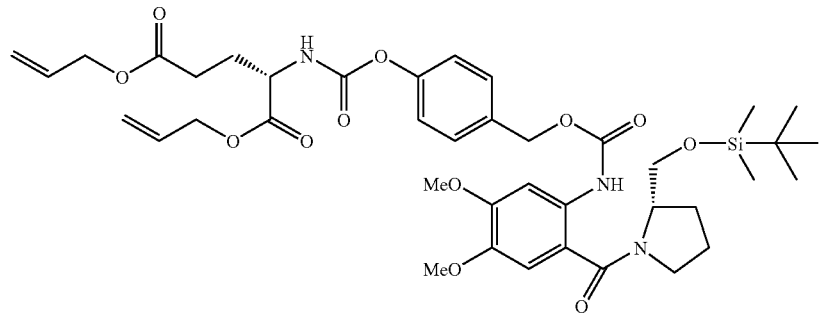

A solution of the carbamate progroup 42 (1.48 g, 3.92 mmol) and triethylamine (0.45 g, 0.6 mL, 4.3 mmol) in anhydrous CH$_2$Cl$_2$ (30 mL) was added to a solution of the isocyanate 7 prepared from the amine 5 (1.54 g, 3.92 mmol), triphosgene (0.42 g, 1.4 mmol) and triethylamine (0.535 g, 0.74 mL, 5.3 mmol) in anhydrous toluene (50 mL). The reaction was complete in 4 h. The product was obtained (flash column chromatography 40% EtOAc/60% n-hexane) as a colourless oil (1.76 g, 56). $^1$H NMR (CDCl$_3$) δ 9.22 (bs, 1H), 7.87 (s, 1H), 7.40 (d, J=10 Hz, 2H), 7.13 (d, J=7.5 Hz, 2H), 6.83 (s, 1H), 5.93 (m, 2H), 5.74 (d, J=8.3 Hz, 1H), 5.30 (m, 4H), 5.17 (d, J=12.5 Hz, 1H), 5.15 (d, J=12.5 Hz, 1H) 4.68 (d, J=5 Hz, 2H) 4.61 (d, J=5 Hz, 1H), 4.48 (m, 1H), 4.35 (m, 1H), 3.95 (s, 3H), 3.82 (s, 3H), 3.65 (m, 1H), 3.50 (m, 2H), 2.55 (m, 2H), 2.30 (m, 1H), 2.1 (m, 3H), 1.95 (m, 1H), 1.8 (m, 1H), 0.9 (s, 9H), 0.04 (s, 6H). IR (neat) 3338, 2953, 2857, 1735, 1615, 1597, 1522 cm$^{-1}$.

{2-[2-tert-Butyl-dimethyl-silanyloxymethyl]-pyrrolidine-1-carbonyl}-4,5-dimethoxy-phenyl}-carbamic acid methyl ester (77)

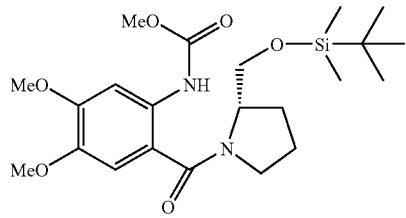

A solution of methanol (0.39 g, 0.5 mL 12.3 mmol) and triethylamine (0.3 g, 0.41 mL, 2.95 mmol) in anhydrous toluene (10 mL) was added to a solution of the isocyanate 7 prepared from the amine 5 (0.97 g, 2.5 mmol), triphosgene (0.263 g, 0.89 mmol) and triethylamine (0.335 g, 0.46 mL, 3.32 mmol) in anhydrous toluene (30 mL). The reaction was complete in 18 hours. The product was obtained (flash column chromatography 60% EtOAc/40% n-hexane) as a colourless oil (0.694 g, 62.5%): [α]$_D^{25}$ –122° (c=0.24, CHCl$_3$); $^1$H NMR (CDCl$_3$) δ 9.1 (bs, 1H), 7.86 (s, 1H), 6.83 (s, 1H), 4.35 (bs, 1H), 4.05 (m, 1H), 3.93 (s, 3H), 3.82 (s, 3H), 3.74 (s, 3H), 3.67 (m, 1H), 3.5 (m, 2H), 2.07 (m, 2H), 1.95 (m, 1H) 1.72 (m, 1H), 0.90 (s, 9H), 0.04 (s, 6H); MS (ES+) m/z (relative intensity) 475.2 (M$^+$. Na, 5), 453.2 (M$^+$. +1, 100); IR (neat) 2953, 1733, 1598, 1524, 1396 cm$^{-1}$.

{2-[2-tert-Butyl-dimethyl-silanyloxymethyl]-pyrrolidine-1-carbonyl}-4,5-dimethoxy-phenyl}-carbamic acid tert-butyl ester (78)

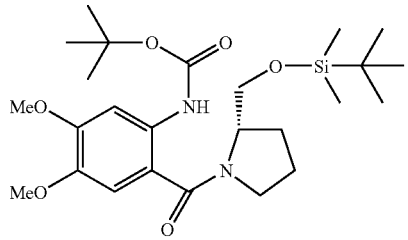

A solution of t-butanol (0.99 g, 1.25 mL 13.3 mmol) and triethylamine (0.292 g, 0.4 mL, 2.9 mmol) in anhydrous toluene (10 mL) was added to a solution of the isocyanate 7 prepared from the amine 5 (1.05 g, 2.66 mmol), triphosgene (0.284 g, 0.96 mmol) and triethylamine (0.36 g, 0.5 mL, 3.6 mmol) in anhydrous toluene (30 mL). The reaction was stirred at room temperature for 18 hours then heated under reflux for 18 h. The product was obtained (flash column chromatography 60% EtOAc/40% n-hexane) as a colourless oil (0.392 g, 30%): [α]$_D^{23.5}$ –90.7° (c=0.193, CHCl$_3$); $^1$H NMR (CDCl$_3$) δ 8.58 (bs, 1H), 7.91 (s, 1H), 6.82 (s, 1H), 4.37 (bs, 1H), 4.13 (m, 1H), 3.95 (s, 3H), 3.82 (s, 3H), 3.68 (m, 1H), 3.51 (m, 2H), 2.05 (m, 2H), 1.93 (m, 1H), 1.74 (m, 1H), 1.61 (s, 9H), 0.97 (s, 9H), 0.04 (s, 6H); MS (ES+) m/z (relative intensity) 517.2 (M$^+$. +Na, 5), 495.2 (M$^+$. +1, 100); IR (neat) 2930, 1723, 1600, 1521, 1420, 1394 cm$^{-1}$.

{2-[2-tert-Butyl-dimethyl-silanyloxymethyl]-pyrrolidine-1-carbonyl}-4,5-dimethoxy-phenyl}-carbamic acid 2,2,2-trichloroethyl ester (79)

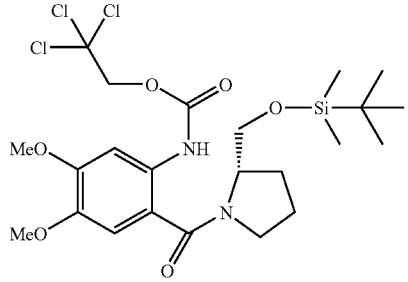

A solution of 2,2,2-trichloroethanol (0.48 g, 0.31 mL 3.2 mmol) and triethylamine (0.36 g, 0.49 mL, 3.5 mmol) in anhydrous toluene (10 mL) was added to a solution of the isocyanate 7 prepared from the amine 5 (1.15 g, 2.92 mmol), triphosgene (0.31 g, 1.05 mmol) and triethylamine (0.398 g, 0.55 mL, 3.94 mmol) in anhydrous toluene (30 mL). The reaction was complete in 18 h. The product was obtained (flash column chromatography 60% EtOAc/40% n-hexane) as a colourless oil (1.075 g, 65%): $[\alpha]_D^{24.2}$ −90.5° (c=0.21, CHCl$_3$); $^1$H NMR (CDCl$_3$) δ 9.48 (bs, 1H), 7.85 (s, 1H), 6.87 (s, 1H), 4.83 (d, J=11.97 Hz, 1H), 4.76 (d, J=12.0 Hz, 1H), 4.39 (bs, 1H), 3.99 (m, 1H), 3.94 (s, 3H), 3.84 (s, 3H), 3.68 (m, 1H), 3.56 (m, 2H), 2.1 (m, 2H), 1.98 (m, 1H), 1.74 (m, 1H), 0.91 (s, 9H), 0.04 (s, 6H); MS (ES+) m/z (relative intensity) 593.0 (M$^+$. +Na, 5), 571.1 (M$^+$. +1, 100); IR (neat) 2953, 1746, 1599, 1524, 1462, 1422, 1397 cm$^{-1}$.

{2-[2-tert-Butyl-dimethyl-silanyloxymethyl]-pyrrolidine-1-carbonyl}-4,5-dimethoxy-phenyl}-carbamic acid 4-nitro benzyl ester (80)

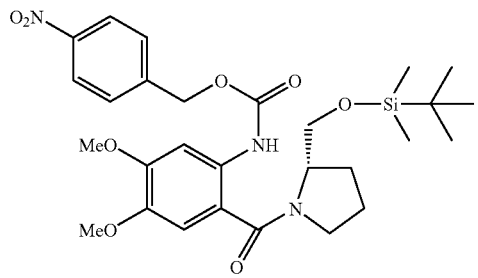

A solution of 4-nitro-benzyl alcohol (0.42 g, 2.75 mmol) and triethylamine (0.3 g, 0.42 mL, 3.0 mmol) in anhydrous dichloromethane (20 mL) was added to a solution of the isocyanate 7 prepared from the amine 5 (0.985 g, 2.5 mmol), triphosgene (0.265 g, 0.895 mmol) and triethylamine (0.34 g, 0.47 mL, 3.36 mmol) in anhydrous toluene (40 mL). The reaction was complete in 18 h. The product was obtained (flash column chromatography 40% EtOAc/60% n-hexane) as a yellow oil (0.87 g, 61%): $[\alpha]_D^{21.0}$ −85.15° (c=0.23, CHCl$_3$); $^1$H NMR (CDCl$_3$) δ 9.48 (bs, 1H), 8.22 (d, J=8.8 Hz, 2H), 7.87 (s, 1H), 7.56 (d, J=8.8 Hz, 2H), 6.86 (s, 1H), 5.26 (2d, J=13.5 Hz, 2H), 4.36 (bs, 1H), 4.0 (m, 1H), 3.93 (s, 3H), 3.83 (s, 3H), 3.67 (m, 1H), 3.55 (m, 2H), 2.06 (m, 2H), 1.97 (m, 1H), 1.75 (m, 1H), 0.90 (s, 9H), 0.03 (s, 6H); MS (ES+) m/z (relative intensity) 482.2 (M$^+$. +Na, 100), 460.3 (M$^+$. +1, 60); IR (neat) 2953, 1728, 1600, 1519, 1397, 1346 cm$^{-1}$.

{2-[2-tert-Butyl-dimethyl-silanyloxymethyl]-pyrrolidine-1-carbonyl}-4,5-dimethoxy-phenyl}-carbamic acid 9H-fluorenyl-9-ylmethyl ester (81)

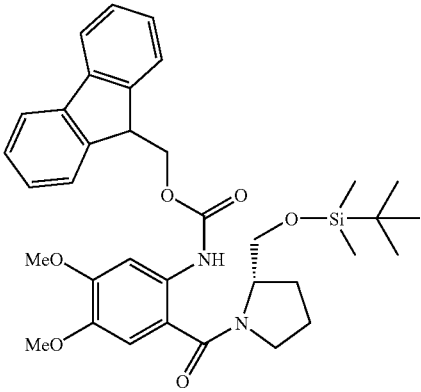

A solution of 9-fluorenylmethanol (0.54 g, 2.7 mmol) and triethylamine (0.3 g, 0.4 mL, 3.0 mmol) in anhydrous toluene (20 mL) was added to a solution of the isocyanate 7 prepared from the amine 5 (0.98 g, 2.5 mmol), triphosgene (0.265 g, 0.895 mmol) and triethylamine (0.34 g, 0.47 mL, 3.36 mmol) in anhydrous toluene (40 mL). The reaction was complete in 18 h. The product was obtained (flash column chromatography 20% EtOAc/80% n-hexane) as a yellow oil (1.04 g, 68%): $[\alpha]_D^{20.8}$ −72.96° (c=0.23, CHCl$_3$); $^1$H NMR (CDCl$_3$) δ 9.32 (bs, 1H), 7.86 (s, 1H), 7.78 (d, J=7.5 Hz, 2H), 7.66 (m, 2H), 7.42 (d, J=7.4 Hz, 2H), 7.34 (d, J=7.4 Hz, 2H), 6.9 (s, 1H), 4.51-4.28 (m, 4H), 4.05 (m, 1H), 3.94 (s, 3H), 3.85 (s, 3H), 3.72 (m, 1H), 3.55 (m, 2H), 2.09 (m, 2H), 1.98 (m, 1H), 1.75 (m, 1H), 0.93 (s, 9H), 0.07 (s, 6H); MS (ES+) m/z (relative intensity) 525.2 (M$^+$. +Na, 100), 503.3 (M$^+$. +1, 55); IR (neat) 2953, 1727, 1600, 1522, 1397, 1346 cm$^{-1}$.

{2-[2-tert-Butyl-dimethyl-silanyloxymethyl]-pyrrolidine-1-carbonyl}-4,5-dimethoxy-phenyl}-carbamic acid allyl ester (82)

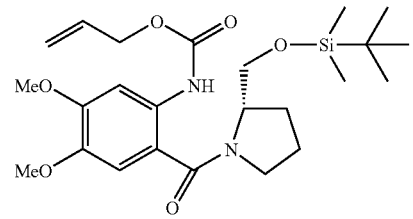

A solution of allyl alcohol (3.73 g, 4.36 mL, 64.15 mmol) and triethylamine (1.56 g, 2.14 mL, 15.4 mmol) in anhydrous toluene (40 mL) was added to a solution of the isocyanate 7 prepared from the amine 5 (5.06 g, 12.8 mmol), triphosgene (1.37 g, 4.62 mmol) and triethylamine (1.75 g, 2.41 mL, 17.3 mmol) in anhydrous toluene (120 mL). The reaction was complete in 48 h. The product was obtained (flash column chromatography 30% EtOAc/70% n-hexane) as a pale yellow oil (4.23 g, 69%): $[\alpha]_D^{20.2}$ −106.7° (c=0.45, CHCl$_3$); $^1$H NMR (CDCl$_3$) δ 9.16 (bs, 1H), 7.88 (s, 1H), 6.84 (s, 1H), 6.00-5.93 (m, 1H), 5.38-5.23 (m, 2H), 4.66-4.63 (m, 2H), 4.36 (bs, 1H), 4.0 (m, 1H), 3.94 (s, 3H), 3.83 (s, 3H), 3.7 (m, 1H), 3.52 (m, 2H), 2.08-2.04 (m, 2H), 1.97 (m, 1H), 1.75 (m, 1H), 0.91 (s, 9H), 0.04 (s, 6H); MS (ES+) m/z (relative intensity) 501.1 (M⁺. +Na, 3), 479.1 (M⁺. +1, 100); Ir (neat) 2953, 2857, 1731, 1622, 1599, 1524, 1397 cm⁻¹

Deprotection of Alcohols

General Methods for the Deprotection of Monomer Tert-Butyldimethylsilyl Ethers and Acetates Method A (TBDMS Ethers)

A 1.0 M THF solution of tetra-N-butyl-ammonium fluoride (1.2 eq.) was added via syringe to a solution of the TBDMS ether (1 eq.) in THF at 0° C. The reaction was stirred at room temperature until reaction was complete (TLC). The solvent was removed in vacuo and the product purified by flash column chromatography.

Method B (TBDMS Ethers)

A solution of the TBDMS ether in a mixture of AcOH/THF/H$_2$O (3/1/1) was stirred at room temperature until reaction was complete (TLC). The reaction mixture was cooled (ice bath) and carefully neutralised with NaHCO$_3$ $_{(aq)}$ (1 eq). The mixture was extracted with EtOAc (x3) the combined extracts were washed with water (x1), satd NaCl $_{(aq)}$ (x1), dried (MgSO$_4$) and evaporated in vacuo. The product was purified by flash column chromatography.

Method C (Acetates)

A solution of K$_2$CO$_3$ (5 eq) in H$_2$O was added dropwise to a solution of the acetate (1 eq) in MeOH/CHCl$_3$. The mixture was stirred at room temperature until reaction was complete (TLC). The solvent was evaporated in vacuo and the aqueous portion washed with EtOAc (x3). The combined organic extracts were washed with satd NaCl $_{(aq)}$ (x3), dried (MgSO$_4$) and evaporated in vacuo. The product was purified by flash column chromatography.

[2-(2-Hydroxymethyl-pyrrolidine-1-carbonyl)-4,5-dimethoxy-phenyl]-carbamic acid-benzyl ester (16)

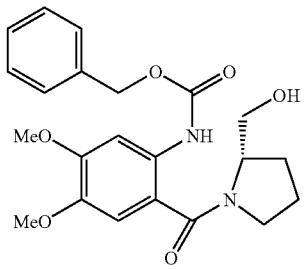

The TBDMS ether 9 (0.517 g, 0.98 mmol) in THF (15 mL) was deprotected (Method A: Bu$_4$NF (1.2 mL, 1.2 mmol)) to give the product (flash column chromatography 90% EtOAc/10% n-hexane) as a colourless oil (0.3 g, 75%).); [α]$_D^{20.2}$–80.6° (c=0.18, CHCl$_3$), ¹H NMR (CDCl$_3$) δ 8.8 (bs, 1H), 7.80 (s, 1H), 7.40 (m, 5H), 6.81 (s, 1H), 5.18 (m, 2H), 4.45 (m, 1H), 4.25 (m, 1H), 3.93 (s, 3H), 3.85 (m, 4H), 3.70 (m, 1H), 3.60 (m, 1H), 3.50 (m, 1H), 2.19 (m, 1H), 1.90 (m, 1H), 1.70 (m, 2H). IR (neat) 3338, 2959, 1727, 1598, 1523 cm⁻¹.

[2-(2-Hydroxymethyl-pyrrolidine-1-carbonyl)-4,5-dimethoxy-phenyl]-carbamic acid-4-methoxy-benzyl ester (17)

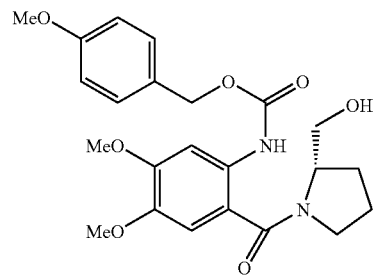

The TBDMS ether 10 (0.37 g, 0.66 mmol) in THF (20 mL) was deprotected (Method A: Bu$_4$NF (0.8 ml, 0.8 mmol)) to give the product (flash column chromatography 80% EtOAc/20% n-hexane, then EtOAc) as a colourless oil (0.29 g, 97%). [α]$_D^{22.1}$–69.6° (c=0.23, CHCl$_3$), ¹H NMR (CDCl$_3$) δ 8.72 (s, 1H), 7.76 (s, 1H), 7.34 (d, J=8.6 Hz, 2H), 6./90 (d, J=8.6 Hz, 2H), 6.80 (s, 1H), 5.10 (m, 2H), 4.40 (m, 1H), 4.30 (m, 1H), 3.92 (s, 3H), 3.83 (s, 3H), 3.80 (m, 4H), 3.7 (m, 1H), 3.58 (m, 1H), 3.45 (m, 1H), 2.15 (m, 1H), 1.90 (m, 1H), 1.70 (m, 2H). IR (neat) 3338, 2958, 2837, 1726, 1599 cm⁻¹.

[2-(2-Hydroxymethyl-pyrrolidine-1-carbonyl)-4,5-dimethoxy-phenyl]-carbamic acid 2-trimethylsilanyl-ethyl ester (18)

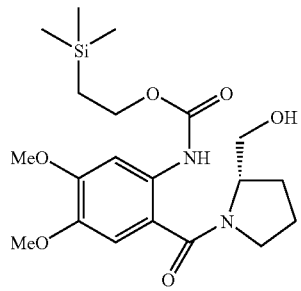

The TBDMS ether 11 (0.354 g, 0.66 mmol) was deprotected (Method B: AcOH (6 mL)/THF (2 mL)/H$_2$O (2 mL) then NaHCO$_3$ (8.77 g, 104.4 mmol) in H$_2$O (100 mL)) to give the product (flash column chromatography 80% EtOAc/20% n-hexane) as a colourless oil (0.27 g, 95%).%). [α]$_D^{22.0}$–91.0° (c=0.21, CHCl$_3$), ¹H NMR (CDCl$_3$) δ 8.62 (s, 1H), 7.80 (s, 1H), 6.81 (s, 1H), 4.42 (m, 1H), 4.30 (m, 1H), 4.22 (m, 2H), 3.93 (s, 3H), 3.85 (m, 4H), 3.70 (m, 1H), 3.60 (m, 1H), 3.50 (m, 1H0, 2.20 (m, 1H), 1.90 (m, 1H) 1.70 (m, 2H), 1.09 (m, 2H), 0.08 (s, 9H). IR (neat) 3340, 2953, 1726, 1597, 1520 cm⁻¹.

51

[2-(2-Hydroxymethyl-pyrrolidine-1-carbonyl)-4,5-dimethoxy-phenyl]-carbamic acid-3-(4-nitrophenyl)-allylester (19)

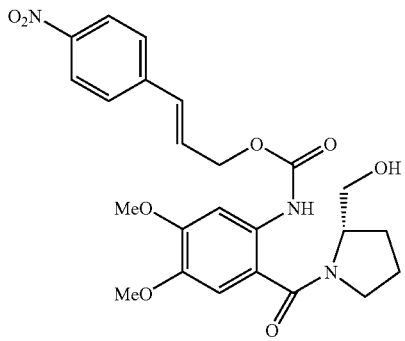

The TBDMS ether 12 (0.346 g, 0.58 mmol) was deprotected (Method B: AcOH (6 mL)/THF (2 mL)/H$_2$O (2 mL) then NaHCO$_3$ (8.77 g, 104.4 mmol) in H$_2$O (100 mL)) to give the product (flash column chromatography EtOAc) as a yellow foam (0.26 g, 92%). [α]$_D^{21.9}$ −61.2° (c=0.24, CHCl$_3$), $^1$H NMR (CDCl$_3$) δ8.95 (s, 1H), 8.20 (d, J=8.8 Hz, 2H), 7.81 (s, 1H), 7.53 (d, J=8.8 Hz, 2H), 6.84 (s, 1H), 6.75 (d, J=16 Hz, 1H), 6.50 (dt, J=5.8, 16 Hz, 1H), 4.84 (m, 2H), 4.43 (m, 1H), 4.25 (m, 1H), 3.94 (s, 3H), 3.86 (m, 4H), 3.75 (m, 1H), 3.65 (m, 1H), 3.55 (m, 1H), 2.70 (m, 2H), 2.20 (m, 1H), 1.90 (m, 1H). IR (neat) 3340, 2939, 1728, 1597, 1519 cm$^{-1}$.

[2-(2-Hydroxymethyl-pyrrolidine-1-carbonyl)-4,5-dimethoxy-phenyl]-carbamic acid 2-benzenesulfonyl-ethyl ester (20)

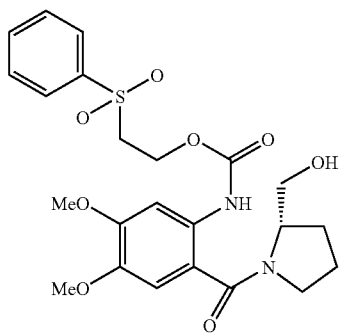

The TBDMS ether 13 (0.3 g, 0.49 mmol) was deprotected (Method B: AcOH (9 mL)/THF (6 mL)/H$_2$O (3 mL) then NaHCO$_3$ (13.16 g, 156.6 mmol) in H$_2$O (175 mL)) to give the product (flash column chromatography 80% EtOAc/20% n-hexane) as a colourless oil (0.13 g, 54%). [α]$_D^{22.0}$ −50.7° (c=0.22, CHCl$_3$, $^1$H NMR (CDCl$_3$) δ 8.79 (s, 1H), 7.80 (s, 1H), 7.40 (m, 4H), 6.82 (s, 1H), 5.20 (d, J=12.3 Hz, 1H), 5.16 (d, J=12.3 Hz, 1H), 4.40 (m, 1H), 4.25 (m, 1H), 3.93 (s, 3H), 3.85 (m, 4H), 3.70 (m, 1H), 3.60 (m, 1H), 3.50 (m, 3H), 2.20 (m, 1H), 1.90 (m, 1H), 1.70 (m, 2H). IR (neat) 3337, 2938, 1729, 1598, 1524 cm$^{-1}$.

52

[2-(2-Hydroxymethyl-pyrrolidine-1-carbonyl)-4,5-dimethoxy-phenyl]-carbamic acid 4,5-dimethoxy-2-nitro-benzyl ester (21)

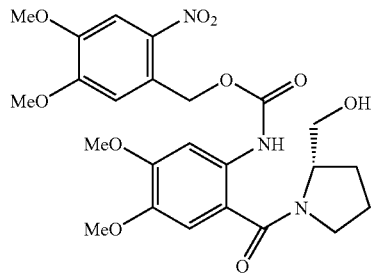

The acetate 14 (2.0 g, 3.5 mmol) in MeOH/CHCl$_3$ (80 mL/30 mL) was deprotected (Method C: K$_2$CO$_3$ (2.45 g, 18.0 mmol) in H$_2$O (50 mL)) to give the product (flash column chromatography 2% MeOH/98% CHCl$_3$) as a yellow foam (1.6 g, 86%).

[α]$_D^{25}$ −59.00 (c=1.0, CHCl$_3$); $^1$H NMR (CDCl$_3$) δ 8.99 (s, 1H), 7.72 (s, 2H), 7.10 (s, 1H), 6.83 (s, 1H), 5.63 (d, J=15.2 Hz, 1H), 5.52 (d, J=15.2 Hz, 1H), 4.38 (bs, 2H), 4.08-3.80 (m, 13H), 3.73-3.44 (m, 2H), 2.25-2.08 (m, 1H), 2.03-1.60 (m, 3H); $^{13}$C NMR (CDCl$_3$) δ 170.6, 153.7, 153.1, 151.1, 148.1, 144.1, 139.6, 131.4, 127.7, 110.7, 110.0, 108.2, 104.6, 66.0, 63.8, 60.8, 56.5, 56.4, 56.0, 51.4, 28.2, 25.0; MS (FAB) m/z 652 (M+Cs), 520 (M+1); IR (neat) 3362, 2960, 1735, 1613, 1519, 1454, 1397, 1321, 1279, 1220, 1174, 1119, 1072, 1034, 990, 958, 880, 847, 795, 758, 708 cm$^{-1}$; HRMS m/z calcd for C$_{24}$H$_{30}$N$_3$O$_{10}$ 520.1946 (M+H) found 520.1931.

4-{4-[2-(2-hydroxymethyl-pyrrolidine-1-carbonyl)-4,5-dimethoxy-phenylcarbamoyloxymethyl]-2-methoxy-5-nitro-phenoxy}-butyric acid methyl ester (22)

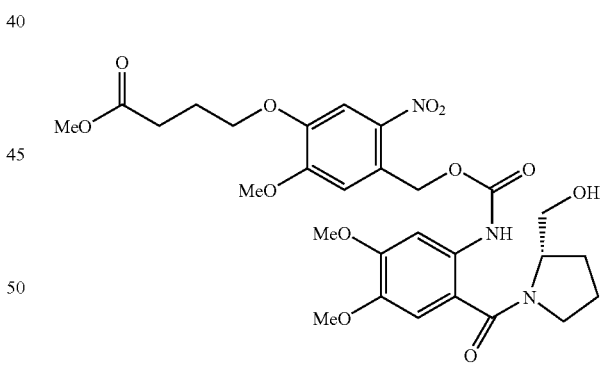

The acetate 15 (1.80 g, 2.7 mmol) in MeOH/CHCl$_3$ (80 mL/30 mL) was deprotected (Method C: K$_2$CO$_3$ (1.83 g, 13.3 mmol) in H$_2$O (50 mL)) to give the methyl ester product as a yellow foam (1.06 g, 63%). [α]$_D^{24}$ −50.0° (c=1.0, CHCl$_3$); $^1$H NMR (CDCl$_3$) δ 8.98 (s, 1H), 7.72 (s, 2H), 7.08 (s, 1H), 6.83 (s, 1H), 5.63 (d, J=15.2 Hz, 1H), 5.52 (d, J=15.0 Hz, 1H), 4.41-4.31 (m, 1H), 4.18-4.09 (m, 3H), 3.97 (s, 3H), 3.91 (s, 3H), 3.85 (s, 3H), 3.66 (s, 3H), 3.62-3.50 (m, 2H), 2.59-2.54 (m, 2H), 2.19 (pent., J=6.7 Hz, 2H), 1.91-1.66 (m, 4H); $^{13}$C NMR (CDCl$_3$) δ 174.3, 171.7, 154.9, 154.1, 151.9, 148.2, 144.8, 140.2, 132.2, 128.5, 119.0, 111.3, 110.8, 110.1, 105.2, 68.3, 66.2, 63.8, 60.9, 56.5, 56.4, 56.0, 51.7, 51.5, 30.3, 28.3, 25.1, 24.2; MS (FAB) m/z 628 (M+Na) 606 (M+1); IR (neat)

3342, 2953, 2615, 1740, 1601, 1531, 1398, 1333, 1285, 1116, 1072, 996, 943, 870, 814, 755 cm$^{-1}$.

2-(3-{4-[2-(2-Hydroxymethyl-pyrrolidine-1-carbonyl)-4,5-dimethoxy-phenylcarbamoyloxymethyl]-phenyl}-ureido)-pentanedioic acid diallyl ester (37)

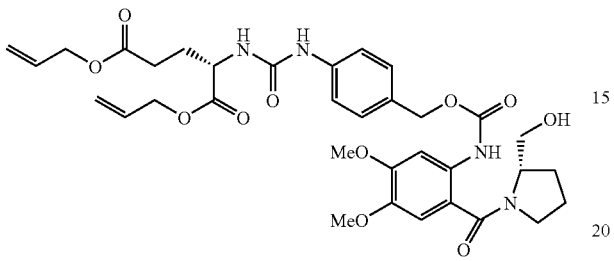

The TBDMS ether 36 (1.88 g, 2.36 mmol) was deprotected (Method B: AcOH (18 mL)/THF (6 mL)/H$_2$O (6 mL) then NaHCO$_3$ (26.3 g, 313.0 mmol) in H$_2$O (270 mL)) to give the product (flash column chromatography 99% EtOAc/MeOH 1%) as a white foam (1.6 g, 99%). $[\alpha]_D^{23.4}$ –45.9° (c=0.21, CHCl$_3$), $^1$H NMR (CDCl$_3$) δ 8.69 (s, 1H), 7.75 (s, 1H), 7.30 (m, 4H), 7.12 (s, 1H), 6.80 (s, 1H), 5.90 (m, 2H), 5.74 (d, J=12.8 Hz, 1H), 5.30 (m, 4H), 5.10 (s, 2H), 4.60 (s, 5H), 4.40 (m, 1H), 4.20 (m, 1H), 3.90 (m, s, 3H), 3.84 (m, 4H), 3.70 (m, 1H), 3.50 (m, 2H), 2.50 (m, 2H), 2.10 (m, 2H), 1.90 (m, 1H), 1.70 (m, 2H). IR (neat) 3350, 2951, 2856, 1734, 1660, 1601, 1518 cm$^{-1}$. HRMS m/z calcd for C$_{39}$H$_{43}$N$_4$O$_{11}$Na 705.2748 (M+Na), found 705.2721.

2-(4-{2-[2-Hydroxymethyl-pyrrolidine-1-carbonyl)-4,5-dimethoxy-phenylcarbamoyloxymethyl]-phenoxycarbonylamino}-pentanedioic acid diallyl ester (44)

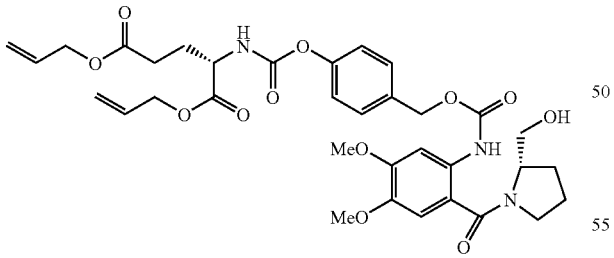

The TBDMS ether 43 (2.17 g, 2.72 mmol) was deprotected (Method B: AcOH (21 mL)/THF (7 mL)/H$_2$O (7 mL) then NaHCO$_3$ (30.66 g, 365.0 mmol) in H$_2$O (400 mL)) to give the product (flash column chromatography EtOAc) as a white foam (1.7 g, 91%). $^1$H NMR (CDCl$_3$) δ 8.77 (s, 1H), 7.68 (s, 1H), 7.42 (d, J=7.5 Hz, 2H), 7.13 (d, J=7.5 Hz, 2H), 6.79 (s, 1H), 5.95 (m, 2H), 5.78 (d, J=6.25 Hz, 1H), 5.30 (m, 4H), 5.17 (d, J=9.4 Hz, 1H), 5.13 (d, J=9.4 Hz, 1H), 4.70 (m, 4H), 4.50 (m, 1H), 4.40 (m, 1H), 4.25 (m, 1H), 3.93 (s, 3H), 3.84 (m, 4H), 3.70 (m, 1H), 3.55 (m, 2H), 2.55 (m, 2H) 2.40 (m, 1H), 2.10 (m, 2H), 1.90 (m, 1H), 1.70 (m, 2H). IR (neat) 3345, 2950, 2856, 1736, 1615, 1598, 1522 cm$^{-1}$.

[2-(2-Hydroxymethyl-pyrrolidine-1-carbonyl)-4,5-dimethoxy-phenyl]-carbamic acid methyl ester (83)

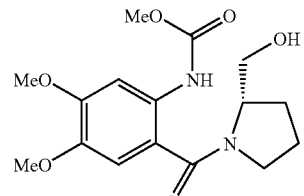

The TBDMS ether 77 (0.67 g, 1.5 mmol) in THF (30 mL) was deprotected (Method A: BU$_4$NF (1.74 mL, 1.74 mmol)) to give the product (flash column chromatography 99% EtOAc/1% MeOH) as a colourless oil (0.46 g, 99%): $[\alpha]_D^{25.5}$ –125.0° (c=0.22, CHCl$_3$); $^1$H NMR (CDCl$_3$) δ 8.72 (bs, 1H), 7.76 (s, 1H), 6.81 (s, 1H), 4.42-4.14 (m, 2H), 3.92 (s, 3H), 3.84 (s+m, 4H), 3.6-3.4 (m, 2H), 2.17 (m, 1H), 1.90-1.62 (m, 3H); MS (ES+) m/z (relative intensity) 361.0 (M$^+$. +Na, 20), 339.1 (M$^+$. +1, 100); IR (neat) 3339, 2953, 1730, 1598, 1524, 1458, 1397 cm$^{-1}$.

[2-(2-Hydroxymethyl-pyrrolidine-1-carbonyl)-4,5-dimethoxy-phenyl]-carbamic acid tert-butyl ester (84)

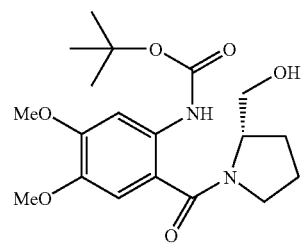

The TBDMS ether 78 (0.34 g, 0.69 mmol) in THF (20 mL) was deprotected (Method A: BU$_4$NF (0.83 mL, 0.83 mmol)) to give the product (flash column chromatography EtOAc) as a colourless oil (0.26 g, 99%): $[\alpha]_D^{24.6}$ –90.4° (c=0.19, CHCl$_3$); $^1$H NMR (CDCl$_3$) δ 8.42 (bs, 1H), 7.81 (s, 1H), 6.80 (s, 1H), 4.43 (m, 1H), 4.28 (bs, 1H), 3.94 (s, 3H), 3.84 (s+m, 4H), 3.76 (m, 1H), 3.62 (m, 1H), 3.51 (m, 1H), 2.17 (m, 1H), 1.91 (m, 1H) 1.85-1.62 (m, 2H), 1.51 (s, 9H); MS (ES+) m/z (relative intensity) 403.1 (M$^+$. +Na, 15), 381.1 (M$^+$. +1, 100); IR (neat) 3340, 2975, 1721, 1597, 1522, 1456, 1395 cm$^{-1}$.

[2-(2-Hydroxymethyl-pyrrolidine-1-carbonyl)-4,5-dimethoxy-phenyl]-carbamic acid 2,2,2-trichloro-ethyl ester (85)

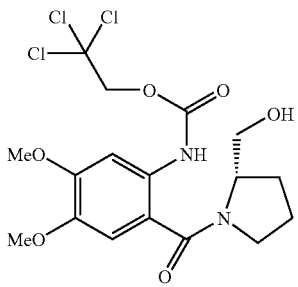

The TBDMS ether 79 (1.03 g, 1.8 mmol) was deprotected (Method B: AcOH (15 mL)/THF (5 mL)/H$_2$O (5 mL) then NaHCO$_3$ (21.9 g, 261 mmol) in H$_2$O (300 mL)) to give the product (crystallised from 80% EtOAc/20% n-hexane) as a white solid (0.8 g, 97%): $[\alpha]_D^{24.3}$ −91.4° (c=0.19, CHCl$_3$); $^1$H NMR (CDCl$_3$) δ 9.04 (bs, 1H), 7.73 (s, 1H), 6.85 (s, 1H), 4.83 (d, J=12.0 Hz, 1H), 4.78 (d, J=12.0 Hz, 1H), 4.44 (m, 1H), 4.05 (m, 1H), 3.93 (s, 3H), 3.86 (s+m, 4H), 3.73 (m, 1H), 3.61-3.5 (m, 2H), 2.04 (m, 1H), 1.92 (m, 1H), 1.73 (m, 2H); MS (ES+) m/z (relative intensity) 477.0 (M$^+$ +Na, 30), 455.0 (M$^+$ +1, 100); IR (neat) 3306, 2954, 1743, 1599, 1524, 1432, 1396 cm$^{-1}$.

[2-(2-Hydroxymethyl-pyrrolidine-1-carbonyl)-4,5-dimethoxy-phenyl]-carbamic acid 4-nitro-benzyl ester (86)

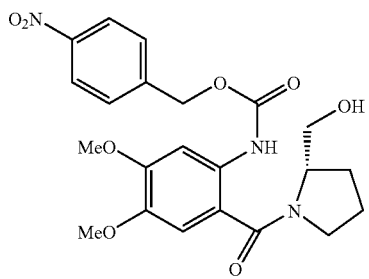

The TBDMS ether 80 (0.81 g, 1.4 mmol) was deprotected (Method B: AcOH (15 mL)/THF (5 mL)/H$_2$O (5 mL) then NaHCO$_3$ (21.9 g, 261 mmol) in H$_2$O (300 mL)) to give the product (flash column chromatography EtOAc) as a pale yellow oil (0.61 g, 94%): $[\alpha]_D^{22.0}$ −60.42° (c=0.24, CHCl$_3$); $^1$H NMR (CDCl$_3$) δ 9.05 (bs, 1H), 8.23 (d, J=8.8 Hz, 2H), 7.78 (s, 1H), 7.56 (d, J=8.8 Hz, 2H), 6.84 (s, 1H), 5.27 (m, 2H), 4.42 (m, 1H), 4.15 (m, 1H), 3.93 (s, 3H), 3.85 (s+m, 4H), 3.71 (m, 1H), 3.62 (m, 1H), 3.51 (m, 1H), 2.17 (m, 1H), 1.91 (m, 1H) 1.71 (m, 2H); MS (ES+) m/z (relative intensity) 482.2 (M$^+$ +Na, 100), 460.3 (M$^+$ +1, 60); IR (neat) 3322, 2941, 1727, 1596, 1517, 1453, 1428, 1395, 1343 cm$^{-1}$.

[2-(2-Hydroxymethyl-pyrrolidine-1-carbonyl)-4,5-dimethoxy-phenyl]-carbamic acid 9H-fluoren-9-ylmethyl ester (87)

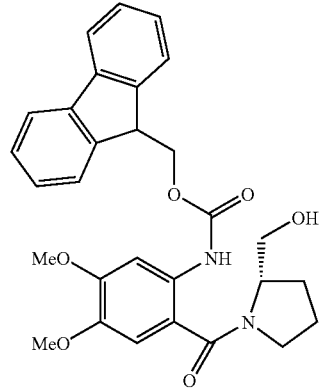

The TBDMS ether 81 (0.98 g, 1.6 mmol) was deprotected (Method B: AcOH (15 mL)/THF (5 mL)/H$_2$O (5 mL) then NaHCO$_3$ (21.9 g, 261 mmol) in H$_2$O (300 mL)) to give the product (flash column chromatography EtOAc) as a colourless oil (0.79 g, 99%): $[\alpha]_D^{21.6}$ −60.5° (c=0.314, CHCl$_3$); $^1$H NMR (CDCl$_3$) δ 8.8 (bs, 1H), 7.78 (d, J=7.5 Hz, 2H), 7.75 (bs, 1H), 7.65 (m, 2H), 7.42 (t, J=7.5 Hz, 2H), 7.33 (t, J=7.5 Hz, 2H), 6.85 (s, 1H), 4.55-4.38 (m, 3H), 4.3 (m, 1H), 4.05 (m, 1H), 3.93 (s, 3H), 3.86 (s+m, 4H), 3.7 (m, 1H), 3.59 (m, 1H), 3.45 (m, 1H), 2.2 (m, 1H), 1.92 (m, 1H), 1.82-1.65 (m, 2H); MS (ES+) m/z (relative intensity) 525.2 (M$^+$ +Na, 100), 503.3 (M$^+$ +1, 60); IR (neat) 3328, 2948, 1722, 1596, 1520, 1449, 1394 cm$^{-1}$.

[2-(2-Hydroxymethyl-pyrrolidine-1-carbonyl)-4,5-dimethoxy-phenyl]-carbamic acid allyl ester (88)

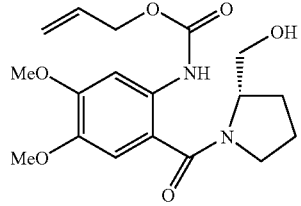

The TBDMS ether 82 (1.44 g, 3.0 mmol) in THF (30 mL) was deprotected (Method A: Bu$_4$NF (13.6 mL, 3.6 mmol)) to give the product (flash column chromatography 80% EtOAc/20% n-hexane) as a colourless oil (0.996 g, 91%): $[\alpha]_D^{24.1}$ −101.7° (c=0.35, CHCl$_3$); $^1$H NMR (CDCl$_3$) δ 8.74 (bs, 1H), 7.79 (s, 1H), 6.82 (s, 1H), 5.96 (m, 1H), 5.27 (m, 2H), 4.86 (m, 2H), 4.41 (m, 1H), 4.15 (m, 1H), 3.93 (s, 3H), 3.84 (s+m, 4H), 3.80-3.45 (m, 3H), 2.2 (m, 1H), 1.95-1.60 (m, 3H); HRMS m/z calcd for C$_{18}$H$_{25}$N$_2$O$_6$ 365.1713 (M+H) found 365.1699; IR (neat) 3337, 2940, 1728, 1598, 1524, 1455, 1396 cm$^{-1}$.

Cyclisation of Monomer Alcohols

General Methods:

Method A

The alcohol (1 eq), (diacetoxyiodo)benzene (1.1 eq) and TEMPO (0.1 eq) were dissolved in CH$_2$Cl$_2$ and the mixture stirred at room temperature until reaction was complete (TLC). The reaction mixture was washed with satd NaHSO$_3$ $_{(aq)}$ (x1) and the NaHSO$_3$ portion was then washed with CH$_2$Cl$_2$ (x4). The combined organic extracts were washed with satd NaHCO$_{3\ (aq)}$ (x2), satd NaCl$_{(aq)}$ (x1), dried (MgSO$_4$) and evaporated in vacuo. The product was purified by either flash column chromatography or recrystallisation.

Method B

The alcohol (1 eq), pyridinium dichromate (1.2 eq) and 4 Å molecular sieves (0.5 g/mmol alcohol) in anhydrous CH$_2$Cl$_2$ were stirred at room temperature under a N$_2$ atmosphere until reaction was complete (TLC). The reaction mixture was filtered through celite, washing with EtOAc. The solvent was evaporated in vacuo and the product purified by flash column chromatography.

(11S,11aS)-7,8-Dimethoxy-11-hydroxy-5-oxo-1,2,3,10,11,11a-hexahydro-5H-pyrrolo[2,1-c][1,4]benzodiazepine-10-carboxylic acid benzyl ester (23)

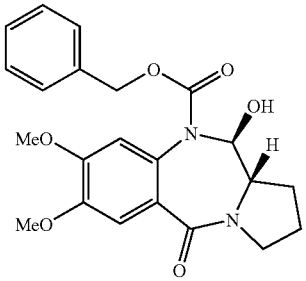

The alcohol 16 (0.136 g, 0.33 mmol) was reacted (Method A) with DAIB (0.127 g, 0.39 mmol) and TEMPO (0.005 g, 0.033 mmol) in CH$_2$Cl$_2$ (6 mL). The product was obtained (flash column chromatography 90% EtOAc/10% n-hexane) as a white foam (0.095 g, 70%). [α]D$^{20.2}$+195.7° (c=0.23, CHCl$_3$), $^1$H NMR (CDCl$_3$) δ 7.30 (m, 3H), 7.24 (m, 3H), 6.52 (s, 1H), 5.64 (m, 1H), 5.50 (d, J=12.3 Hz, 1H), 4.85 (d, J=12.3 Hz, 1H), 3.92 (s, 3H), 3.70 (m, 5H), 3.60 (m, 1H), 3.50 (m, 1H), 2.15 (m, 2H), 2.00 (m, 2H). IR (neat) 3563, 3294, 2953, 1698, 1597, 1573, 1515 cm$^{-1}$.

(11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid 4-methoxy-benzyl ester (24)

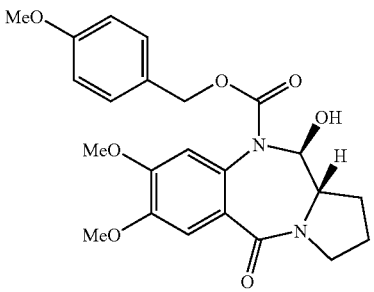

The alcohol 17 (0.214 g, 0.48 mmol) was reacted (Method A) with DAIB (0.175 g, 0.55 mmol) and TEMPO (0.007 g, 0.048 mmol) in CH$_2$Cl$_2$ (6 mL). The product was obtained (flash column chromatography 80% EtOAc/20% n-hexane) as a colourless foam (0.201 g, 94%). [α]$_D$$^{21.5}$+185.8° (c=0.22, CHCl$_3$), $^1$H NMR (CDCl$_3$) δ 7.27 (s, 1H), 7.17 (d, J=7.5 Hz, 2H), 6.83 (d, J=8 Hz, 2H), 6.49 (s, 1H) 5.62 (m, 1H) 5.32 (d, J=12 Hz, 1H), 4.79 (d, J=12 Hz, 1H), 3.92 (s, 3H), 3.78 (s, 3H), 3.70 (m, 4H), 3.55 (m, 1H), 3.45 (m, 1H), 2.15 (m, 2H), 2.00 (m, 2H), IR (neat) 3369, 2958, 1705, 1606, 1515 cm$^{-1}$.

(11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid 2-trimethylsilanyl-ethyl ester (25)

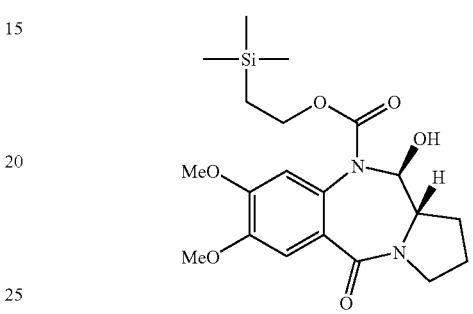

The alcohol 18 (0.110 g, 0.26 mmol) was reacted (Method A) with DAIB (0.092 g, 0.285 mmol) and TEMPO (0.004 g, 0.026 mmol) in CH$_2$Cl$_2$ (3 mL). The product was obtained (flash column chromatography 80% EtOAc/20% n-hexane) as a colourless oil (0.106 g, 97%). [α]$_D$$^{21.9}$+145.0° (c=0.21, CHCl$_3$), $^1$H NMR (CDCl$_3$) δ 7.23 (s, 1H), 6.66 (s, 1H), 5.62 (m, 1H), 4.25 (m, 1H), 4.15 (m, 1H), 3.92 (s, 3H), 3.88 (s, 3H), 3.70 (m, 2H), 3.50 (m, 2H), 2.15 (m, 2H), 2.10 (m, 2H), 0.9 (m, 2H), 0.0 (s, 9H). IR (neat) 3370, 2953, 1704, 1623, 1605, 1515. cm$^{-1}$.

(11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid 3-(4-nitro-phenyl)-allyl ester (26)

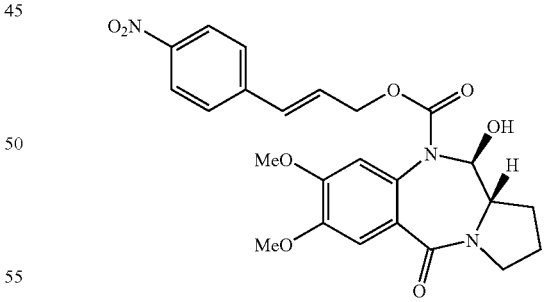

The alcohol 19 (0.253 g, 0.52 mmol) was reacted (Method A) with DAIB (0.185 g, 0.57 mmol) and TEMPO (0.008 g, 0.052 mmol) in CH$_2$Cl$_2$ (4 mL). The product was recrystallised (EtOAc/n-hexane) to give a pale yellow solid (0.24 g, 94%). [α]$_D$$^{23.8}$+172.3° (c=0.21, CHCl$_3$), $^1$H NMR (CDCl$_3$) δ 8.17 (d, J=8.5 Hz, 2H), 7.44 (d, J=7.9 Hz, 2H) 7.27 (s, 1H) 6.71 (s, 1H), 6.47 (m 1H), 6.3 (m, 1H), 5.67 (m, 1H), 4.77 (s, 2H), 3.94 (s, 3H), 3.85 (s, 3H), 3.70 (m, 2H), 3.60 (m, 1H), 3.55 (m, 1H), 2.15 (m, 2H), 2.05 (m, 2H), IR (neat) 3369, 2957, 1709, 1602, 1516. cm$^{-1}$

(11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid 2-benzenesulfonylethyl ester (27)

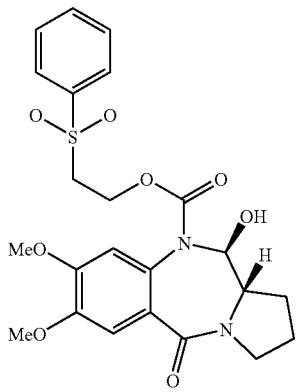

The alcohol 20 (0.102 g, 0.21 mmol) was reacted (Method A) with DAIB (0.080 g, 0.25 mmol) and TEMPO (0.003 g, 0.021 mmol) in $CH_2Cl_2$ (5 mL). The product was obtained (flash column chromatography 80% EtOAc/20% n-hexane) as a colourless oil (0.072 g, 72%). $[\alpha]_D^{24.3}$ +127.5° (c=0.22, $CHCl_3$), $^1H$ NMR ($CDCl_3$) δ 7.75 (m, 5H), 7.22 (m, 1H), 6.95 (m, 1H), 5.65 (m, 1H), 4.70 (m, 2H), 3.95 (s, 6H), 3.60 (m, 5H), 3.25 (m, 1H), 2.15 (m, 2H), 2.05 (m, 2H), IR (neat) 3369, 2971, 1710, 1622, 1604, 1516. $cm^{-1}$

(11S,11aS)-7,8-Dimethoxy-11-hydroxy-5-oxo-1,2,3,10,11,11a-hexahydro-5H-pyrrolo[2,1-c][1,4]benzodiazepine-10-carboxylic acid 4,5-dimethoxy-2-nitrobenzyl ester (28)

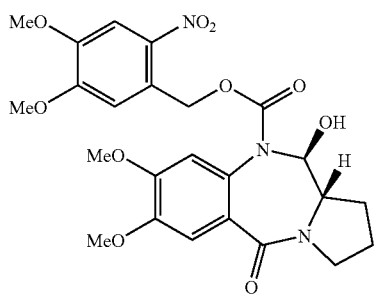

The alcohol 21 (1.70 g, 3.3 mmol) was reacted (Method B) with pyridinium dichromate (1.47 g, 3.9 mmol) and 4 Å molecular sieves (1.63 g) in anhydrous $CH_2Cl_2$ (50 mL). The product was obtained (flash column chromatography 50% EtOAc/50% n-hexane) as a yellow foam (1.04 g, 62%).

$[\alpha]_D^{26}$ +99.00 (c=1.0, $CHCl_3$); $^1H$ NMR ($CDCl_3$) δ 7.65 (s, 1H), 7.25 (s, 1H), 6.83 (s, 1H), 6.51 (s, 1H), 5.74-5.72 (m, 1H), 5.51 (d, J=15.4 Hz, 1H), 5.44 (d, J=15.5 Hz, 1H), 4.51 (bs, 1H), 3.92-3.87 (m, 9H), 3.68 (s, 3H), 3.54-3.50 (m, 2H), 2.16-2.02 (m, 4H); $^{13}C$ NMR ($CDCl_3$) δ 166.8, 155.4, 153.8, 150.9, 148.5, 148.0, 138.8, 128.2, 126.8, 126.1, 112.5, 110.3, 109.2, 107.9, 86.1, 65.3, 60.1, 56.3, 56.2, 56.2, 56.1, 46.4, 28.6, 23.0; MS (FAB) m/z 650 (M+Cs), 540 (M+Na, 20), 518 (M+1); IR (neat) 3362, 2941, 2616, 1715, 1620, 1523, 1436, 1284, 1134, 1104, 1068, 969, 924, 873, 837, 792, 768, 736, 684, 646 $cm^{-1}$; HRMS (FAB) m/z calcd for $C_{24}H_{28}N_3O_{10}$ 518.1761 (M+H) found 518.1775.

(11S,11aS)-7,8-dimethoxy-11-hydroxy-5-oxo-1,2,3,10,11,11a-hexahydro-5H-pyrrolo[1,2-c][1,4]benzodiazepine-10-carboxylic acid 5-methoxy-4-(3-methoxycarbonyl-propoxy)-2-nitro-benzyl ester (29)

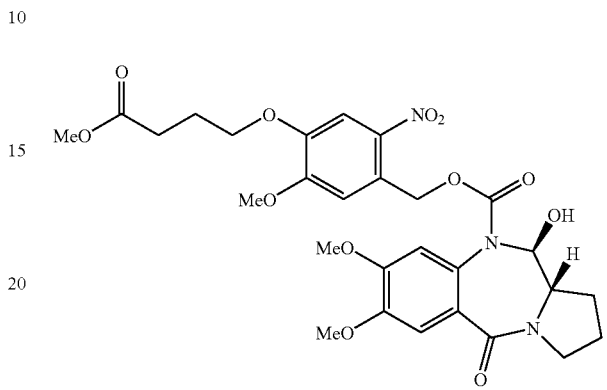

The alcohol 22 (1.06 g, 1.7 mmol) was reacted (Method B) with pyridinium dichromate (0.76 g, 2.0 mmol) and 4 Å molecular sieves (0.84 g) in anhydrous $CH_2Cl_2$ (70 mL). The product was obtained (flash column chromatography 50% EtOAc/50% n-hexane) as a yellow foam (0.553 g, 52%).

$[\alpha]_D^{25}$ +92.50 (c=1.0, $CHCl_3$); $^1H$ NMR ($CDCl_3$) δ 7.64 (s, 1H), 7.25 (s, 1H), 6.82 (s, 1H), 6.50 (s, 1H), 5.74-5.71 (m, 1H), 5.49 (d, J=15.3 Hz, 1H), 5.44 (d, J=15.0 Hz, 1H), 4.17-4.05 (m, 4H), 3.96-3.83 (m, 7H), 3.73-3.65 (m, 6H), 3.59-3.48 (m, 2H), 2.58-2.50 (m, 2H), 2.19-2.10 (m, 4H); $^{13}C$ NMR ($CDCl_3$) δ 172.3, 170.1, 165.8, 154.4, 153.2, 149.9, 147.5, 146.2, 137.7, 127.3, 125.1, 111.5, 109.4, 108.5, 108.4, 85.2, 67.2, 64.3, 55.2, 55.1, 50.7, 45.4, 29.2, 27.7, 23.2, 22.1; MS (FAB) m/z 626 (M+Na), 604 (M+1); IR (neat) 3385, 2955, 2616, 1734, 1638, 1523, 1285, 1104, 1066, 970, 942, 873, 836, 818, 789, 767, 735, 683, 646 $cm^{-1}$.

2-{3-[4-((11S,11aS)-7,8-dimethoxy-11-hydroxy-5-oxo-1,2,3,10,11,11a-hexahydro-5H-pyrrolo[2,1-c][1,4]benzodiazepine-10-carbonyloxymethyl)-phenyl]-ureido}-pentanedioic acid diallyl ester (38)

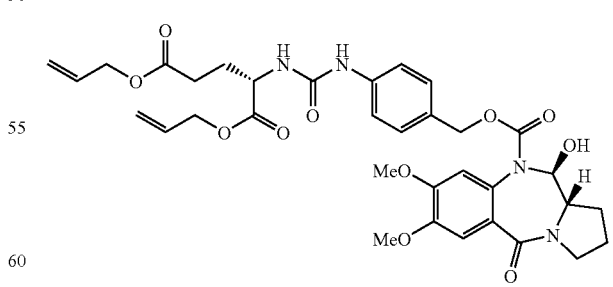

The alcohol 37 (0.99 g, 1.45 mmol) was reacted (Method B) with pyridinium dichromate (0.66 g, 1.74 mmol) and 4 Å molecular sieves (0.87 g) in anhydrous $CH_2Cl_2$ (9 mL). The product was obtained (flash column chromatography 90% EtOAc/10% n-hexane) as a white foam (0.565 g, 57%).

[α]$_D^{25.6}$+90.0° (c=0.19, CHCl$_3$), $^1$H NMR (CDCl$_3$) δ 7.40 (s, 1H), 7.15 (m, 5H), 6.85 (s, 1H), 5.90 (m, 3H), 5.65 (m, 1H), 5.35 (m, 5H), 4.85 (d, J=11.4 Hz, 1H), 4.60 (m, 4H), 4.25 (m, 1H), 4.11 (d, 7.1 Hz, 1H), 3.91 (m, 3H), 3.60 (m, 7H), 2,5 (m, 2H), 2.25 (m, 1H), 2.05 (m, 4H). HRMS m/z calcd for C$_{34}$H$_{41}$N$_4$O$_{11}$ 681.2772 (M+H), found 681.2755.

2-[4-((11S,11aS)-7,8-dimethoxy-11-hydroxy-5-oxo-1,2,3,10,11,11a-hexahydro-5H-pyrrolo[2,1-c][1,4]benzodiazepine-10-carbonyloxymethyl)-phenoxycarbonylamino]-pentanedioic acid diallyl ester (45)

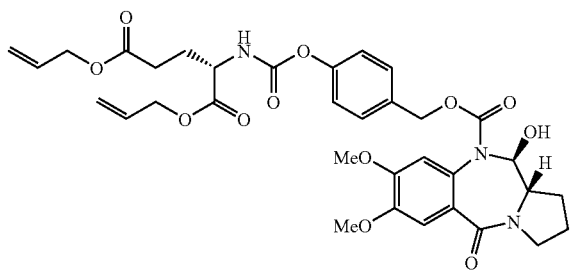

The alcohol 44 (0.55 g, 0.8 mmol) was reacted (Method B) with pyridinium dichromate (0.36 g, 0.96 mmol) and 4 Å molecular sieves (0.4 g) in anhydrous CH$_2$Cl$_2$ (4 mL). The product was obtained (flash column chromatography 80% EtOAc/20% n-hexane) as a white foam (0.36 g, 66%). $^1$H NMR (CDCl$_3$) δ 7.22 (m, 3H), 7.07 (d, J=7.5 Hz, 2H), 6.50 (s, 1H), 5.95 (m, 3H), 5.70 (dd, J=3, 10 Hz, 1H); 5.30 (m, 5H), 4.90 (d, J=13 Hz, 1H), 4.60 (m, 4H), 4.45 (m, 1H), 3.92 (s, 3H), 3.55 (m, 8H), 2.50 (m, 2H), 2.30 (m, 1H), 2.10 (m, 4H).

(11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid methyl ester (89)

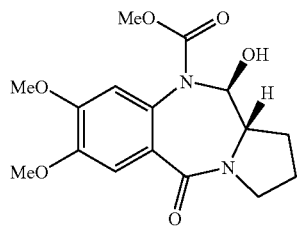

The alcohol 83 (0.41 g, 1.2 mmol) was reacted (Method A) with DAIB (0.47 g, 1.45 mmol) and TEMPO (0.02 g, 0.12 mmol) in CH$_2$Cl$_2$ (30 mL). The product was obtained (trituration with Et$_2$O) as a white solid (0.34 g, 84%): [α]$_D^{21.3}$+173.6° (c=0.24, CHCl$_3$); $^1$H NMR (CDCl$_3$) δ 7.3 (s, 1H), 6.68 (s, 1H), 5.66 (m, 1H), 3.96 (s, 3H), 3.91 (s, 3H), 3.85-3.65 (m, 4H), 3.6 (m, 1H), 3.49 (m, 1H), 2.14 (m, 2H), 2.02 (m, 2H), 1.85 (bs, 1H); MS (ES+) m/z (relative intensity) 337.1 (M$^+$. +1, 100); IR (neat) 3216, 2957, 1719, 1604, 1519, 1477, 1437, 1316 cm$^1$.

(11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid tert-butyl ester (90)

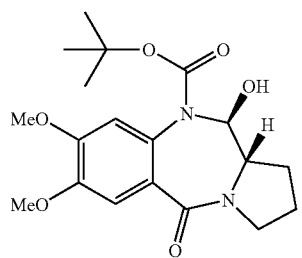

The alcohol 84 (0.23 g, 0.6 mmol) was reacted (Method A) with DAIB (0.234 g, 0.73 mmol) and TEMPO (0.009 g, 0.06 mmol) in CH$_2$Cl$_2$ (10 mL). The product was obtained (flash column chromatography EtOAc) as a white foam (0.205 g, 89%): [α]$_D^{20.9}$+162.4° (c=0.19, CHCl$_3$); $^1$H NMR (CDCl$_3$) δ 7.22 (s, 1H), 6.62 (s, 1H), 5.45 (dd, J=3.2 Hz, 9.5 Hz, 1H), 3.93 (s, 3H), 3.89 (s, 3H), 3.8-3.69 (m, 2H), 3.58 (m, 1H), 3.45 (m, 1H), 2.12 (m, 2H), 2.0 (m, 2H), !0.39 (s, 9H); (ES+) m/z (relative intensity) 379.1 (M$^+$. +1, 100); IR (neat) 3300, 2970, 1701, 1603, 1513, 1432, 1323 cm$^{-1}$.

(11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid 2,2,2-trichloro-ethyl ester (91)

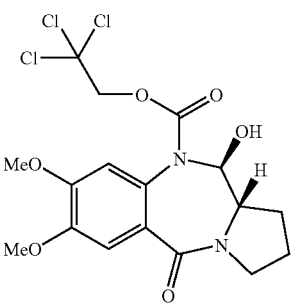

The alcohol 85 (0.715 g, 1.57 mmol) was reacted (Method A) with DAIB (0.61 g, 1.88 mmol) and TEMPO (0.025 g, 0.16 mmol) in CH$_2$Cl$_2$ (30 mL). The product was obtained (crystallised from Et$_2$O) as a white solid (0.56 g, 78%): [α]$_D^{20.7}$+129.2° (c=0.24, CHCl$_3$); $^1$H NMR (CDCl$_3$) δ 7.25 (s, 1H), 6.80 (s, 1H), 5.66 (dd, J=4.22 Hz, 9.8 Hz, 1H), 5.26 (d, J=12 Hz, 1H), 4.23 (d, J=12 Hz, 1H), 3.93 (s, 3H), 3.91 (s, 3H), 3.79 (d, J=4.4 Hz, 1H), 3.7 (m, 1H), 3.5 (m, 2H), 2.14 (m, 2H), 2.02 (m, 2H); (ES$^+$) m/z (relative intensity) 452.9 (M$^+$. +1, 100); IR (neat) 3307, 2958, 1722, 1617, 1599, 1512, 1453, 1432, 1408 cm$^{-1}$.

(11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid 4-nitro-benzyl ester (92)

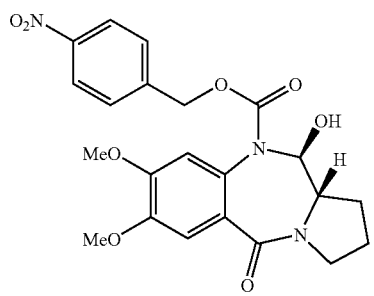

The alcohol 86 (0.7 g, 1.5 mmol) was reacted (Method A) with DAIB (0.585 g, 1.82 mmol) and TEMPO (0.024 g, 0.15 mmol) in CH$_2$Cl$_2$ (40 mL). The product was obtained (flash column chromatography EtOAc) as a yellow foam (0.49 g, 71%): $[\alpha]_D^{21.3}$+174° (c=0.2, CHCl$_3$); $^1$H NMR (CDCl$_3$) δ 8.16 (d, J=8.3 Hz, 2H), 7.32 (d, J=8.0 Hz, 2H), 6.63 (s, 1H), 5.66 (dd, J=4.3 Hz, 9.6 Hz, 1H), 5.32 (d, J=13.5 Hz, 1H), 5.08 (d, J=13.6 Hz, 1H), 3.94 (s, 3H), 3.80 (s, 3H), 3.7 (m, 1H), 3.51 (m, 3H), 2.14 (m, 2H), 1.99 (m, 2H); (ES+) m/z (relative intensity) 480.0 (M$^+$. +Na, 38) 458.1 (M$^+$. +1, 100); IR (neat) 3312, 2968, 1709, 1602, 1513, 1431, 1402 cm$^{-1}$.

(11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid 9H-fluoren-9-ylmethyl ester (93)

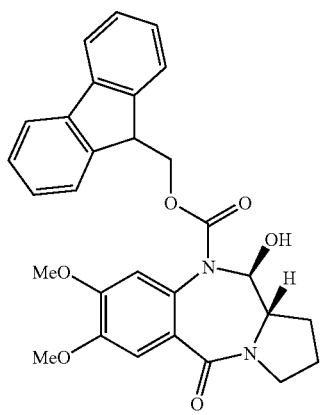

The alcohol 87 (0.735 g, 1.46 mmol) was reacted (Method A) with DAIB (0.565 g, 1.75 mmol) and TEMPO (0.023 g, 0.15 mmol) in CH$_2$Cl$_2$ (40 mL). The product was obtained (flash column chromatography EtOAc) as a yellow oil (0.64 g, 88%): $[\alpha]_D^{21.5}$+113.3° (c=0.20, CHCl$_3$); $^1$H NMR (CDCl$_3$) δ 7.72 (m, 2H), 7.48-7.0 (m, 7H), 6.68 (s, 1H), 5.7 (m, 1H), 4.55 (m, 1H), 4.15-3.9 (m, 5H), 3.85-3.65 (m, 4H), 3.65-3.45 (m, 3H), 2.14 (m, 2H), 2.03 (m, 2H); (ES+) m/z (relative intensity) 501.1 (M$^+$. +1, 100); IR (neat) 3307 2961, 1702, 1602, 1512, 1450, 1406 cm$^{-1}$.

(11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid allyl ester (94)

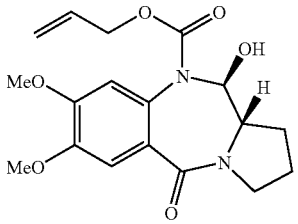

Dimethyl sulfoxide (1.16 g, 1.1 mL, 14.9 mmol, 5 eq) was added to a solution of cyanuric chloride (0.55 g, 3.0 mmol 1.2 eq) in anhydrous THF (20 mL) at −30° C. under a nitrogen atmosphere. The solution was stirred at −30° C. for 30 min. A solution of the alcohol 88 in anhydrous THF (10 mL) was added dropwise followed by triethylamine (1.25 g, 1.73 mL, 12.4 mmol, 5 eq). After 15 min at −30° C. the solution was allowed to reach room temperature. The solvent was evaporated in vacuo and the residue dissolved in dichloromethane (50 mL), extracted with 1M HCl (3×30 mL), H$_2$O (2×30 mL), brine (50 mL), dried (MgSO$_4$) and evaporated in vacuo to give a white foam. The product was recrystallised (EtOAc) to give white needles (0.57 g, 64%) Mp 211-212° C.; $[\alpha]_D^{23.6}$+178.6° (c=0.2, CHCl$_3$); $^1$H NMR (CDCl$_3$) δ 7.24 (s, 1H), 6.68 (s, 1H), 5.80 (m, 1H), 5.63 (m, 1H), 5.13 (m, 2H), 4.67 (m, 1H) 4.43 (m, 1H), 3.92 (2s, 4H), 3.76 (s, 3H), 3.69 (m, 1H), 3.60-3.44 (m, 2H), 2.11 (m, 2H), 2.01 (m, 2H); HRMS m/z calcd for C$_{18}$H$_{23}$N$_2$O$_6$ 33.1556 (M+H), found 363.1564.

Deprotection of Groups in Compounds 38 and 45

2-{3-[4-((11S,11aS)-7,8-Dimethoxy-11-hydroxy-5-oxo-1,2,3,10,11,11a-hexahydro-5H-pyrrolo[2,1-c][1,4]benzodiazepine-10-carbonyloxymethyl)-phenyl]-ureido}-pentanedioic acid (39)

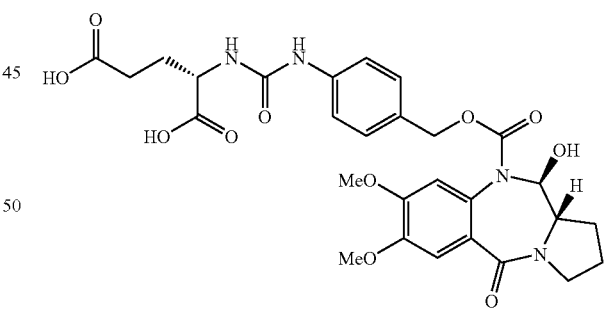

A solution of the diallyl ester 38 (0.5 g, 0.74 mmol, 1 eq), Pd(PPh$_3$)$_4$ (0.043 g, 0.037 mmol, 0.05 eq) and pyrrolidine (0.26 g, 0.31 mL, 3.7 mmol, 5 eq) in anhydrous CH$_2$Cl$_2$ (15 mL) was stirred at room temperature for 1 h and the solvent removed in vacuo. The residue was washed with EtOAc (3×15 mL), dissolved in MeOH (5 mL) and passed down an IRC 50, weakly acidic, ion exchange column, eluting with MeOH (100 mL). The solvent was removed in vacuo to give the product as a white foam (0.39 g, 87%). $[\alpha]_D^{26.4}$+146.0° (c=0.21, EtOH), $^1$H NMR (d$_6$ DMSO) δ 8.82 (s, 1H), 7.32 (d, J=7.12 Hz, 2H), 7.11 (d, J=7.52 Hz, 2H), 7.04 (s, !H), 6.69 (s, 1H), 6.50 (d, J=6.6 Hz, 1H), 5.47 (d, J=9.16 Hz, 1H), 5.14 (d, J=12 Hz, 1H), 4.75 (d, J=12 Hz, 1H), 4.11 (m, 1H), 3.78 (m, 5H), 3.69 (s, 3H), 3.40 (m, 4H), 2.27 (t, J=7.5 Hz, 2H), 1.95 (m, 4H). HRMS m/z calcd for $C_{28}H_{33}N_4O_{11}$ 601.2146 (M+H), found 601.2160.

2-[4-((11S,11aS)-7,8-Dimethoxy-11-hydroxy-5-oxo-1,2,3,10,11,11a-hexahydro-5H-pyrrolo[2,1-c][1,4]benzodiazepine-10-carbonyloxymethyl)-phenoxycarbonylamino]-pentanedioic acid (46)

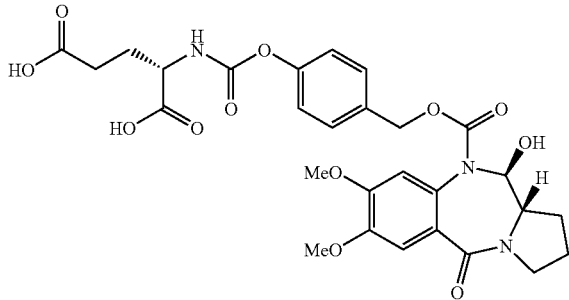

A solution of the diallyl ester 45 (0.596 g, 0.95 mmol, 1 eq), Pd(PPh$_3$)$_4$ (0.055 g, 0.047 mmol, 0.05 eq) and pyrrolidine (0.34 g, 0.39 mL, 4.7 mmol, 5 eq) in anhydrous $CH_2Cl_2$ (18 mL) was stirred at room temperature for 1 h and the solvent removed in vacuo. The residue was washed with EtOAc (3×15 mL), dissolved in MeOH (15 mL) and passed down an IRC 50, weakly acidic, ion exchange column, eluting with MeOH (80 mL). The solvent was removed in vacuo to give the product as a white foam (0.46 g, 88%). $^1$H NMR (d$_6$ DMSO) δ 7.95 (d, J=6.25 Hz, 1H), 7.33 (d, J=8 Hz, 2H), 7.10 (m, 3H) 6.73 (s, 1H), 5. 49 (d, J=9.2 Hz, 1H), 5.2 (d, J=12.5 Hz, 1H), 4.89 (d, J=12.75 Hz, 1H), 4.00 (m, 1H), 3.80 (m, 7H), 3.45 (m, 4H) 2.30 (t, J=7.5 Hz, 2H), 1.95 (m, 5H). MS (ES+) 602.2.

Deprotection of N-10 Protected Monomers to give (11aS)-7,8-dimethoxy-1,2,3,11a-tetrahydro-5H-pyrrolo[2,1-c][1,4]benzodiazepine-5-one (30)

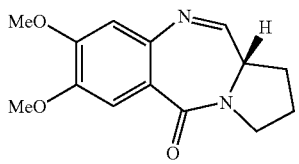

Deprotection of (11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid 4-methoxy-benzyl ester (24)

The N-10 protected PBD (0.08 g, 0.18 mmol) was dissolved in 10% TFA/CH$_2$Cl$_2$ (4 mL) at 0° C. The solution was stirred at 0° C. for 25 min then poured onto ice and neutralised with satd NaHCO$_3$ $_{(aq)}$. The aqueous portion was extracted with CH$_2$Cl$_2$ (3×20 mL) and the combined organic extracts were washed with H$_2$O (50 mL), satd NaCl $_{(aq)}$ (50 mL), dried (MgSO$_4$) and evaporated in vacuo. Purification by flash column chromatography (3% MeOH/97% CHCl$_3$) gave the product 30 as a yellow solid (0.022 g, 47%).

$^1$H NMR (CDCl$_3$) δ 7.61 (d, J=4.3 Hz, 1H), 7.46 (s, 1H), 6.72 (s, 1H), 3.90 (s, 3H), 3.86 (s, 3H), 3.75 (m 2H), 3.65 (m, 1H), 3.5 (m, 1H), 2.30 (m 2H), 1.9 (m, 2H).

Deprotection of (11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid 2-trimethylsilanyl-ethyl ester (25)

A 1.0 M THF solution of tetra-N-butyl-ammonium fluoride (0.295 mL, 0.295 mmol, 1.2 eq.) was added via syringe to a solution of the N-10 protected PBD (0.104 g, 0.25 mmol, 1 eq) in THF (5 mL) at 0° C. The reaction mixture was stirred at room temperature for 4 h. The solvent was removed in vacuo and the product purified by flash column chromatography (4% MeOH/CHCl$_3$) to give the product 30 as a yellow solid (0.052 g, 81%).

Deprotection of (11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid 3-(4-nitro-phenyl)-allyl ester (26)

A solution of the N-10 protected PBD (0.12 g, 0.25 mmol, 1 eq), Pd(PPh$_3$)$_4$ (0.03 g, 0.025 mmol, 0.1 eq), PPh$_3$ (0.006 g, 0.025 mmol, 0.1 eq) and pyrrolidine (0.019 g, 0.023 mL, 2.73 mmol, 1.1 eq) in anhydrous THF (5 mL) was stirred at room temperature for 5 h. The solvent was removed in vacuo and the product purified by flash column chromatography (2% MeOH/98% CHCl$_3$) to give 30 as a yellow oil (0.048 g, 75%).

The N-10 protected PBD (0.05 g, 0.1 mmol, 1 eq) was dissolved in MeOH (5 mL) and 10% Palladium on carbon (0.015 g 30 wt %) and cyclohexadiene (0.016 g, 0.018 mL, 0.2 mmol, 2 eq) were added. The mixture was heated at reflux for 5 h, cooled, filtered through celite and the solvent evaporated in vacuo. Purification by flash column chromatography (3% MeOH/97% CHCl$_3$) gave the product 30 as a yellow solid (0.017 g, 65%).

Deprotection of (11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid 2-benzenesulfonyl-ethyl ester (27)

A 2.0 M MeOH solution of dimethylamine (0.18 mL, 0.37 mmol, 3 eq.) was added via syringe to a solution of the N-10 protected PBD (0.06 g, 0.122 mmol, 1 eq) in MeOH (1 mL). The reaction mixture was stirred at room temperature for 18 h. The solvent was removed in vacuo and the product purified by flash column chromatography (5% MeOH/CHCl$_3$) to give the product 30 as a colourless oil (0.028 g, 87%).

Deprotection of (11S,11aS)-7,8-Dimethoxy-11-hydroxy-5-oxo-1,2,3,10,11,11a-hexahydro-5H-pyrrolo[2,1-c][1,4]benzodiazepine-10-carboxylic acid 4,5-dimethoxy-2-nitro-benzyl ester (28)

A solution of the N-10 protected PBD (0.25 g) in MeOH (10 mL was irradiated at 365 nM. The reaction was monitored by reversed phase HPLC (C18 column, 5 μM particle size, 250 mm×4.6 mm; mobile phase 70% H$_2$O/30% CH$_3$CN/0.1% TFA; detection at 245 nM) against a standard sample of the parent PBD 30. Aliquots of the reaction mixture (20 μL) were injected at 1 h intervals. The conversion to parent PBD was complete in 12 h.

MS (ES+) m/z 261 (M$^+$.)

Deprotection of 2-[4-((11S,11aS)-7,8-Dimethoxy-11-hydroxy-5-oxo-1,2,3,10,11,11a-hexahydro-5H-pyrrolo[2,1-c][1,4]benzodiazepine-10-carbonyloxymethyl)-phenoxycarbonylamino]-pentanedioic acid (46)

An aliquot of a 10 mM stock solution of the carbamate monomer prodrug was diluted to 100 μM in Carboxypeptidase G2 (CPG2) assay buffer (100 mM Tris-HCl, pH 7.3; 260 μM $ZnCl_2$). CPG2 (1 unit) was added and the reaction was incubated at 37° C. The reaction was monitored by reversed phase HPLC (C18 column, 5 μM particle size, 250 mm×4.6 mm; mobile phase 70% $H_2O$/30% $CH_3CN$/0.1% TFA; detection at 245 nM) with 20 μL aliquots being injected at 0, 10, 20, 30, 40, 50 and 60 min. The conversion of the prodrug to the parent imine 30 was complete in 60 minutes.

Deprotection of (11S,11aS)-7,8-Dimethoxy-11-hydroxy-5-oxo-1,2,3,10,11,11a-hexahydro-5H-pyrrolo[1,2-c][1,4]benzodiazepine-10-carboxylic acid allyl ester (94)

A solution of the N-10 protected PBD (0.35 g, 0.96 mmol, 1 eq), $Pd(PPh_3)_4$ (0.055 g, 0.05 mmol, 0.05 eq) and pyrrolidine (0.025 g, 0.1 mL, 1.2 mmol, 1.25 eq) in anhydrous $CH_2Cl_2$ (12 mL) was stirred at room temperature for 3.5 h and the solvent removed in vacuo. The product was purified by flash column chromatography (4% MeOH/96% $CHCl_3$) to give 30 as a yellow oil (0.176 g, 71%).

Synthesis of Dimer Isocyanates

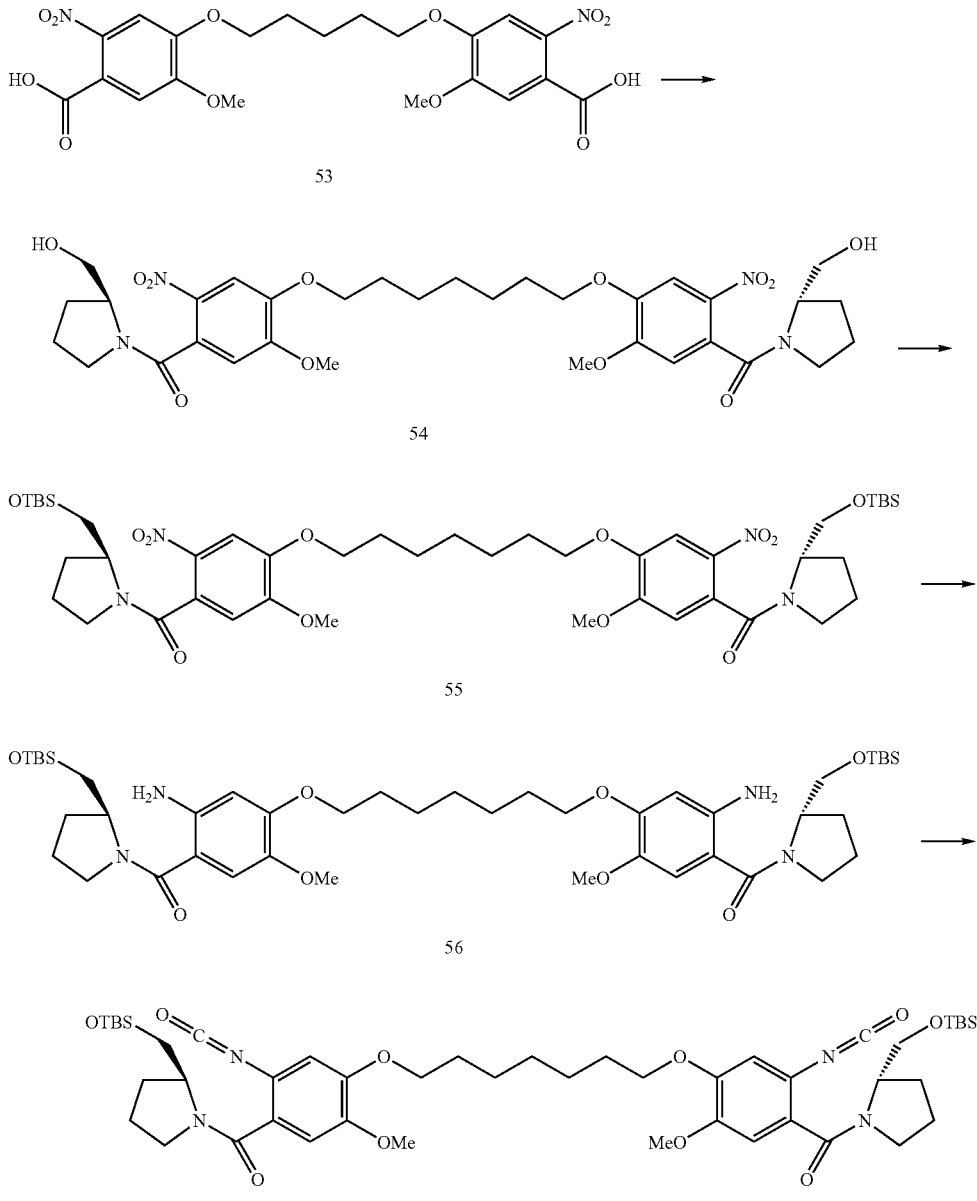

(2S)-1,1'-[[(Pentane-1,5-diyl)dioxy]bis[(2-nitro-5-methoxy-1,4-phenylene)carbonyl]]bis[(2-hydroxymethyl)pyrrolidine] (54)

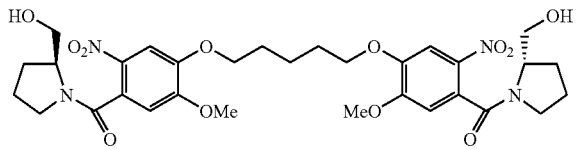

Oxalyl chloride (12.44 g, 8.55 mL, 97.9 mmol, 2.5 eq) and DMF (cat) were added to a solution of dimer core 53 (19.37 g, 39.2 mmol, 1 eq) in anhydrous THF (200 mL) under a $N_2$ atmosphere. The solution was stirred at room temperature for 18 h. The resultant solution was added dropwise to a solution of (S)-(+)-2-pyrrolidine-methanol (9.89 g, 9.65 mL, 97.9 mmol, 2.5 eq) and triethylamine (16.62 g, 22.89 mL, 164 mmol, 4.2 eq) in anhydrous THF (150 mL) at −25° C. (dry ice/ethylene glycol) under a $N_2$ atmosphere. The reaction mixture was allowed to come to room temperature and stirred for 18 h. The solvent was removed in vacuo and the residue dissolved in $CH_2Cl_2$ (750 mL), washed with 1 M HCl (3×200 mL), satd $NaHCO_3\,_{(aq)}$ (3×200 mL), $H_2O$ (2×200 mL), satd $NaCl_{(aq)}$ (250 mL), dried ($MgSO_4$) and evaporated in vacuo. The product was purified by flash column chromatography (5% MeOH/95% EtOAc-10% MeOH/90% EtOAc) to give a yellow foam (11.81 g, 45.6%). $[\alpha]_D^{24.7}$ −94.1° (c=0.260, $CHCl_3$); $^1$H NMR ($CDCl_3$) δ 7.69 (s, 2H), 6.81 (s, 2H), 4.5-4.35 (m, 4H), 4.15 (t, J=6.6 Hz, 4H), 3.98 (s, 6H), 3.9 (m, 2H), 3.8 (m, 2H), 3.18 (t, J=6.9 Hz, 4H), 2.2 (m, 2H), 2.0 (m, 4H), 1.9-1.65 (m, 8H); IR (neat) 3400, 2946, 2873, 1618, 1577, 1522, 1276 cm$^{-1}$; HRMS m/z calcd for $C_{31}H_{41}N_4O_{12}$ 661.2721 (M+H) found 661.2690.

(2S)-1,1'-[[(Pentane-1,5-diyl)dioxy]bis[(2-nitro-5-methoxy-1,4-phenylene) carbonyl]]bis[2-(tert-butyldimethylsilyloxymethyl)pyrrolidine](55)

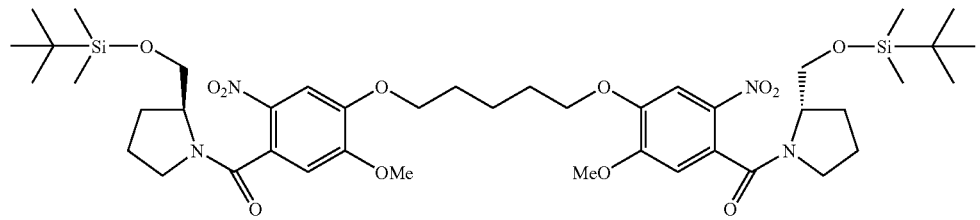

A solution of t-butyldimethylsilyl chloride (6.59 g, 43.56 mmol, 2.6 eq), imidazole (5.7 g, 83.8 mmol, 5 eq) and dimer nitro-alcohol 54 (11.07 g, 16.75 mmol, 1 eq) in anhydrous DMF (30 mL) was stirred at room temperature under a $N_2$ atmosphere for 96 h. The reaction mixture was diluted with $H_2O$ (500 mL) and extracted with EtOAc (4×250 mL). The combined organic extracts were washed with $H_2O$ (2×250 mL), satd $NaCl_{(aq)}$ (250 mL), dried ($MgSO_4$) and evaporated in vacuo. Purification by flash column chromatography (60% EtOAc/40% n-hexane) gave the product as an off white foam (9.02 g, 60.5%). $[\alpha]_D^{24.9}$ −84.9° (c=0.212, $CHCl_3$); $^1$H NMR ($CDCl_3$) δ 7.68 (s, 2H), 6.76 (s, 2H), 4.37 (m, 2H), 4.13 (m, 4H), 3.94 (s, 6H), 4.0-3.85 (m, 4H), 3.12 (m, 4H), 2.15-1.9 (m, 4H), 0.91 (s, 18H), 0.12 (s, 12H); IR (neat) 2952, 2857, 1737, 1643, 1577, 1522 cm$^{-1}$; HRMS m/z calcd for $C_{43}H_{69}N_4O_{12}Si_2$ 889.4451 (M+H) found 889.4473.

(2S)-1,1'-[[(Pentane-1,5-diyl)dioxy]bis[(2-amino-5-methoxy-1,4-phenylene)carbonyl]]bis[2-(tert-butyldimethylsilyloxymethyl)pyrrolidine] (56)

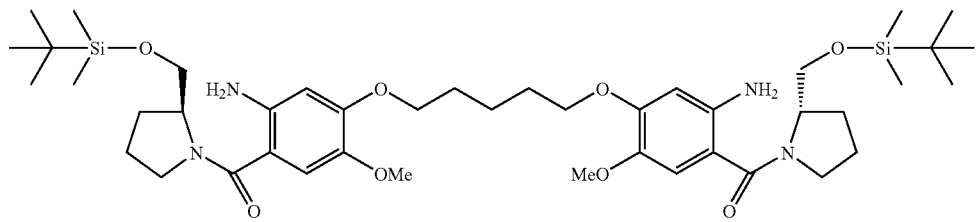

A solution of the dimer nitro compound 55 (9.0 g, 10.12 mmol) in ethanol (100 mL) was hydrogenated (Parr apparatus) over 10% Palladium on carbon (0.9 g, 10 wt %), maintaining the $H_2$ pressure at 16 psi. The reaction was complete when no more $H_2$ was consumed. The mixture was filtered through celite and the ethanol evaporated in vacuo. Purification by flash column chromatography (90% EtOAc/10% n-hexane) gave the product as a yellow foam (6.1 g, 73%). $[\alpha]_D^{25.5}$ −141.2° (c=0.241, $CHCl_3$); $^1$H NMR ($CDCl_3$) δ 6.76 (s, 2H), 6.23 (s, 2H), 4.5-4.3 (m, 4H), 3.99 (t, J=6.6 Hz, 4H) 3.75 (s, 6H), 3.67 (m, 2H), 3.53 (m, 4H), 2.05 (m, 4H), 1.95 (m, 6H), 1.7 (m, 8H), 0.9 (s, 18H), 0.04 (s, 12H); IR (neat) 3449, 3349, 2952, 2857, 1624, 1592, 1514, 1406 cm$^{-1}$; HRMS m/z calcd for $C_{43}H_{73}N_4O_8Si_2$ 829.4967 (M+H) found 829.4998.

(2S)-1,1'-[[(Pentane-1,5-diyl)dioxy]bis[(2-isocy-anato-5-methoxy-1,4-phenylene)carbonyl]]bis[2-(tert-butyldimethylsilyloxymethyl)pyrrolidine](57)

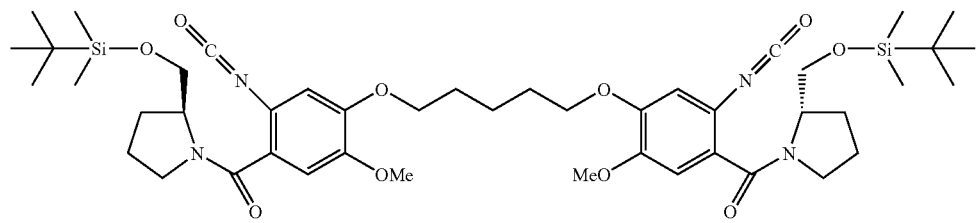

A solution of triethylamine (2.7 eq.) in anhydrous toluene was added to the amine (56)(1 eq.) and triphosgene (0.72 eq.) in anhydrous toluene under a $N_2$ atmosphere. The reaction was finished after 2 hours. (monitored by IR, $v_{NCO}$ 2265 cm$^{1}$). The product was used without further purification.

Synthesis of Dimer Carbamates

General Method

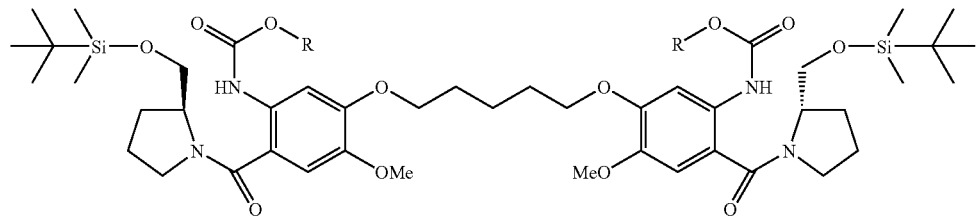

A solution of the appropriate alcohol (2 eq) and triethylamine (2.2 eq) in either anhydrous toluene or anhydrous $CH_2Cl_2$ was added dropwise to a solution of the isocyanate (57)(1 eq) in anhydrous toluene. The reaction was monitored by IR (disappearance of the $v_{NCO}$ 2265 cm$^{-1}$ peak). The reaction mixture was filtered and the filtrate evaporated in vacuo. The product was purified by flash column chromatography.

(2S)-1,1'-[[(Pentane-1,5-diyl)dioxy]bis[(2-allyloxy-carbonylamino-5-methoxy-1,4-phenylene)carbonyl]]bis[2-(tert-butyldimethylsilyloxymethyl)pyrrolidine] (58)

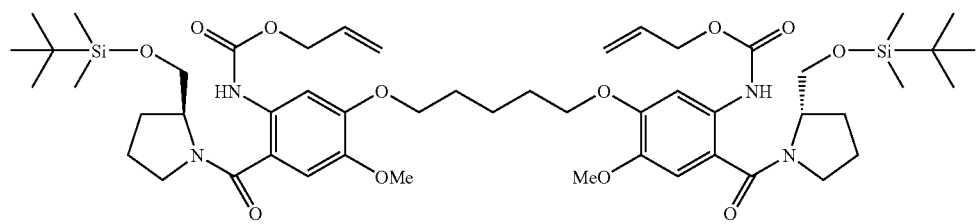

A solution of anhydrous allyl alcohol (0.09 g, 0.105 mL, 1.54 mmol, 2.4 eq) and triethylamine (0.143 g, 0.2 mL, 1.41 mmol) in anhydrous toluene (4 mL) was added to a solution of the isocyanate 57 prepared from the dimer amine 56 (0.533 g, 0.64 mmol), triphosgene (0.14 g, 0.46 mmol) and triethylamine (0.175 g, 0.24 mL, 1.74 mmol) in anhydrous toluene (20 mL). The reaction was complete in 16 h. The product was obtained (flash column chromatography 60% EtOAc/40% n-hexane) as a yellow oil (0.4 g, 62%).

$[\alpha]_D^{26.1}$ −105.7° (c=0.227, CHCl$_3$); $^1$H NMR (CDCl$_3$) δ 9.18 (s, 2H), 7.85 (s, 2H), 6.83 (s, 2H), 6.0 (m, 2H), 5.3 (m, 4H), 4.65 (m, 4H), 4.35 (m, 2H), 4.15 (m, 4H), 4.05 (m, 2H), 3.8 (s, 6H), 3.7 (m, 2H), 3.5 (m, 4H), 2.05 (m, 4H), 1.95 (m, 6H), 1.7 (m, 4H), 0.9 (s, 18H), 0.07 (s, 12H); IR (neat) 3306, 2952, 2930, 2857, 1731, 1621, 1598, 1523, 1406 cm$^{-1}$; HRMS m/z calcd for C$_{51}$H$_{81}$N$_4$O$_{12}$Si$_2$ 997.5390 (M+H) found 997.5336.

(2S)-1,1'-[[(Pentane-1,5-diyl)dioxy]bis[(2-[N-(4-(diprop-2-enyl-L-glutamylcarbonyloxy)benzyloxycarbonyl)]amino-5-methoxy-1,4-phenylene)carbonyl]]bis[2-(tert-butyldimethylsilyloxymethyl)pyrrolidine] (62)

A solution of the carbamate progroup 42 (1.27 g, 3.4 mmol) and triethylamine (0.37 g, 0.515 mL,) in anhydrous CH$_2$Cl$_2$ (25 mL) was added to a solution of the isocyanate 57 prepared from the dimer amine 56 (1.4 g, 1.7 mmol), triphosgene (0.36 g, 0.12 mmol) and triethylamine (0.46 g, 0.64 mL, 4.55 mmol) in anhydrous toluene (75 mL). The reaction was complete in 48 hours. The product was obtained (flash column chromatography 50% EtOAc/50% n-hexane) as a white foam (1.65 g, 60%). $[\alpha]_D^{22.7}$ −39.13° (c=0.23, CHCl$_3$); $^1$H NMR (CDCl$_3$) δ 9.24 (s, 2H), 7.84 (s, 2H), 7.4 (m, 4H), 7.1 (m, 4H), 6.82 (s, 2H), 5.95 (m, 4H), 5.8 (d, J=7.6 Hz, 2H), 5.3 (m, 8H), 5.16 (d, J=12.4 Hz, 2H), 5.1 (d, J=12.3 Hz, 2H), 4.65 (m, 8H), 4.5 (m, 2H), 4.35 (m, 2H), 4.15 (m, 4H), 4.05 (m, 2H), 3.8 (s, 6H), 3.7 (m, 2H), 3.5 (m, 4H), 2.55 (m, 4H), 2.3 (m, 2H), 2.05 (m, 6H), 1.95 (m, 4H), 1.6 (m, 6H), 0.9 (s, 18H), 0.07 (s, 12H); IR (neat) 3338, 2952, 2857, 1738, 1648, 1617, 1597, 1523 cm$^{-1}$.

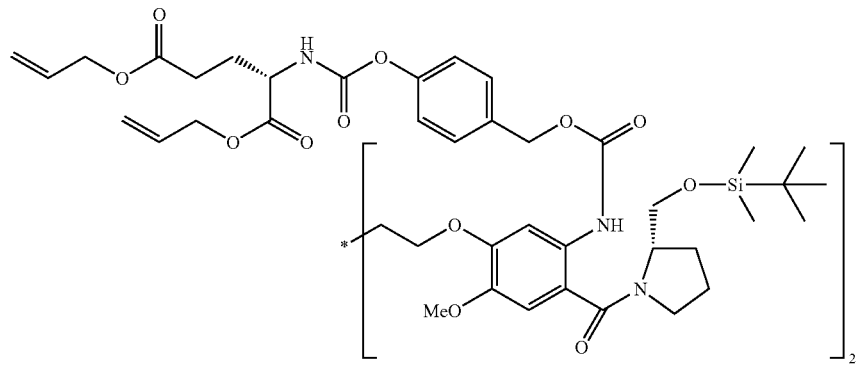

(2S)-1,1'-[[(Pentane-1,5-diyl)dioxy]bis[(2-[N-(4-(diprop-2-enyl-L-glutamylcarbonylamino)benzyloxycarbonyl)]amino-5-methoxy-1,4-phenylene)carbonyl]]bis[2-(tert-butyldimethylsilyloxymethyl)pyrrolidine](63)

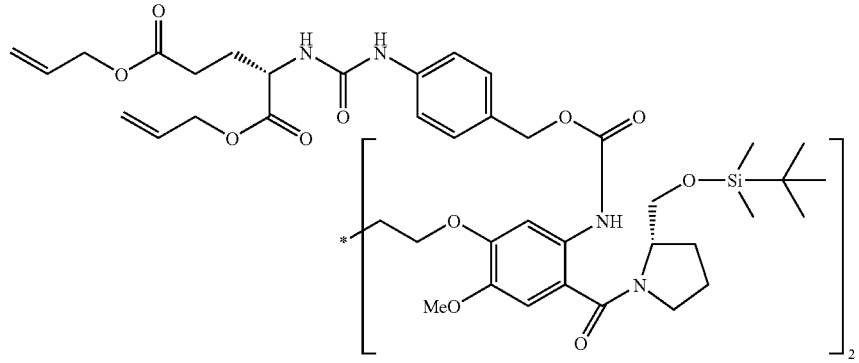

A solution of the urea progroup 35 (1.27 g, 3.4 mmol) and triethylamine (0.37 g, 0.515 mL,) in anhydrous CH$_2$Cl$_2$ (25 mL) was added to a solution of the isocyanate 57 prepared from the dimer amine 56 (1.4 g, 1.7 mmol), triphosgene (0.36 g, 0.12 mmol) and triethylamine (0.46 g, 0.64 mL, 4.55 mmol) in anhydrous toluene (75 mL). The reaction was complete in 48 h. The product was obtained (flash column chromatography 50% EtOAc/50% n-hexane) as a white foam (1.65 g, 60%). $[\alpha]_D^{23.1}$ −50.70 (c=0.217, CHCl$_3$); $^1$H NMR (CDCl$_3$) δ 9.0 (s, 2H), 7.68 (s, 2H), 7.25 (m, 10H), 6.8 (s, 2H), 5.9 (m, 6H), 5.25 (m, 8H), 5.05 (m, 4H), 4.6 (m, 10H), 4.35 (m, 2H), 4.15 (m, 2H), 4.05 (m, 4H), 3.78 (s, 6H), 3.65 (m, 2H), 3.5 (m, 4H), 2.45 (m, 4H), 2.2 (m, 2H), 2.1-1.8 (m, 10H), 1.7 (m, 6H), 0.9 (s, 18H), 0.07 (s, 12H); IR (neat) 3351, 2952, 1736, 1700, 1666, 1601, 1521, 1411, 1200 cm$^{-1}$.

(2S)-1,1'-[[(Pentane-1,5-diyl)dioxy]bis[(2-(2-phenylthioethyloxycarbonyl)-amino-5-methoxy-1,4-phenylene)carbonyl]bis[2-(tert-butyldimethylsilyloxymethyl)pyrrolidine](95)

A solution of 2-(phenylthio)ethanol (0.65 mL, 4.8 mmol,) and triethylamine (0.74 mL, 5.3 mmol) in anhydrous toluene (10 mL) was added to a solution of the isocyanate 57 prepared from the dimer amine 56 (2.0 g, 2.4 mmol), triphosgene (0.515 g, 1.7 mmol) and triethylamine (0.907 mL, 6.5 mmol) in anhydrous toluene (100 mL). The reaction was complete in 90 h. The product was obtained (flash column chromatography 50% EtOAc/50% n-hexane) as a white foam (0.862 g, 30%): $[\alpha]_D^{26}$=−2.6° (c=0.4, CHCl$_3$); $^1$H NMR (CDCl$_3$) δ 9.13 (s, 2H), 7.77 (s, 2H), 7.40-7.32 (m, 4H), 7.30-7.21 (m, 4H), 7.19-7.10 (m, 2H), 6.79 (s, 2H), 4.32-4.17 (m, 6H), 4.15-3.84 (m, 4H), 3.83-3.32 (m, 14H), 3.23-2.99 (m, 4H), 2.13-1.80 (m, 10H), 1.78-1.51 (m, 4H), 0.86 (s, 18H), 0.01 (s, 12H); MS (ES) m/z (relative intensity) 1211 (M$^+$. +Na, 6), 1189 (M$^+$. +1, 100); IR (neat) 2928, 1729, 1597, 1522, 1469, 1406, 1258, 1201 cm$^{-1}$.

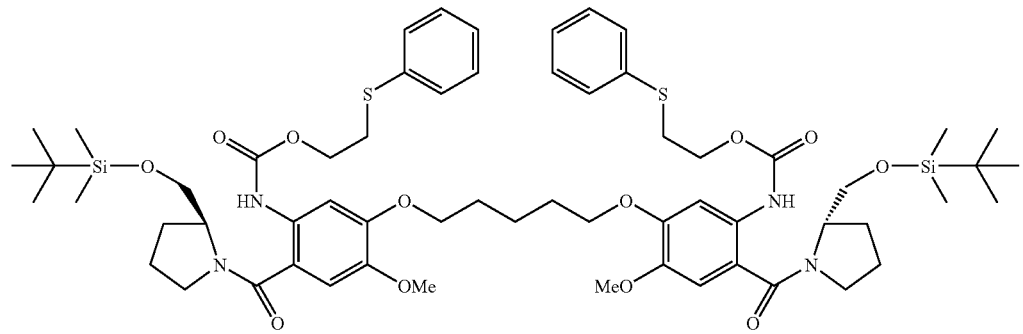

(2S)-1,1'-[[(Pentane-1,5-diyl) dioxy]bis[(2-(2-phenylsulfonylethyloxycarbonyl)-amino-5-methoxy-1,4-phenylene) carbonyl]bis[2-(tert-butyldimethylsilyloxymethyl)pyrrolidine](96)

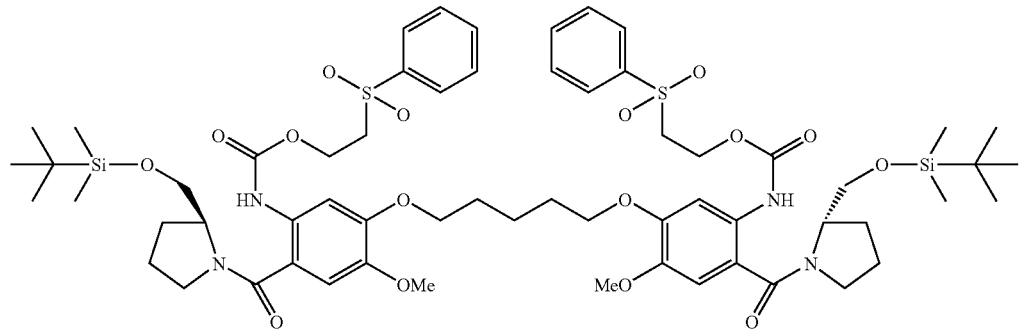

A solution of 2-(phenylsulfonyl)ethanol (0.58 mL, 4.8 mmol,) and triethylamine (0.74 mL, 5.3 mmol) in anhydrous toluene (20 mL) was added to a solution of the isocyanate 57 prepared from the dimer amine 56 (2.0 g, 2.4 mmol), triphosgene (0.515 g, 1.7 mmol) and triethylamine (0.907 mL, 6.5 mmol) in anhydrous toluene (100 mL). The reaction was complete in 90 h. The product was obtained (flash column chromatography 50% EtOAc/50% n-hexane) as a white foam (2.17 g, 77%): $[\alpha]_D^{22}=-87.5°$ (c=1.0, CHCl$_3$); $^1$H NMR (CDCl$_3$) δ 9.04 (s, 2H), 8.07-7.93 (m, 3H), 7.77-7.48 (m, 7H), 7.26 (s, 2H), 6.82 (s, 2H), 4.46-4.26 (m, 5H), 4.18-3.89 (m, 6H), 3.88-3.64 (m, 8H), 3.63-3.42 (m, 8H), 2.16-1.84 (m, 10H), 1.83-1.51 (m, 5H), 0.90 (s, 18H), 0.04 (s, 12H); MS (ES) m/z (relative intensity) 1256 (M$^+$. +1, 100); IR (neat) 3299, 2952, 1735, 1602, 1528, 1326, 1025, 841 cm$^{-1}$.

Deprotection of Alcohols

General Methods for the Deprotection of Dimer Tert-Butyldimethylsilyl Ethers

Method A

A 1.0 M THF solution of tetra-N-butyl-ammonium fluoride (2.4 eq.) was added via syringe to a solution of the TBDMS ether (1 eq.) in THF at 0° C. The reaction was stirred at room temperature until reaction was complete (TLC). The solvent was removed in vacuo and the product purified by flash column chromatography.

Method B

A solution of the TBDMS ether in a mixture of AcOH/THF/H$_2$O (3/1/1) was stirred at room temperature until reaction was complete (TLC). The reaction mixture was cooled (ice bath) and carefully neutralised with NaHCO$_3$ $_{(aq)}$ (1 eq). The mixture was extracted with EtOAc (x3) the combined extracts were washed with water (x1), satd NaCl $_{(aq)}$ (x1), dried (MgSO$_4$) and evaporated in vacuo. The product was purified by flash column chromatography.

(2S)-1,1'-[[(Pentane-1,5-diyl)dioxy]bis[(2-allyloxy-carbonylamino-5-methoxy-1,4-phenylene)carbonyl]]bis[2-(hydroxymethyl)pyrrolidine] (59)

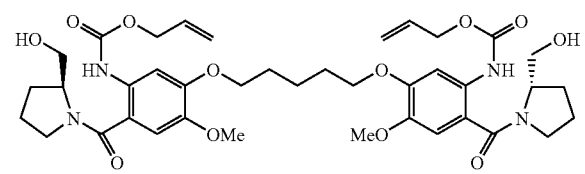

The TBDMS ether 58 (0.32 g, 0.32 mmol) in THF (20 mL) was deprotected (Method A: Bu$_4$NF (0.765 mL, 0.765 mmol)) to give the product (flash column chromatography 5% MeOH/95% EtOAc) as a white foam (0.23 g, 93%). $[\alpha]_D^{24.7}$–93.50 (c=0.214, CHCl$_3$); $^1$H NMR (CDCl$_3$) δ 8.8 (s, 2H), 7.8 (s, 2H), 6.82 (s, 2H), 6.0 (m, 2H), 5.3 (m, 4H), 4.67 (m, 4H), 4.4 (m, 2H), 4.1 (t, J=6.6 Hz, 4H), 3.85 (m, 2H), 3.8 (s, 6H), 3.75 (m, 2H), 3.6 (m, 2H), 3.5 (m, 2H), 2.17 (m, 2H), 1.95 (m, 6H), 1.7 (m, 8H); IR (neat) 3338, 2951, 2873, 1731, 1597, 1524, 1408 cm$^{-1}$; HRMS m/z calcd for C$_{39}$H$_{52}$N$_4$O$_{12}$Na 791.3479 (M+Na) found 791.3499.

(2S)-1,1'-[[(Pentane-1,5-diyl)dioxy]bis[(2-[N-(4-(diprop-2-enyl-L-glutamylcarbonyloxy)benzyloxycarbonyl)]amino-5-methoxy-1,4-phenylene)carbonyl]]bis[(2-hydroxymethyl)pyrrolidine] (64)

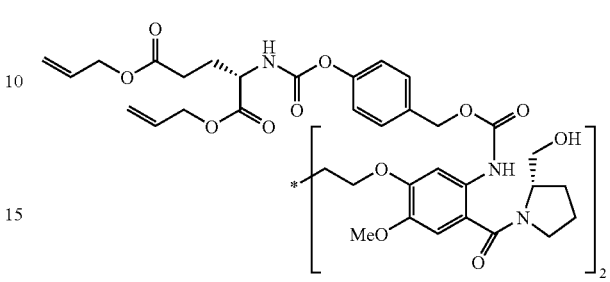

The TBDMS ether 62 (1.63 g, 0.99 mmol) was deprotected (Method B: AcOH (18 mL)/THF (6 mL)/H$_2$O (6 mL) then NaHCO$_3$ (26.31 g, 313.2 mmol) in H$_2$O (300 mL)) to give the product (flash column chromatography 2% MeOH/98% EtOAc) as a colourless oil (1.0 g, 72%). $[\alpha]_D^{22.7}$–34.01° (c=0.147, CHCl$_3$); $^1$H NMR (CDCl$_3$) δ 8.8 (s, 2H), 7.7 (s, 2H), 7.4 (m, 4H), 7.1 (m, 4H), 6.78 (s, 2H), 5.95 (m, 4H), 5.8 (m, 2H), 5.3 (m, 8H), 5.17 (d, J=12.4 Hz, 2H), 5.10 (d, J=12.3 Hz, 2H), 4.65 (m, 8H), 4.5 (m, 2H), 4.36 (m, 4H), 4.12 (m, 4H), 3.82 (m, 2H), 3.8 (s, 6H), 3.7 (m, 2H), 3.55 (m, 2H), 3.43 (m, 2H), 2.51 (m, 4H), 2.3 (m, 2H), 2.1 (m, 4H), 1.95 (m, 4H), 1.85 (m, 2H), 1.68 (m, 6H); IR (neat) 3326, 2946, 1731, 1597, 1524, 1203 cm$^{-1}$.

(2S)-1,1'-[[(Pentane-1,5-diyl)dioxy]bis[(2-[N-(4-(diprop-2-enyl-L-glutamylcarbonylamino)benzyloxycarbonyl)]amino-5-methoxy-1,4-phenylene)carbonyl]]bis[(2-hydroxymethyl)pyrrolidine] (65)

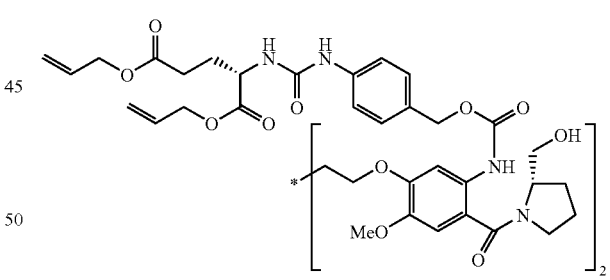

The TBDMS ether 63 (1.075 g, 0.66 mmol) was deprotected (Method B: AcOH (12 mL)/THF (4 mL)/H$_2$O (4 mL) then NaHCO$_3$ (17.54 g, 209.0 mmol) in H$_2$O (250 mL)) to give the product (flash column chromatography 3% MeOH/97% EtOAc) as a white foam (0.69 g, 75%). $[\alpha]_D^{21.6}$–46.98° (c=0.3299, CHCl$_3$); $^1$H NMR (CDCl$_3$) δ 8.6 (s, 2H), 7.72 (m, 4H), 7.21 (m, 8H), 6.79 (s, 2H), 6.02 (d, J=7.8 Hz, 2H), 5.86 (m, 4H), 5.3 (m, 8H), 5.04 (s, 4H), 4.6 (m, 8H), 4.49 (m, 2H), 4.39 (m, 2H), 4.01 (m, 4H), 3.83 (m, 2H), 3.78 (s, 6H), 3.69 (m, 2H), 3.5 (m, 4H), 2.45 (m, 4H), 2.2 (m, 2H), 2.1 (m, 2H), 2.0-1.8 (m, 10H), 1.7 (m, 4H), 1.55 (m, 2H); IR (neat) 3351, 2946, 2877, 1732, 1601, 1520, 1202 cm$^{-1}$.

(2S)-1,1'-[[(Pentane-1,5-diyl)dioxy]bis[(2-(2-phenylthioethyloxycarbonyl)-amino-5-methoxy-1,4-phenylene)carbonyl]bis[2-hydroxymethylpyrrolidine] (97)

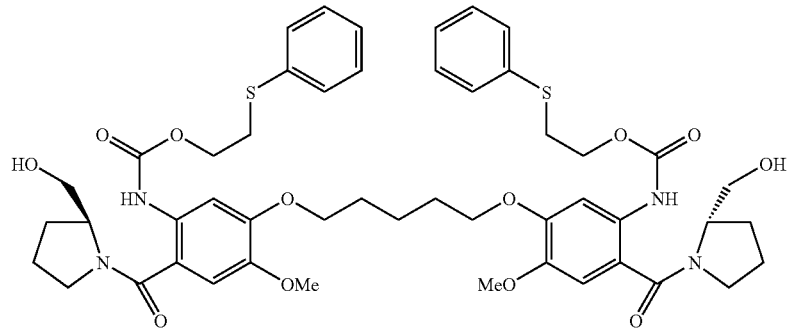

The TBDMS ether 95 (0.862 g, 0.7 mmol) was deprotected (Method B: AcOH (6 mL)/THF (2 mL)/H$_2$O (2 mL) then NaHCO$_3$ (8.8 g, 104.8 mmol) in H$_2$O (400 mL)) to give the product (flash column chromatography EtOAc) as a pale yellow foam (0.486 g, 70%): [α]$_D^{26}$ −64.0° (c=1.0, CHCl$_3$); $^1$H NMR (CDCl$_3$) δ 8.73 (s, 2H), 7.70 (s, 2H), 7.46-7.36 (m, 4H), 7.35-7.14 (m, 6H), 6.80 (s, 2H), 4.49-4.34 (bs, 2H), 4.34-4.20 (m, 6H), 4.09 (t, J=7.0 Hz, 4H), 3.93-3.78 (m, 9H), 3.77-3.65 (m, 3H), 3.64-3.41 (m, 5H), 3.19 (t, J=7.0 Hz, 4H), 2.24-2.10 (m, 2H), 2.01-1.83 (m, 7H), 1.81-1.56 (m, 9H); MS (ES) m/z (relative intensity) 983 (M++Na, 12), 961 (M$^+$. +1, 100); IR (neat) 3331, 2943, 1718, 1654, 1560, 1508, 1458 cm$^{-1}$.

(2S)-1,1'-[[(Pentane-1,5-diyl)dioxy]bis[(2-(2-phenylsulfonylethyloxycarbonyl)-amino-5-methoxy-1,4-phenylene)carbonyl]bis[2-hydroxymethylpyrrolidine] (98)

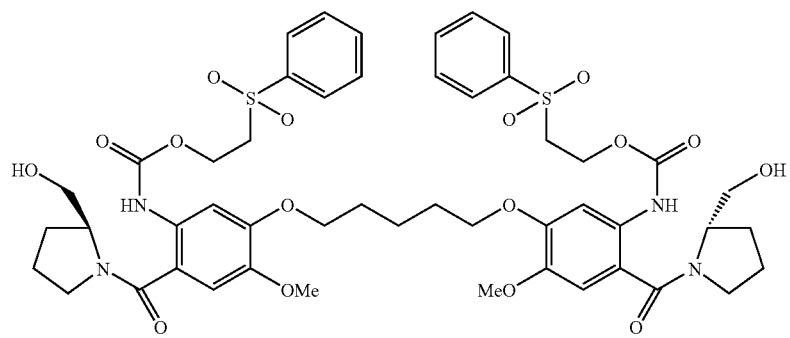

The TBDMS ether 96 (2.14 g, 1.7 mmol) was deprotected (Method B: AcOH (6 mL)/THF (2 mL)/H$_2$O (2 mL) then NaHCO$_3$ (8.8 g, 104.8 mmol) in H$_2$O (600 mL)) to give the product (flash column chromatography 2% MeOH/98% EtOAc) as a white foam (1.39 g, 80%): [α]$_D^{25}$ −66.5° (c=1.0, CHCl$_3$); $^1$H NMR (CDCl$_3$) δ 8.65 (s, 2H), 7.95-7.89 (m, 3H), 7.71-7.53 (m, 9H), 6.81 (s, 2H), 4.53-4.19 (m, 9H), 4.02-3.88 (m, 2H), 3.81 (s, 6H), 3.74-3.62 (m, 2H), 3.60-3.40 (m, 9H), 2.25-2.10 (m, 2H), 2.00-1.59 (m, 15H); MS (ES) m/z (relative intensity) 1025 (M$^+$., 50); IR (neat) 3329, 2929, 1727, 1595, 1520, 1144 cm$^{-1}$.

Cyclisation of Dimer Alcohols

General Methods

Method A

The alcohol (1 eq), (diacetoxyiodo)benzene (2.3 eq) and TEMPO (0.23 eq) were dissolved in CH$_2$Cl$_2$ and the mixture stirred at room temperature until reaction was complete (TLC). The reaction mixture was washed with satd NaHSO$_3$ $_{(aq)}$ (x1) and the NaHSO$_3$ portion was then washed with CH$_2$Cl$_2$ (x4). The combined organic extracts were washed with satd NaHCO$_3$ $_{(aq)}$ (x2), satd NaCl $_{(aq)}$ (x1), dried (MgSO$_4$) and evaporated in vacuo. The product was purified by either flash column chromatography or recrystallisation.

Method B

The alcohol (1 eq), pyridinium dichromate (2.4 eq) and 4 Å molecular sieves (0.1 g/mmol alcohol) in anhydrous CH$_2$Cl$_2$ were stirred at room temperature under a N$_2$ atmosphere until reaction was complete (TLC). The reaction mixture was filtered through celite, washing with EtOAc. The solvent was evaporated in vacuo and the product purified by flash column chromatography.

1,1'-[[Pentane-1,5-diyl]dioxy]bis[(11S,11aS)-10-(allyloxycarbonyl)-11-hydroxy-7-methoxy-1,2,3,10,11,11a-hexahydro-5H-pyrrolo[2,1-c][1,4]benzodiazepine-5-one] (60)

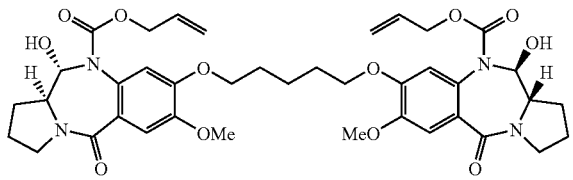

The alcohol 59 (0.227 g, 0.295 mmol) was reacted (Method B) with pyridinium dichromate (0.27 g, 0.71 mmol) and 4 Å molecular sieves (0.295 g) in anhydrous $CH_2Cl_2$ (5 mL). The product was obtained (flash column chromatography 5% MeOH/95% EtOAc) as a white foam (0.073 g, 32%).

$^1$H NMR (CDCl$_3$) δ 7.24 (s, 2H), 6.65 (s, 2H), 5.8 (m, 2H), 5.63 (d, J=8.7 Hz, 2H), 5.12 (m, 4H), 4.66 (m, 2H), 4.44 (m, 2H), 4.17 (m, 2H), 4.01 (m, 4H), 3.9 (m, 8H), 3.69 (m, 2H), 3.50 (m, 4H), 2.12 (m, 4H), 2.02 (m, 4H), 1.91 (m, 4H), 1.64 (m, 2H); HRMS m/z calcd for $C_{39}H_{48}N_4O_{12}Na$ 787.3166 (M+Na) found 787.3173.

1,1'-[[Pentane-1,5-diyl]dioxy]bis[(11S,11aS)-10-[N-(4-(diprop-2-enyl-L-glutamylcarbonyloxy)benzyloxycarbonyl)]-11-hydroxy-7-methoxy-1,2,3,10,11,11a-hexahydro-5H-pyrrolo[2,1-c][1,4]benzodiazepine-5-one] (66)

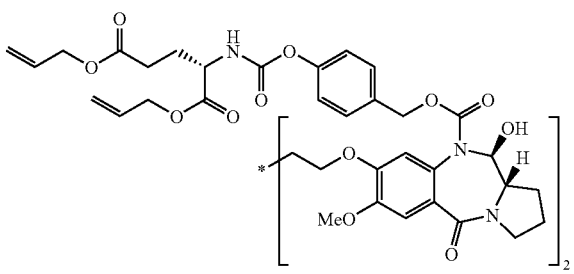

The alcohol 64 (1.0 g, 0.71 mmol) was reacted (Method A) with DAIB (0.53 g, 1.64 mmol) and TEMPO (0.025 g, 0.164 mmol) in $CH_2Cl_2$ (10 mL). The product was obtained (flash column chromatography 5% MeOH/95% EtOAc) as a white foam (0.72 g, 72%). $[α]_D^{22.6}$+128.03° (c=0.289, CHCl$_3$); $^1$H NMR (CDCl$_3$) δ 7.23 (s, 2H), 7.16 (d, J=6.9 Hz, 4H), 7.01 (d, J=6.8 Hz, 4H), 6.55 (s, 2H), 6.01 (s, 2H), 5.89 (m, 4H), 5.63 (m, 2H), 5.3 (m, 10H), 4.83 (d, J=11.9 Hz, 2H), 4.65 (m, 8H), 4.44 (m, 2H), 4.09 (m, 2H), 3.88 (m, 8H), 3.75 (m, 4H), 3.49 (m, 4H), 2.48 (m, 4H), 2.27 (m, 2H), 2.15-1.95 (m, 10H), 1.89 (m, 4H), 1.52 (m, 2H).

$[α]_D^{22.6}$+128.03° (c=0.289, CHCl$_3$); $^1$H NMR (CDCl$_3$) δ 7.23 (s, 2H), 7.16 (d, J=6.9 Hz, 4H), 7.01 (d, J=6.8 Hz, 4H), 6.55 (s, 2H), 6.01 (s, 2H), 5.89 (m, 4H), 5.63 (m, 2H), 5.3 (m, 10H), 4.83 (d, J=11.9 Hz, 2H), 4.65 (m, 8H), 4.44 (m, 2H), 4.09 (m, 2H), 3.88 (m, 8H), 3.75 (m, 4H), 3.49 (m, 4H), 2.48 (m, 4H), 2.27 (m, 2H), 2.15-1.95 (m, 10H), 1.89 (m, 4H), 1.52 (m, 2H).

1,1'-[[Pentane-1,5-diyl]dioxy]bis[(11S,11aS)-10-[N-(4-(diprop-2-enyl-L-glutamylcarbonylamino)benzyloxycarbonyl)]-11-hydroxy-7-methoxy-1,2,3,10,11,11a-hexahydro-5H-pyrrolo[2,1-c][1,4]benzodiazepine-5-one] (67)

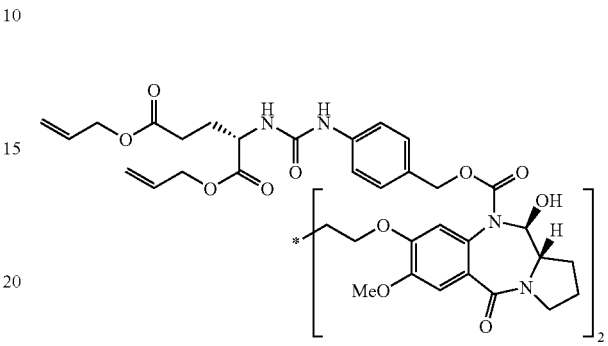

The alcohol 65 (0.51 g, 0.36 mmol) was reacted (Method A) with DAIB (0.27 g, 0.83 mmol) and TEMPO (0.012 g, 0.083 mmol) in $CH_2Cl_2$ (8 mL). The product was obtained (flash column chromatography 5% MeOH/95% EtOAc) as a white foam (0.325 g, 64%). $[α]_D^{21.1}$+192.0° (c=0.216, CHCl$_3$); $^1$H NMR (CDCl$_3$) δ 8.03 (s, 2H), 7.33 (m, 4H), 7.26 (s, 2H), 7.15 (d, J=7.6 Hz, 4H), 6.35 (s, 2H), 5.85 (m, 8H), 5.64 (dd, J=4 Hz, 9.9 Hz, 2H), 5.25 (m, 10H), 4.6 (m, 12H), 4.02 (m, 2H), 3.87 (m, 8H), 3.8 (m, 2H), 3.72 (m, 2H), 3.57 (m, 4H), 2.69 (m, 2H), 2.36 (m, 4H), 2.2-1.95 (m, 10H), 1.68 (m, 2H), 1.5-1.2 (m, 4H); IR (neat) 3359, 2949, 1737, 1707, 1603, 1547, 1515 cm$^{-1}$.

1,1'-[[Pentane-1,5-diyl]dioxy]bis[(11S,11aS)-10-[N-(2-phenylthioethyloxycarbonyl)]-11-hydroxy-7-methoxy-1,2,3,10,11,11a-hexahydro-5H-pyrrolo[2,1-c][1,4]benzodiazepine-5-one] (99)

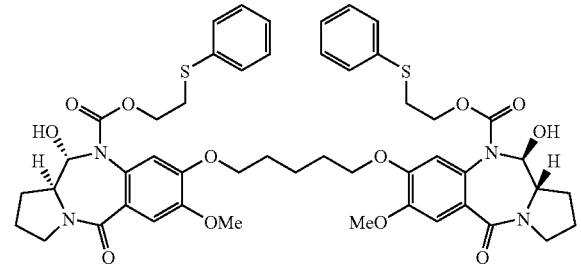

Dess-Martin periodinane (0.15% v/v soln. in DCM, 1.55 mL, 0.55 mmol) was added to a solution of the dimer alcohol 97 (0.243 g, 0.25 mmol) in anhydrous DCM (10 mL). The reaction was monitored by HPLC and was complete in 1.5 h. The reaction mixture was washed with satd NaHCO$_3$ (3×50 mL), H$_2$O (3×50 mL), brine (3×50 mL), dried (MgSO$_4$) and the solvent evaporated in vacuo. Flash column chromatography (2% MeOH/98% CHCl$_3$) gave the product as a white foam (0.114 g, 50%): $[α]_D^{26}$=+97.5° (c=0.2, CHCl$_3$); $^1$H NMR (CDCl$_3$) δ 7.40-7.15 (m, 12H), 6.74 (s, 2H), 5.68-5.60 (m, 2H), 4.45-4.24 (m, 6H), 4.05-3.78 (m, 8H), 3.76-3.38 (m, 6H), 3.12-3.07 (m, 2H), 2.97-2.87 (m, 2H), 2.31-1.66 (m, 12H), 1.57-1.55 (m, 2H); MS (ES) m/z (relative intensity) 979 (M⁺. +Na, 100), 957 (M⁺. +1, 35); IR (neat) 3298, 2945, 1704, 1602, 1514, 1432, 1270 cm⁻¹.

1,1'-[[Pentane-1,5-diyl]dioxy]bis[(11S,11aS)-10-[N-(2-phenylsulfonylethyloxycarbonyl)]-11-hydroxy-7-methoxy-1,2,3,10,11,11a-hexahydro-5H-pyrrolo[2,1-c][1,4]benzodiazepine-5-one] (100)

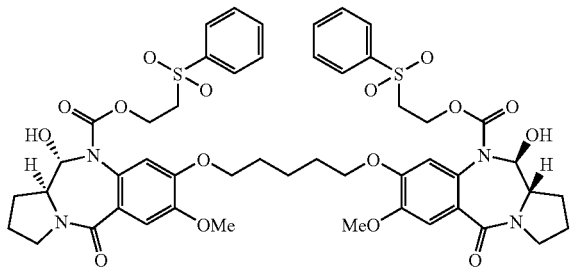

The alcohol 98 (0.80 g, 0.78 mmol) was reacted (Method A) with DAIB (0.553 g, 1.72 mmol) and TEMPO (0.024 g, 0.16 mmol) in CH₂Cl₂ (5 mL). The product was obtained (flash column chromatography 2% MeOH/98% CHCl₃) as a white foam (0.641 g, 80%).

$[\alpha]_D^{26}$ +73.0° (c=1.0, CHCl₃); ¹H NMR (CDCl₃) δ 8.12-7.40 (m, 10H), 7.20 (s, 2H), 6.97-6.75 (m, 2H), 5.70-5.55 (m, 2H), 4.86 (bs, 2H), 4.81 (bs, 1H), 4.43 (bs, 1H), 4.22-3.97 (m, 6H), 3.88 (s, 6H), 3.75-3.16 (m, 11H), 2.21-1.82 (m, 12H), 1.72-1.54 (m, 2H); MS (ES) m/z (relative intensity) 1044 (M⁺. Na, 60), 1043 (100), 1021 (M⁺., 23); IR (neat) 3345, 2953, 1748, 1628, 1319 cm⁻¹.

Deprotection of Groups in Compounds 66 and 67

1,1'-[[Pentane-1,5-diyl]dioxy]bis[(11S,11aS)-10-[N-(4-(L-glutamylcarbonyloxy)benzyloxycarbonyl)]-11-hydroxy-7-methoxy-1,2,3,10,11,11a-hexahydro-5H-pyrrolo[2,1-c][1,4]benzodiazepine-5-one] (68)

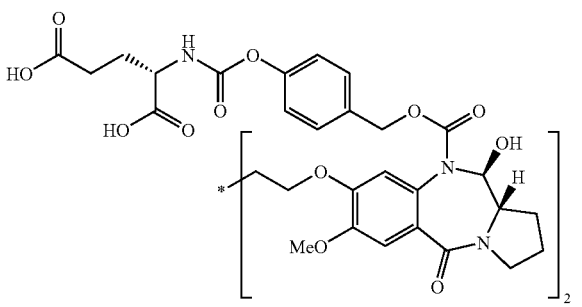

A solution of the bis-diallyl ester 66 (0.69 g, 0.49 mmol, 1 eq), Pd(PPh₃)₄ (0.08 g, 0.069 mmol, 0.14 eq) and morpholine (0.33 g, 0.33 mL, 3.8 mmol, 7.7 eq) in anhydrous CH₂Cl₂ (12 mL) was stirred at room temperature for 18 h. The solvent was decanted and the solid residue was washed with EtOAc (2×15 mL), CH₂Cl₂ (2×15 mL), dissolved in MeOH (5 mL) and passed down an IRC 50, weakly acidic, ion exchange column, eluting with MeOH (100 mL). The solvent was removed in vacuo to give the product as a white foam (0.48 g, 78%).

$[\alpha]_D^{16.2}$ +98.90 (c=0.273, MeOH); ¹H NMR (CD₃OD) δ 7.21 (m, 4H), 7.07 (m, 6H), 6.72 (s, 2H), 5.66 (d, J=9 Hz, 2H), 5,24 (d, J=12.2 Hz, 2H), 4.22 (m, 2H), 3.93 (m, 6H), 3.84 (m, 8H), 3.62 (m, 4H), 3.45 (m, 4H), 2.43 (m, 4H), 2.21 (m, 2H), 2.15-1.95 (m, 10H), 1.8 (m, 4H), 1.6 (m, 2H).

1,1'-[[Pentane-1,5-diyl]dioxy]bis[(11S,11aS)-10-[N-(4-(diprop-2-enyl-L-glutamylcarbonylamino)benzyloxycarbonyl)]-11-hydroxy-7-methoxy-1,2,3,10,11,11a-hexahydro-5H-pyrrolo[2,1-c][1,4]benzodiazepine-5-one] (69)

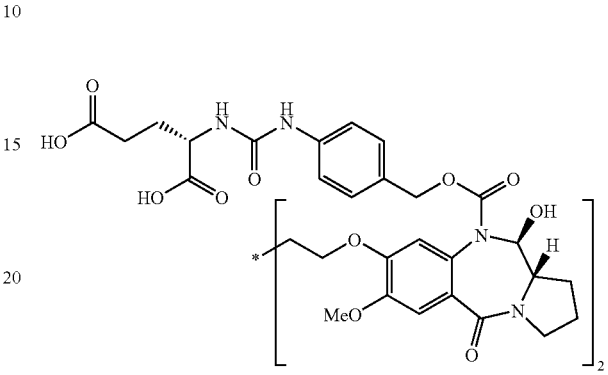

A solution of the bis-diallyl ester 67 (0.29 g, 0.21 mmol, 1 eq), Pd(PPh₃)₄ (0.033 g, 0.028 mmol, 0.14 eq) and morpholine (0.14 g, 0.14 mL, 1.6 mmol, 7.7 eq) in anhydrous CH₂Cl₂ (5 mL) was stirred at room temperature for 18 h. The solvent was decanted and the solid residue was washed with EtOAc (2×15 mL), CH₂Cl₂ (2×15 mL), dissolved in MeOH (5 mL) and passed down an IRC 50, weakly acidic, ion exchange column, eluting with MeOH (100 mL). The solvent was removed in vacuo to give the product as an off-white solid (0.2 g 77%). $[\alpha]_D^{15.6}$ +143.2° (c=0.234, MeOH); ¹H NMR (CD₃OD) δ7.33 (d, J=6.4 Hz, 6H), 7.15 (m, 6H), 6.66 (s, 2H), 5.65 (d, J=9.4 Hz, 2H), 5.26 (d, J=11.44 Hz, 2H), 4.76 (d, J=11.8 Hz, 2H), 4.36 (m, 2H), 4.15-3.8 (m, 12H), 3.65 (m, 4H), 2.39 (m, 4H), 2.25-1.9 (m, 12H), 1.8 (m, 4H), 1.55 (m, 2H).

Deprotection of N-10 protected dimers to give 1,1-[(pentane-1,5-diyl)dioxy]bis[(11aS)-7-methoxy-1,2,3,11a-tetrahydro-5H-pyrrolo[2,1-c][1,4]benzodiazepine-5-one] (61)

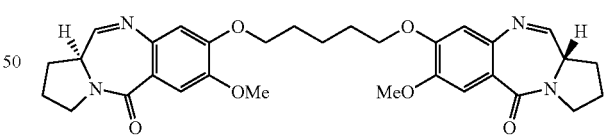

Deprotection of 1,1'-[[Pentane-1,5-diyl]dioxy]bis [(11S,11aS)-10-(allyloxycarbonyl)-11-hydroxy-7-methoxy-1,2,3,10,11,11a-hexahydro-5H-pyrrolo[2,1-c][1,4]benzodiazepine-5-one] (60)

A solution of the alloc protected dimer (0.068 g, 0.09 mmol, 1 eq), Pd(PPh₃)₄ (0.005 g, 0.08 mmol, 0.2 eq) and pyrrolidine (0.016 g, 0.018 mL, 0.22 mmol, 2.5 eq) in anhydrous CH₂Cl₂ (5 mL) was stirred at room temperature for 4 h and the solvent removed in vacuo. The product was purified by flash column chromatography (5% MeOH/95% CHCl₃) to give 61 as a yellow solid (0.04 g, 82%). ¹H NMR (CDCl₃) δ

7.61 (d, J=4.4 Hz, 2H), 7.44 (s, 2H), 6.73 (s, 2H), 4.04 (m, 4H), 3.87 (s, 6H), 3.8 (m, 2H), 3.69 (m, 2H), 3.5 (m, 2H), 2.24 (m, 4H), 2.05-1.85 (m, 8H), 1.6 (m, 2H).

Deprotection of 1,1'-[[Pentane-1,5-diyl]dioxy]bis [(11S,11aS)-10-[N-(4-(L-glutamylcarbonyloxy)benzyloxycarbonyl)]-11-hydroxy-7-methoxy-1,2,3,10, 11,11a-hexahydro-5H-pyrrolo[2,1-c][1,4] benzodiazepine-5-one] (68)

An aliquot of a 10 mM stock solution of the carbamate dimer prodrug was diluted to 100 µM in Carboxypeptidase G2 (CPG2) assay buffer (100 mM Tris-HCl, pH 7.3; 260 µM ZnCl$_2$). CPG2 (1 unit) was added and the reaction was incubated at 37° C. The reaction was monitored by reversed phase HPLC (C18 column, 5 µM particle size, 250 mm×4.6 mm; mobile phase 70% H$_2$O/30% CH$_3$CN/0.1% TFA; detection at 245 nM) with 20 µL aliquots being injected at 0, 15, 30, 45, 60 and 75 min. The conversion of the prodrug to the parent imine 61 was complete in 75 min.

Synthesis of Alternate Monomer Isocyanate

Methyl-2-isocyanotobenzoate (71)

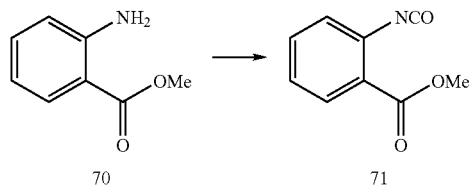

70           71

Triphosgene (5.8 g, 19.8 mmol) was added to a solution of methyl anthranilate (70) (1 g, 6.6 mmol) and pyridine (8.0 mL, 99 mmol) in CH$_2$Cl$_2$ and stirred at room temperature for 4 hours. The reaction mixture was washed in 1N HCl (3×50 mL), H$_2$O (3×50 mL), brine (3×50 mL) and dried over MgSO$_4$. Excess solvent was removed in vacuo to give a quantitative yield of pure material (71). $^1$H NMR (250 MHz, CDCl$_3$) δ 8.02 (dd, 1H, J=1.7, 7.9 Hz, aromatic H), 7.46 (dt, 1H, J=1.5, 5.8, 7.7 Hz, aromatic H), 7.29-7.25 (m, 1H, H-3), 7.12 (dd, 1H, J=1.2, 8.03 Hz, H-2), 3.96 (s, 3H, OMe); IR (neat) ν 3676, 3483, 3369, 2956, 2844, 2592, 2306, 2191, 2129, 1944, 1735, 1697, 1611, 1540, 1457, 1320, 1280, 1170, 1097, 1045, 968, 879, 831, 768, 704 cm$^{-1}$; MS m/z 178 9 (M$^+$. +1), 153, 152, 146, 121, 120, 92, 90.

Synthesis of Alternate Monomer Carbamate

Methyl-2-((E)-3-phenyl-allyloxycarbonylamino)-benzoate (72)

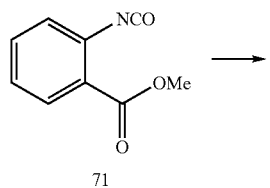

71

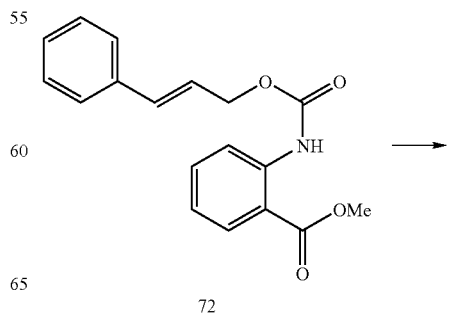

72

A solution of methyl-2-isocyanatobenzoate (71)(1 g, 5.6 mmol) in CH$_2$Cl$_2$ (100 mL) was cooled to 0° C. and treated with pyridine (7 mL, 84 mmol). Cinnamyl alcohol (2.25 g, 1.68 mmol) in CH$_2$Cl$_2$ (150 mL) was added dropwise to the stirring solution over a period of 1 hour and the reaction mixture was allowed to stir for 12 hours, under nitrogen. The reaction mixture was washed in brine (100 mL). The aqueous phase was washed with CH$_2$Cl$_2$ (3×100 mL). The organic phases were combined and washed with 1N HCl (200 mL) and dried over MgSO$_4$. Purification was achieved through flash column chromatography (80% Pet ether:EtOAc) to furnish the carbamate (72) as a colourless solid (85%). $^1$H NMR (250 MHz, CDCl$_3$) δ 10.9 (br, s, 1H, NH), 8.45 (dd. 1H, J=1.0, 8.5 Hz, aromatic H), 8.01 (dd, 1H, J=1.66, 8.0 Hz, aromatic H), 7.54 (ddd, 1H, J=1.67, 7.3, 8.5 Hz, aromatic H), 7.5-7.2 (m, 5H, coc aromatic H), 7.03 (ddd, 1H, J=1.2, 8.0 Hz, aromatic H), 6.71 (d, 1H, J=16 Hz, 3'-H), 6.35 (dt, 1H, J=6.3, 16 Hz, 2'-H), 4.48 (dd, 2H, J=1.3, 6.3, 1'-H), 3.91 (s, 1H); $^{13}$C NMR (62.9 MHz, CDCl$_3$) δ 169.0 (ester carbonyl), 153.5 (CO-carbamate), 141.9 (aromatic quat), 136.8 (aromatic quat), 135.0 (methine), 131.3 (methine), 129.0 (methine), 128.4 (methine), 127.1 (methine), 123.9 (alkenic methine), 122.0 (methine), 119.3 (methine). 114.8 (aromatic quat), 66.1 (methylene-Coc), 57.7 (OCH$_3$). IR (neat) ν 3295, 3116, 3025, 2957, 2242, 1956, 1927, 1814, 1732, 1697, 1592, 1532, 1450, 1305, 1245, 1165, 1090, 1038, 976, 913, 856, 836, 819, 766, 743, 692 cm$^{-1}$; MS m/z 311 (M$^+$. +1), 268, 212, 188, 152, 117.

Synthesis of Protected PBD 2-((E)-3-phenyl-allyloxycarbonylamino)-benzoic acid (73)

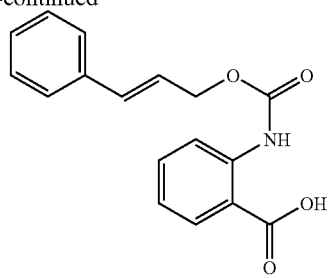

73

Compound 72 (7.989 g, 26 mmol) was dissolved in aqueous methanol (3:1, 1200 mL) with THF (2-3 drops) to aid solubility. A solution of LiOH (3.12 g, 130 mmol) was added as a solid to the stirring reaction mixture at 0° C. and stirred for 40 minutes. The reaction was allowed to return to room temperature and stirred for 16 hours, at which time TLC (70% Pet ether:EtOAc) revealed complete reaction. Excess methanol and THF were evaporated in vacuo and the remaining solution acidified to pH 2 with conc. HCl, to furnish a colourless precipitate (73), which was collected by filtration and dried (92%). $^1$H NMR (250 MHz, CDCl$_3$) δ 10.85 (s, 1H, acid OH), 10.80 (s, 1H, carbamate NH), 8.34-8.32 (d, 1H, aromatic H), 8.00 (dd, 1H, J=1.5, 7.9 Hz, aromatic H), 7.70-7.55 (m, 1H, aromatic H), 7.53-7.10 (m, 5H, aromatic coc), 6.75 (d, 1H, J=16 Hz, 3'-H), 6.46 (dt, 1H, J=6.2, 16 Hz, 2'-H), 4.82 (d, 2H, J=6.3 Hz, 1'-H); $^{13}$C NMR (62.9 MHz, CDCl$_3$) δ 170.6 (ester carbonyl), 153.2 (CO carbamate), 142.0 (aromatic quat), 137.1 (aromatic quat), 135.1 (methine), 134.5 (alkenic methine), 132.5 (methine), 131.0 (methine), 127.7 (methine), 125.0 (alkenic methine), 122.6 (methine), 119.0 (methine), 116.5 (aromatic quat), 66.5 (methylene Coc). MS m/z 297 (M$^+$. +1), 265, 252, 236, 224, 205, 189, 176, 149, 138, 117.

{2-[1-(3-hydroxymethyl-pyrrolidin-1-yl)-methanoyl]-phenyl}carbamic acid (E)-3-phenyl-allyl ester (74)

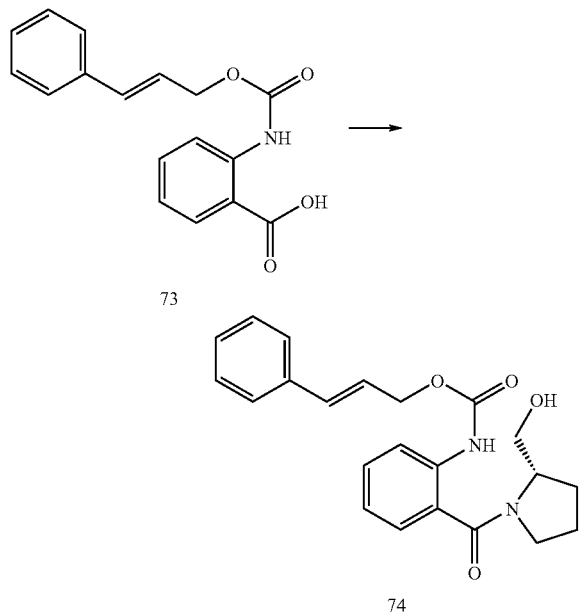

A solution of DCC (4.54 g, 22 mmol) dissolved in the minimum of CH$_2$Cl$_2$ was added dropwise to compound 73 (6 g, 0.020 mol) in CH$_2$Cl$_2$ at −5C, whilst stirring, with a catalytic amount of DMF (10 drops). The reaction mixture was stirred for a further five minutes before HOBt (3.0 g, 22 mmol) in CH$_2$Cl$_2$ was added. The reaction mixture was allowed to stir for 1 hour at −5° C., then left to stir for 12 hours at room temperature. The colourless precipitate of DCU was removed by filtration and the remaining reaction mixture cooled to −5° C. (S)-pyrrolidinemethanol (2.37 mL, 24 mmol) was added and the reaction mixture allowed to warm to room temperature and, stirred for 12 hours. TLC (70% Pet ether/EtOAc) revealed reaction completion. The reaction mixture was washed with NaHCO$_3$ (4×100 mL), NH$_4$Cl (4×100 mL), H$_2$O (4×100 mL), brine (4×100 mL) and dried over MgSO$_4$. Purification was achieved via flash column chromatography (60% pet ether/EtOAc) to furnish compound 74 as a stiff brown oil (95%). $^1$H NMR (250 MHz, CDCl$_3$); δ 8.69 (s, 1H, NH), 8.13 (d, 1H, J=8.2 Hz, aromatic H), 7.42-7.22 (m, 6H, Coc aromatic H and aromatic H), 7.06 (ddd, 1H, J=1.07, 7.6, 7.5, aromatic H), 6.70 (d, 1H, J=16 Hz, 3'-H), 6.34 (dt, 1H, J=6.4, 18 Hz, 2'-H), 4.81 (dd, 2H, J=1.1, 6.4, 1'-H), 4.40 (br, s, 1H, H-11a), 3.85-3.42 (m, 4H, H-11, H-3), 2.06-1.70 (m, 4H, 1-H, H-2); $^{13}$C NMR (62.9 MHz, CDCl$_3$) δ 171.3 (ester carbonyl), 136.6 (aromatic quat), 134.6 (methine), 131.3 (methine), 129.0 (methine), 128.5 (methine), 128.0 (methine), 127.1 (methine), 123.9 (alkenic methine), 122.7 (methine), 121.3 (methine), 67.0 (Coc, C-1), 66.2 (methylene Coc), 61.1 (methine, C-11a), 51.9 (methine, C-3), 28.8 (methine, C-1), 25.5 (methine, C-2); MS m/z; 381 (M$^+$. +1), 363, 337, 308, 279, 261, 247, 229, 203, 117.

(11S, 11aS)-11-hydroxy-10-((E)-3-phenyl-allyloxycarbonyl) hexahydro-5H-pyrrolo[2,1-c][1,4]benzodiazepin-5-one (75)

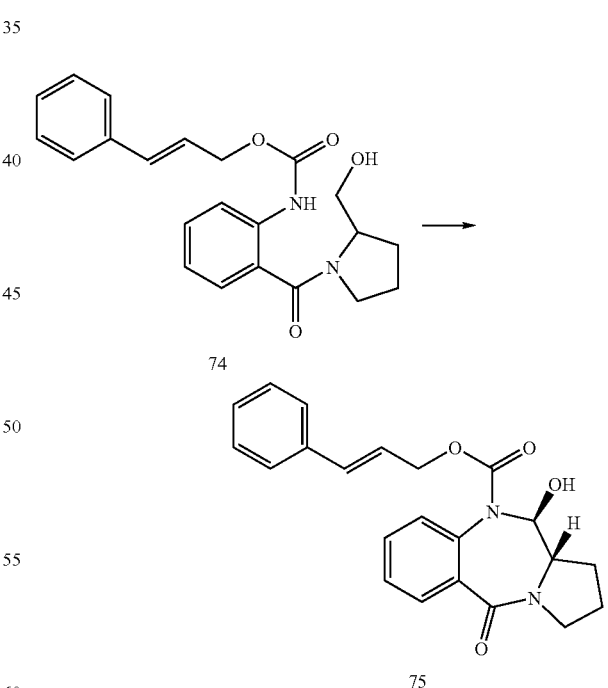

A solution of DMSO (4.6 mL 65 mmol) in CH$_2$Cl$_2$ was added over 20 minutes to a stirring solution of oxalyl chloride (16.5 mL, 33 mmol) in CH$_2$Cl$_2$ at −40° C. and left to stir for a further 20 minutes. Compound 74 (7 g, 18 mmol) was dissolved in CH$_2$Cl$_2$ and added over a period of 45 minutes to the reaction mixture. Once addition was complete, the reaction mixture was stirred at −40° C. for a further 60 minutes.

Over a period of 30 minutes TEA (10.8 mL, 77 mmol) in CH$_2$Cl$_2$ was added and stirred for a further 30 minutes, and then warmed to room temperature. The reaction mixture was washed with 1N HCl (3×100 mL), H$_2$O (3×100 mL), brine (3×100 mL) and dried over MgSO$_4$. Purification was achieved via flash column chromatography (AcOH:MeOH: CDCl$_3$ 1:10:100) and excess solvent was removed in vacuo to yield compound 75 as a solid colourless powder (92% yield). $[\alpha]^{22.4}_D$=+256° (c=1, CHCl$_3$); $^1$H NMR (250 MHz, CDCl$_3$) δ 7.76 (dd, 1H, J=1.6, 7.5 Hz, aromatic H), 7.60-7.30 (m, 5H, Coc aromatic H), 6.46 (d, 1H, J=16 Hz, 3'-H), 6.30-5.94 (m, 1H, 2'-H), 5.71 (d, 1H, J=9.7 Hz, H-11), 4.86-4.72 (m, 2H, 1'-H), 3.77-3.41 (m, 4H, 11a-H, H-3), 2.17-1.78 (m, 4H, 1-H, H-2); $^{13}$C NMR (62.9 MHz, DMSO) δ 163.9 (C=O amide), 155.8 (C=O carbinolamine), 136.7 (aromatic quat), 135.0 (aromatic quat), 131.8 (methine), 131.4 (methine), 129.5 (methine), 129.1 (methine), 128.8 (methine), 127.3 (methine), 86.0 (methine CC-11), 67.1 (methylene coc), 61.2 (methine C-11a), 46.8 (methylene C-3), 29.1 (methylene C-1), 23.5 (methylene C-2); MS m/z 379 (M$^+$. +1), 363, 317, 277, 245, 225, 117.

PBD Deprotection

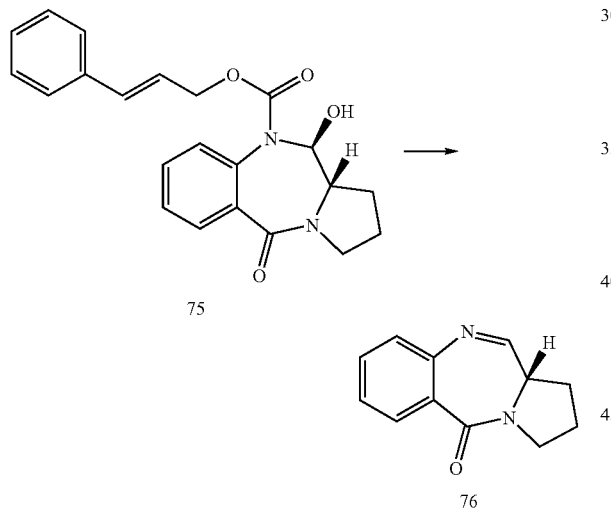

A solution of Pd(PPh$_3$)$_4$ (0.038 g, 0.0325 mmol) in CH$_2$Cl$_2$ was added to a solution of 75 (0.5 g, 1.3 mmol), TPP (0.017 g, 0.065 mmol) and pyrrolidine (0.097 g, 1.37 mmol) in CH$_2$Cl$_2$. Flash column chromatography (2% MeOH/CDCl$_3$) furnished a colourless powder in a 76% yield as a mixture of carbinolamine methyl ether and imine forms. $^1$H NMR (250 MHz, CDCl$_3$) δ 8.02 (dd, 1H, J=1.6, 23.2 Hz, aromatic H), 7.78-7.75 (m, 1H, aromatic H), 7.68-7.23 (m, 1H, aromatic H), 7.20-7.15 (m, 1H, aromatic H), 6.86-6.81 (m, 1H, aromatic H), 6.61 (d, 1H, J=8.2 Hz aromatic H), 5.66 (d, 1H, J=8.7 Hz, N10-H, carbinolamine), 5.34 (d, 1H, J=5.8 Hz, N10-H, methyl ether), 4.57 (d, 1H, J=6.2 Hz 11-H, R diastereomer), 4.41 (d, 1H, J=8.9 Hz, 11-H, S diastereomer), 3.91- 3.32 (m, 3H, H-3, H-11a), 3.45 (s, 11-OMe, R diastereomer), 3.32 (s, 11-OMe, S diastereomer), 2.31-1.32 (m, 4H, 2-H, H-1); $^{13}$C NMR (62.9 MHz, CDCl$_3$) δ 165.2 (C=O amide), 164.9 (imine signal), 146.1 (aromatic quat), 131.8 (methine), 130.7 (methine), 127.2 (methine), 126.9 (methine), 85.8 (C-11, carbinolamine methyl ether), 60.0 (C-11a, 1H), 53.9 (methoxy —OMe), 47.1 (1H, C-3), 30.0 (1H, C-1), 24.6 (1H, C-2); MS m/z 201 (M$^+$. +1 imine form), 188, 177, 132, 117, 100, 90.

The invention claimed is:

1. A method of synthesis of a compound of formula (I):

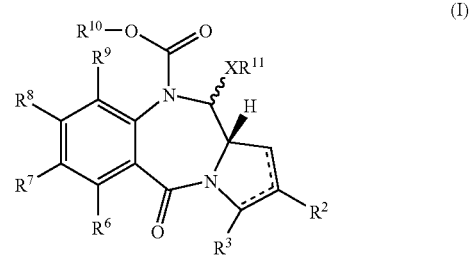

comprising the steps of:
(a) reacting a compound of formula (II) with a compound of formula (III) to yield a compound of formula (IV):

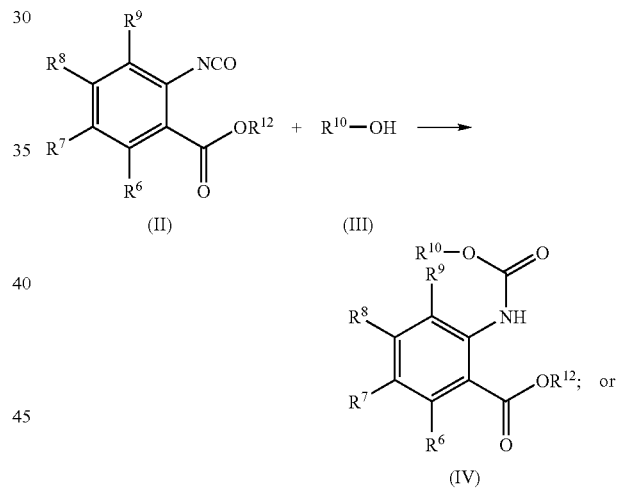

(b) converting the compound of formula (IV) to a compound of formula (I):

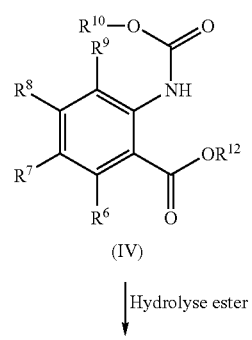

-continued

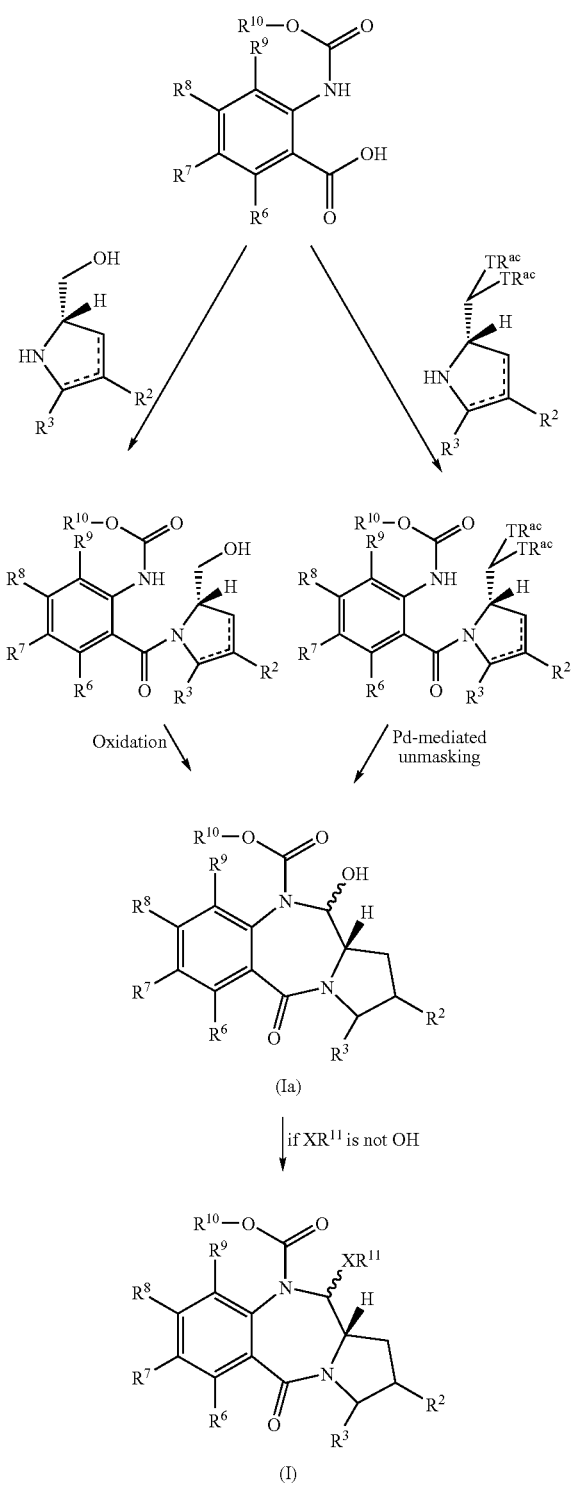

(Ia)

↓ if XR¹¹ is not OH (I)

wherein
the dotted lines indicate the optional presence of a double bond between C1 and C2 or C2 and C3;
R² and R³ are independently selected from —H, —OH, =O, =CH₂, —CN, —R, OR, =CH—R, O—SO₂—R, CO₂R and COR;

R⁶, R⁷ and R⁹ are independently H, R, OH, OR, SH, SR, NH₂, NHR, NRR', nitro, Me₃Sn and halo;

R⁸ is either selected from H, R, OH, OR, SH, SR, NH2, NHR, NRR', nitro, Me₃Sn and halo or the compound is a dimer with each monomer being the same of different and being of the relevant formula, where the R⁸ groups of each monomer form together a bridge having the formula —X—R"—X—, where R" is a $C_{3-12}$ alkylene group, which chain may be interrupted by one or more heteroatoms and/or aromatic rings, and each X is independently selected from O, S and NH;

R¹⁰ is such that R¹⁰—OC(=O)— forms a nitrogen protecting group;

R¹¹ is either H or R;

R¹² is an optionally substituted $C_{1-4}$ alkyl group;

P and Q are such that —CPQ is a masked aldehyde group;

wherein R and R' are independently selected from optionally substituted $C_{1-20}$ alkyl, $C_{3-20}$ heterocyclyl, and $C_{5-20}$ aryl;

wherein T is O or S, and each $R^{ac}$, is independently selected from $C_{1-10}$ alkyl or together can be a $C_{1-3}$ alkylene group.

2. A method according to claim 1, wherein the compound of formula (II) is synthesized by:

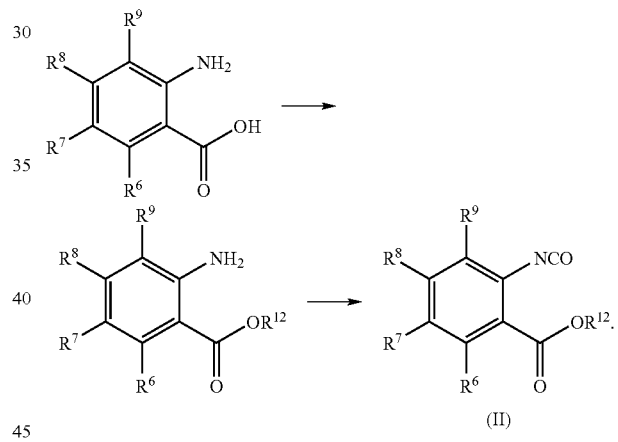

3. A method of synthesis of a compound of formula (I):

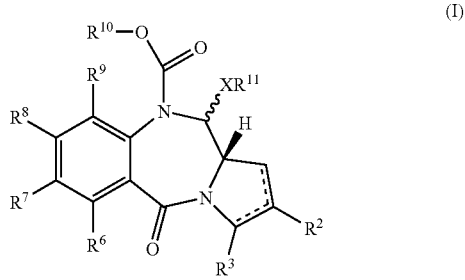

comprising the steps of:
(a) reacting a compound of formula (V) with a compound of formula (III) to yield a compound of formula (VI):

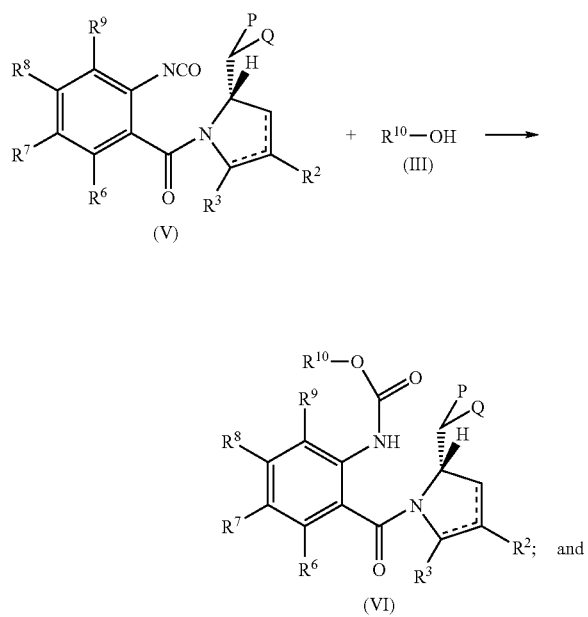

(b) converting the compound of formula (VI) to the compound of formula (I):

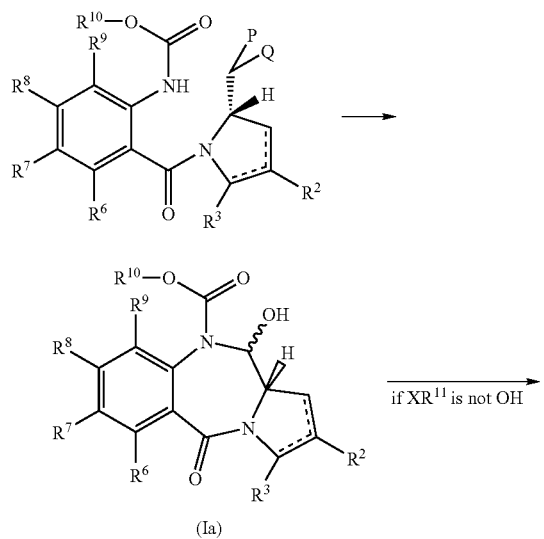

wherein
the dotted lines indicate the optional presence of a double bond between C1 and C2 or C2 and C3;

$R^2$ and $R^3$ are independently selected from —H, —OH, =O, =CH$_2$, —CN, —R, OR, =CH—R, O—SO$_2$—R, CO$_2$R and COR;

$R^6$, $R^7$ and $R^9$ are independently H, R, OH, OR, SH, SR, NH$_2$, NHR, NRR', nitro, Me$_3$Sn and halo;

$R^8$ is either selected from H, R, OH, OR, SH, SR, NH$_2$, NHR, NRR', nitro, Me$_3$Sn and halo or the compound is a dimer with each monomer being the same of different and being of the relevant formula, where the $R^8$ groups of each monomer form together a bridge having the formula —X—R"—X—, where R" is a C$_{3-12}$ alkylene group, which chain may be interrupted by one or more heteroatoms and/or aromatic rings, and each X is independently selected from O, S and NH;

$R^{10}$ is such that $R^{10}$—OC(=O)— forms a nitrogen protecting group;

$R^{11}$ is either H or R;

$R^{12}$ is an optionally substituted C$_{1-4}$ alkyl group;

P and Q are such that —CPQ is a masked aldehyde group;

wherein R and R' are independently selected from optionally substituted C$_{1-20}$ a C$_{3-20}$ heterocyclyl, and C$_{5-20}$ aryl.

4. A method according to claim 3, wherein the compound of formula (IV) is synthesized by:

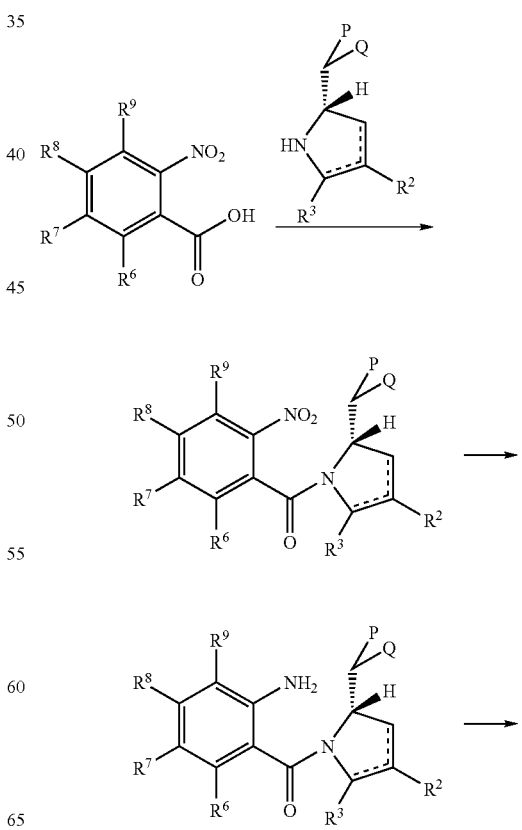

-continued

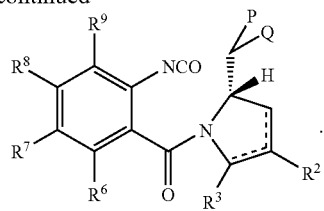

5. A compound of formula (IV):

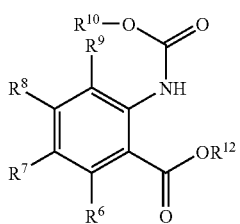

wherein:
R$^6$ and R$^7$ are independently H, R, OH, OR, SH, SR, NH$_2$, NHR, NRR', nitro, Me$_3$Sn and halo;

R$^9$ is H;
R$^8$ is either selected from H, R, OH, OR, SH, SR, NH2, NHR, NRR', nitro, Me$_3$Sn and halo or the compound is a dimer with each monomer being the same of different and being of the relevant formula, where the R$^8$ groups of each monomer form together a bridge having the formula —X—R"—X—, where R" is a C$_{3-12}$ alkylene group, which chain may be interrupted by one or more heteroatoms and/or aromatic rings, and each X is independently selected from O, S and NH;
R$^{10}$ is such that R$^{10}$—OC(=O)— forms a nitrogen protecting group; and
R$^{12}$ is an optionally substituted C$_{1-4}$ alkyl group,
wherein R and R' are independently selected from optionally substituted C$_{1-20}$ alkyl, C$_{3-20}$ heterocyclyl, and C$_{5-20}$ aryl.

6. A method according to claim 1 or claim 3, wherein R$^{10}$ is an optionally substituted C$_{1-30}$ alkyl group, C$_{3-30}$ heterocylyl group or a C$_{5-30}$ aryl group or a divalent version of one of these groups linked to a solid support.

7. A compound according to claim 5, wherein R$^{10}$ is an optionally substituted C$_{1-30}$ alkyl group, C$_{3-30}$ heterocylyl group or a C$_{5-30}$ aryl group or a divalent version of one of these groups linked to a solid support.

* * * * *